United States Patent
Klaerner et al.

(10) Patent No.: US 6,559,255 B2
(45) Date of Patent: *May 6, 2003

(54) CONTROLLED FREE RADICAL EMULSION AND WATER-BASED POLYMERIZATIONS AND SEEDED METHODOLOGIES

(75) Inventors: Gerrit Klaerner, Campbell, CA (US); Adam Safir, Oakland, CA (US); Ralph B. Nielsen, San Jose, CA (US); Bernd Jandeleit, Palo Alto, CA (US); Peter Huefner, San Jose, CA (US); Yunxiao Li, Sunnyvale, CA (US)

(73) Assignee: Symyx Technologies Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/520,583

(22) Filed: Mar. 8, 2000

(65) Prior Publication Data

US 2002/0013430 A1 Jan. 31, 2002

Related U.S. Application Data

(63) Continuation-in-part of application No. 09/347,606, filed on Jul. 2, 1999, now abandoned, and a continuation-in-part of application No. 09/347,607, filed on Jul. 2, 1999, and a continuation-in-part of application No. 09/347,608, filed on Jul. 2, 1999, now abandoned, and a continuation-in-part of application No. 09/347,609, filed on Jul. 2, 1999.
(60) Provisional application No. 60/123,498, filed on Mar. 9, 1999.

(51) Int. Cl.$^7$ .............................. C08F 2/22; C08F 2/38
(52) U.S. Cl. ........................ 526/220; 526/75; 526/88; 526/201; 526/217; 526/236
(58) Field of Search ................................. 526/217, 220, 526/236, 75, 88, 201

(56) References Cited

U.S. PATENT DOCUMENTS

| | | | | |
|---|---|---|---|---|
| 3,422,144 A | * | 1/1969 | Hoffmann et al. | 260/570 |
| 4,581,429 A | | 4/1986 | Solomon et al. | 526/220 |
| 5,322,912 A | * | 6/1994 | Georges et al. | 526/204 |
| 5,401,804 A | | 3/1995 | Georges et al. | 525/267 |
| 5,728,747 A | * | 3/1998 | Kazmaier et al. | 522/11 |
| 6,020,435 A | * | 2/2000 | Blankenship et al. | 525/256 |
| 6,121,397 A | * | 9/2000 | MacLeod et al. | 526/204 |

FOREIGN PATENT DOCUMENTS

| | | | | |
|---|---|---|---|---|
| EP | 891 986 | * | 1/1999 | C08F/2/00 |
| EP | 0 970 973 A1 | | 1/2000 | C08F/4/00 |
| WO | WO 96/18609 | | 6/1996 | C07C/303/24 |
| WO | WO 96/24620 | * | 8/1996 | C08F/4/00 |
| WO | WO 98/07758 | | 2/1998 | C08F/2/38 |
| WO | WO 98/13392 | | 4/1998 | C08F/4/00 |
| WO | WO 98/30601 | | 7/1998 | C08F/4/00 |
| WO | WO 99/00426 | | 1/1999 | C08F/4/00 |
| WO | WO 99/03894 | * | 1/1999 | C08F/2/00 |
| WO | WO 99/46261 | | 9/1999 | C07D/405/12 |

OTHER PUBLICATIONS

Bon et al., Controlled Radical Polymerization in Emulsion, Macromolecules, 30, pp. 324–326 (1997).*
Grimaldi et al. [Synthesis and Application of "Living" Free Radical Polymerization of a New Class of Nitroxyl Radicals, Polymer Preprints, 38(1), pp. 651–652 (1997)].*
Benoit et al. [Controlling Free–Radical polymerization in the Presence of a Novel Asymmetric Nitroxyl Radical, Polymer Preprints, 38 (1), pp. 729–730 (1997)].*
Dondoni [Synthesis of N–Benzyl Nitrones, Synthetic Communications, 24 (18), pp. 2537–2550 (1994)].*
Marestin, C., et al., "Nitroxide Mediated Living Radical Polymerization of Styrene in Emulsion," Macromolecules (1998), 31, 12, 4041–4044.
Lansalot, M. et al., "Nitroxide–Mediated Controlled Free–Radical Emulsion Polymerization of Styrene," Am. Chem. Society, (1999) 40, 2, 317–318.
Entry of free radicals into latex particles in emulsion polymerization. Maxwell, Ian A., et al., Sch. Chem., Univ. Sydney, Sydney, Australia. Macromolecules (1991), 24(7), 1629–1640.
Free radical exit from latex particles. Adams, Mary, et al., Dep. Phys., Univ. Sydney, Sydney, Australia. Polym. Mater. Sci. Eng. (1986), 54 462–464.
Emulsion polymerization. Kinetics of radical capture by particles. Fitch, R.M., et al., Ins. Mater. Sci., Univ. Connecticut, Storrs, Conn. Prog. Colloid Polym. Sci. (1975), 56 1–11.
Direct Measurement of Oligomers Entry Rate onto Latex Particles in a Emulsion Polymerization. Marestin, Catherine, et al., Laboratoire de Chimie et Procedes de Polymerisation, CNRS–CPE, Villeurbanne, Fr. Macromolecules (1998), 31(5), 1686–1689.
B. L. Carvalho and E.L. Thomas, *Phys. Rev. Lett.*, 73, pp. 3321–3324. 1994.
C.J. Haker, et al., (*J. Polym. Sci. Part A: Pol. Chem.* 1998) 36, 2161–2167.
Claverie et al., "Nitroxide Mediated Living Radical Polymerization of Styrene in Emulsion," *Macromolecules*, 1998, 31, 4041–4044.

(List continued on next page.)

Primary Examiner—David W. Wu
Assistant Examiner—Kelechi C. Egwim
(74) Attorney, Agent, or Firm—Fish & Richardson P.C.

(57) ABSTRACT

Nitroxides having an alpha-carbon atom with a destabilizing moiety are effective control agents for emulsion and water-based polymerizations, including the formation of block copolymers from a wide range of monomers. The nitroxide radicals may be used as a free radical or as an adduct with a residue from the initiator. The emulsions have living characteristics, including the re-initiation of polymer chains. Also, a seeded process for emulsions, which includes the step-wise addition of monomer is disclosed, providing access to a wide range of initiator types.

4 Claims, 12 Drawing Sheets

OTHER PUBLICATIONS

Dondoni, et al., (*Synth. Commun.* 1994, 24, 2537–2550).

G. Coulon, D. Ausserre, and T.P. Russell, *J. Phys. (Paris)* 51, 777 (1990).

Georges et al., "The Stable Free–Radical Polymerization Process: Role of Excess Nitroxide," Controlled Radical Polymerization (ACS Symposium Series #685, 1998), pp. 170–179.

German, et al., "Controlled Radical Polymerization in Emulsion," *Macromolecule*, 1997, 30, 324–326.

Grimaldi et al. "Synthesis and Applications to 'Living' Free Radical Polymerization of a New Class of Nitroxyl Radicals," Polymer Preprints, vol. 38, No. 1 (Apr. 1997).

Hawker et al., "Development of a New Class of Rate–Accelerating Additives for Nitroxide–Mediated 'Living' Free Radical Polymerization," *Tetrahedron*, vol. 53, No. 45, pp. 15225–15236 (1997).

Hawker et al., "Development of a Universal Alkoxyamine for 'Living' Free Radical Polymerizations," *J. Am. Chem. Soc.*, 1999, 121(16), pp. 3904–3921.

Janzen et al., *J. Am. Chem. Soc.*, 1986, 108, 6858–6863.

Janzen et al., *J. Am. Chem. Soc.*, 1989, 111, 2066–2070.

Janzen et al., *J. Am. Chem. Soc.*, 91:16, pp. 4481–4490 (Jul. 30, 1969).

J.C. Roberts, et al.(*Tetrahedron Lett.*, 1997) 38, 355–358.

Poehlein et al., "Characterization of Water–Soluble Oligomer in Acrylic Acit–Styrene Emulsion Copolymerization," *J. Appl. Polym. Sci.*, vol. 50, pp. 2173–2183 (1993).

T.P. Russell, G. Coulon, V.R. Deline, and D.C. Miller, *Macromolecules* 22, 4600–4606 (1989).

Ugelstad, et al., "A Kinetic Investigation of the Emulsion Polymerization of Vinyl Chloride," *J. Polymer Sci., Part C*, No. 27, pp. 49–68 (1969).

* cited by examiner

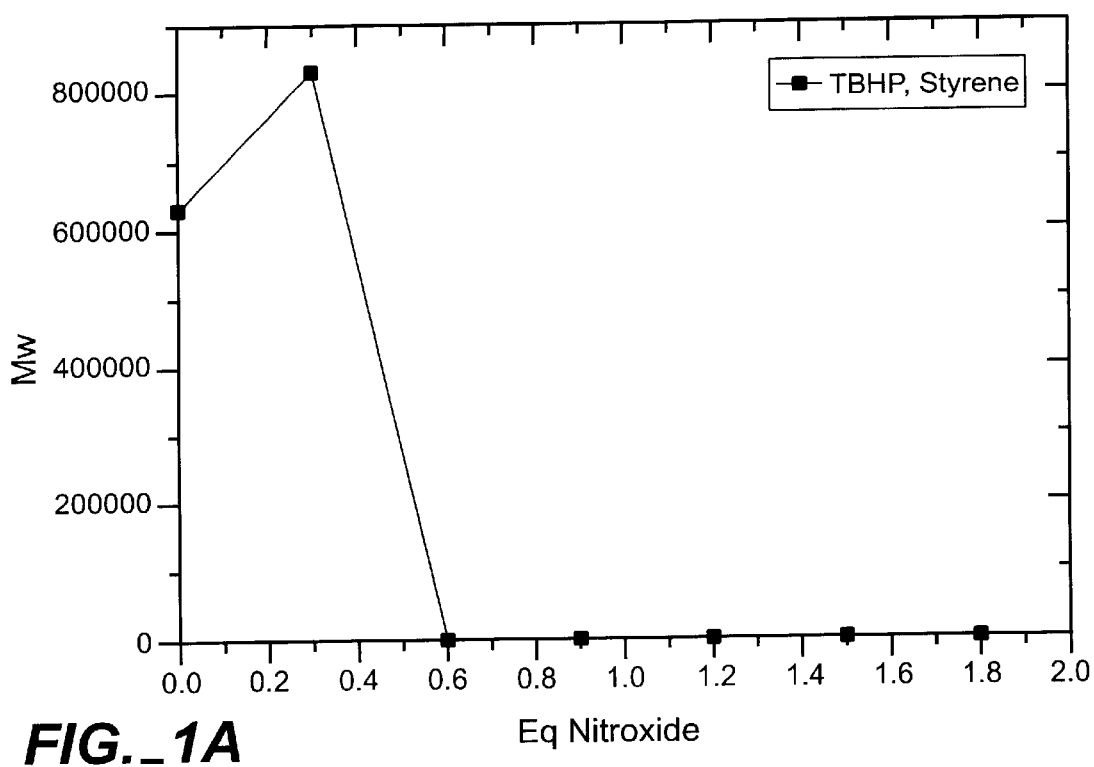
FIG._1A
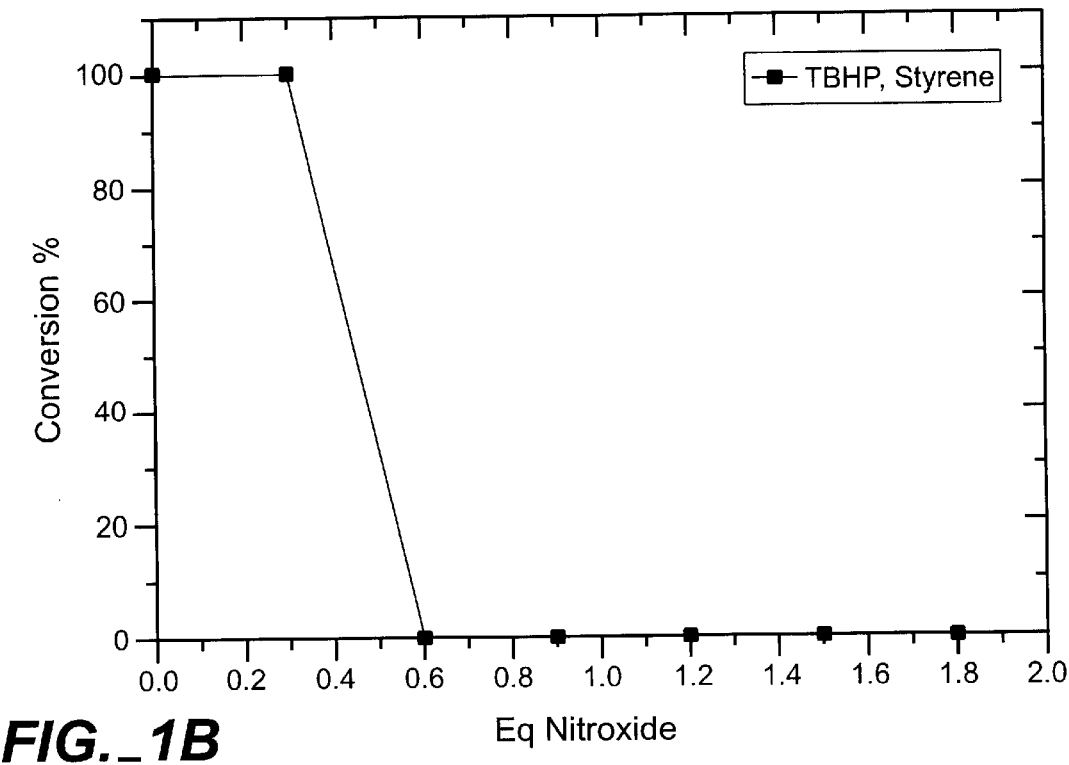
FIG._1B

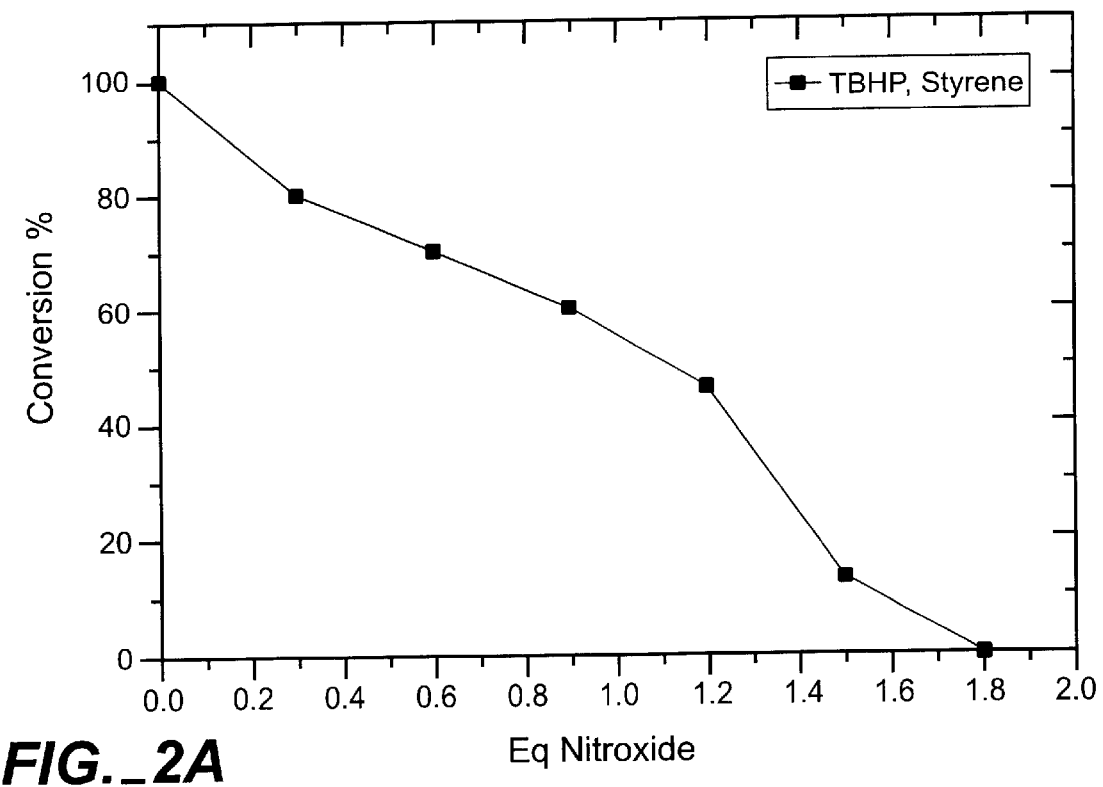
FIG._2A
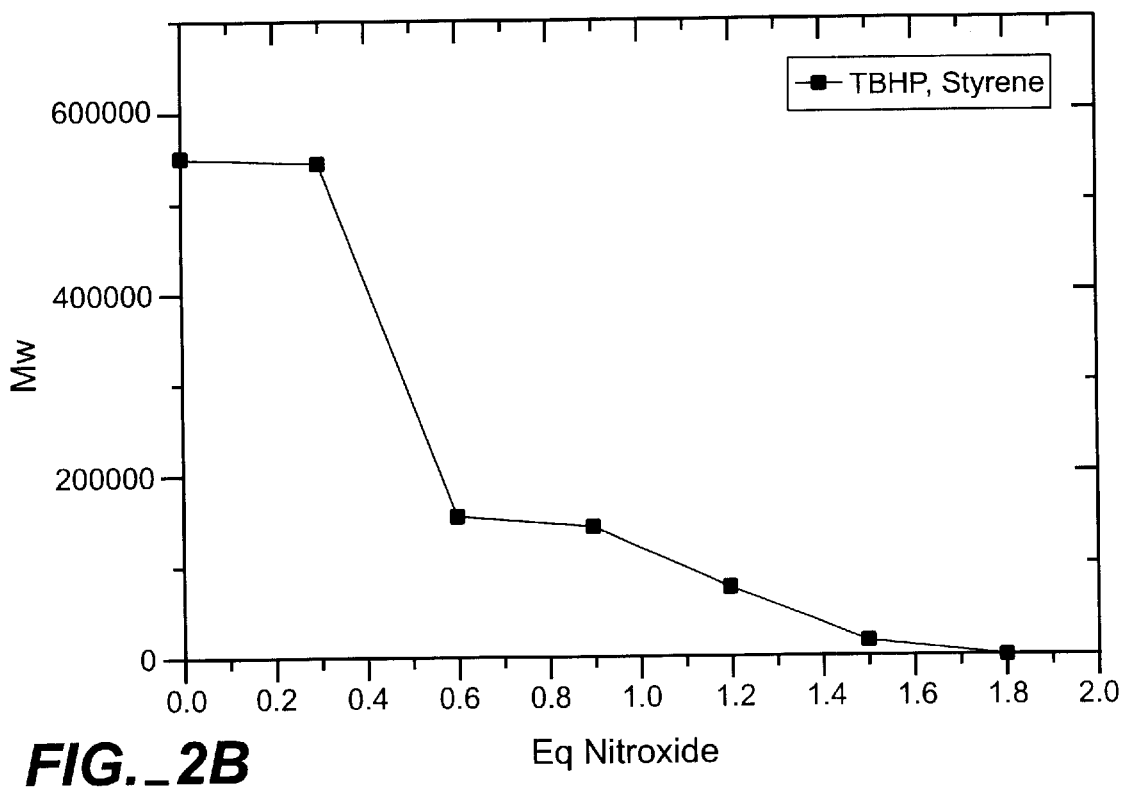
FIG._2B

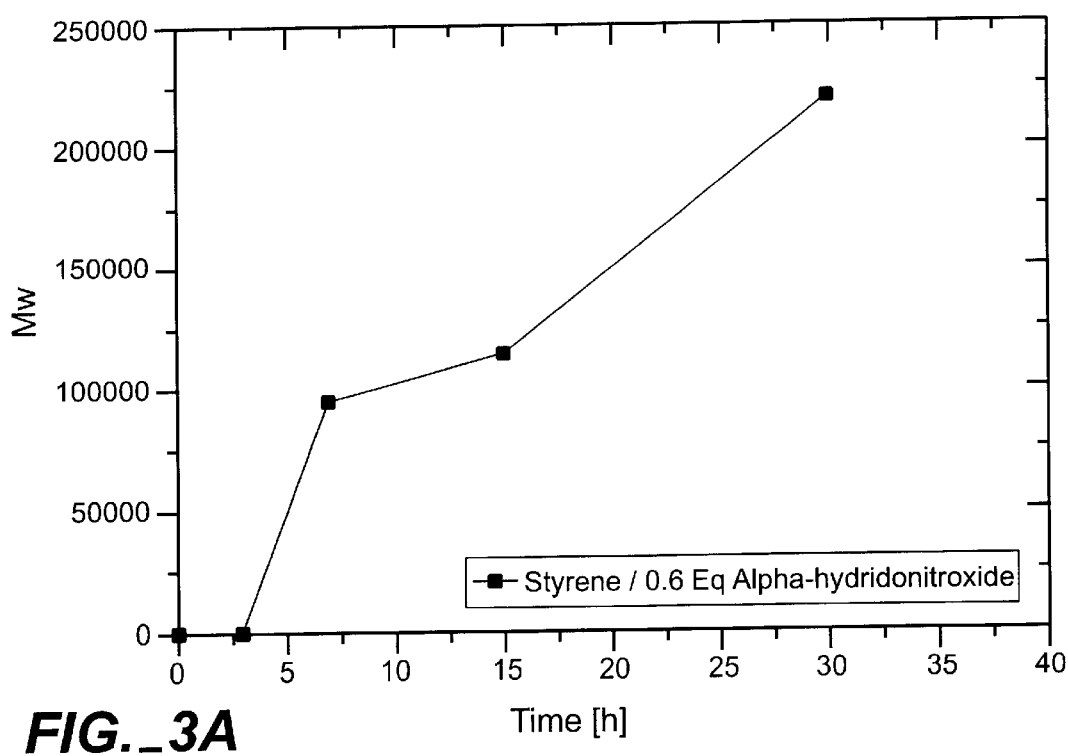
FIG._3A
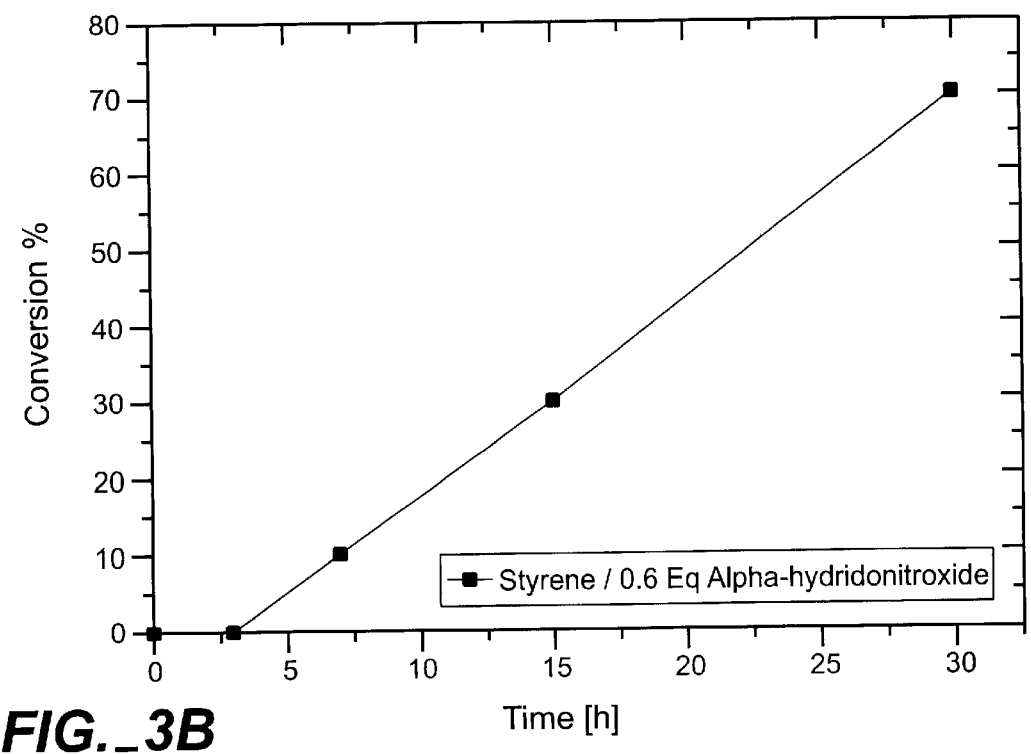
FIG._3B

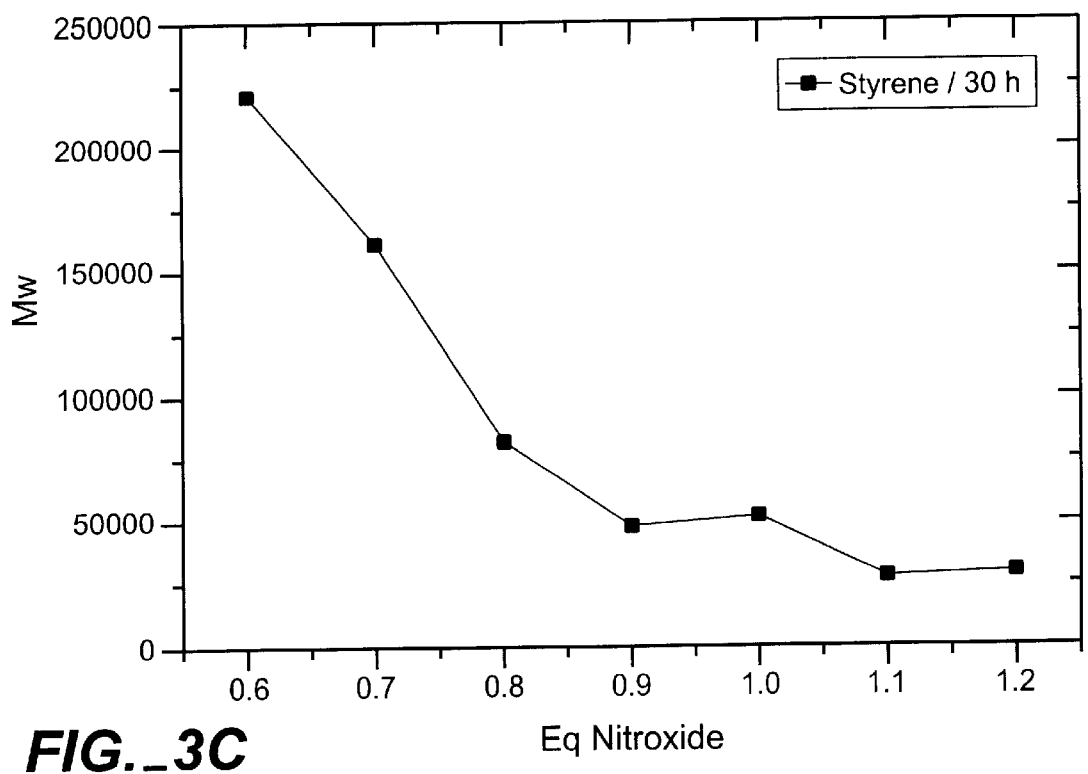
FIG._3C
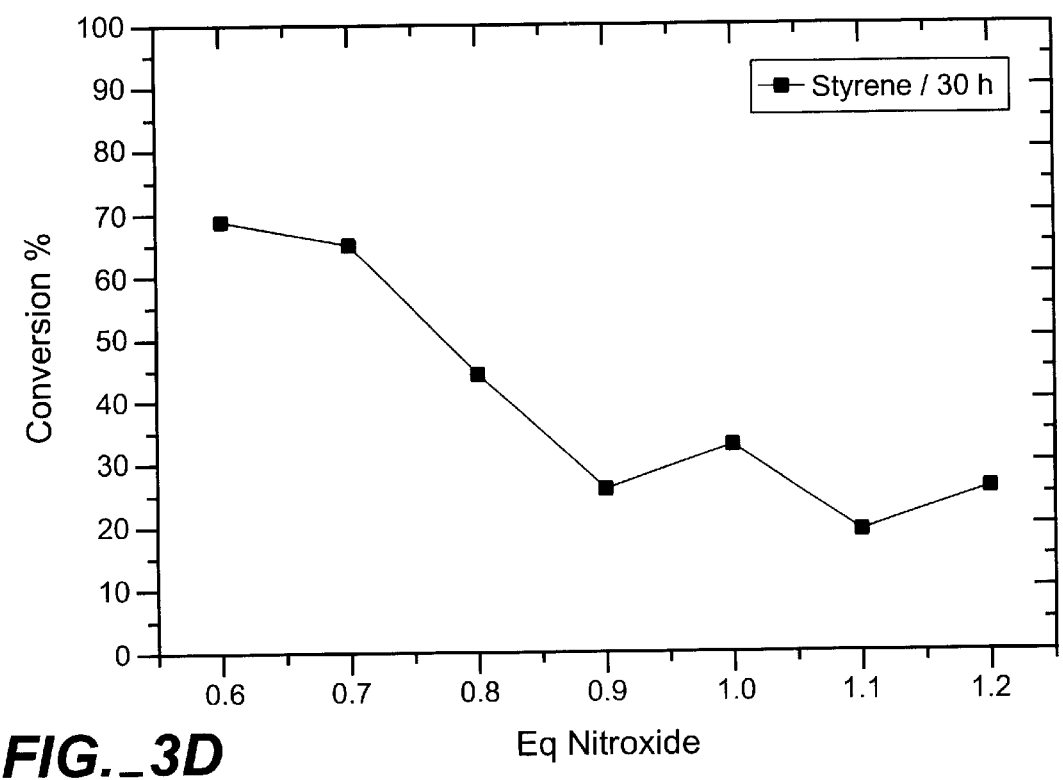
FIG._3D

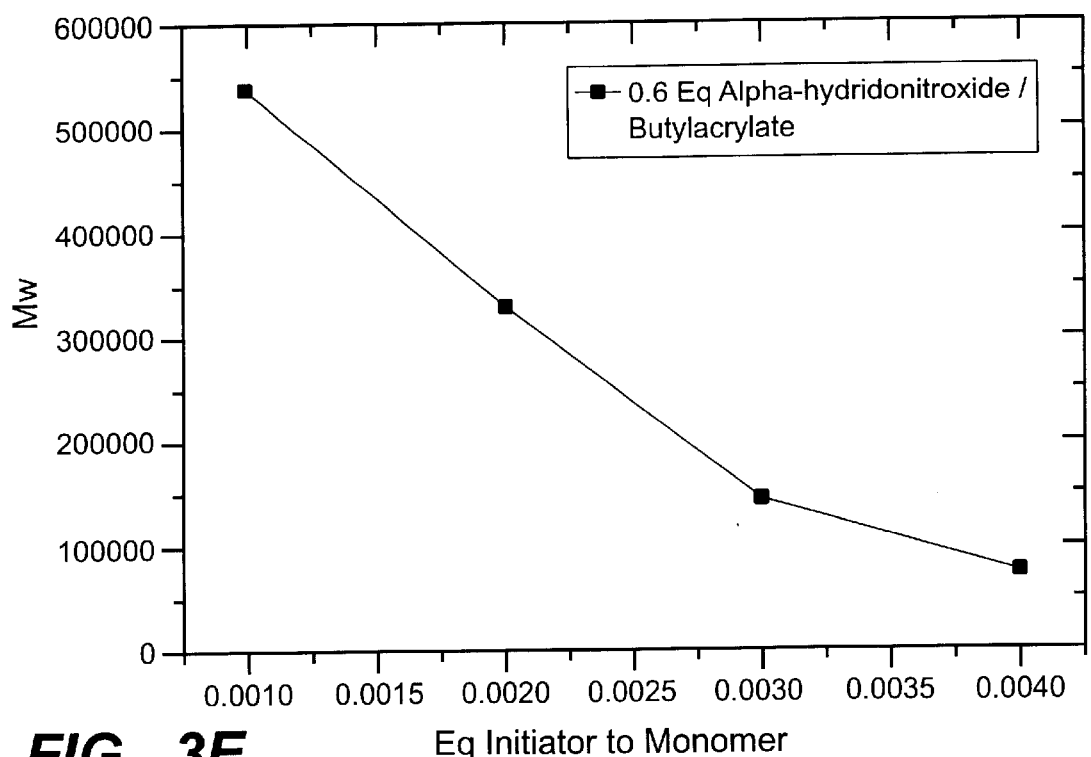
FIG._3E
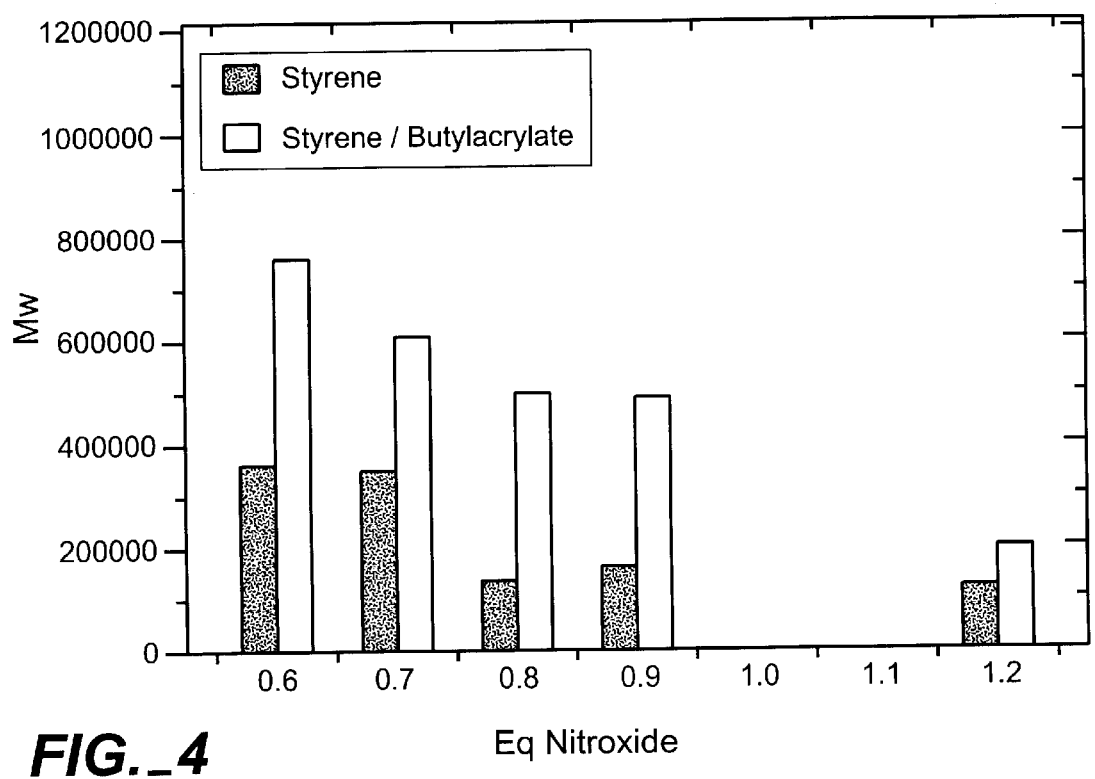
FIG._4

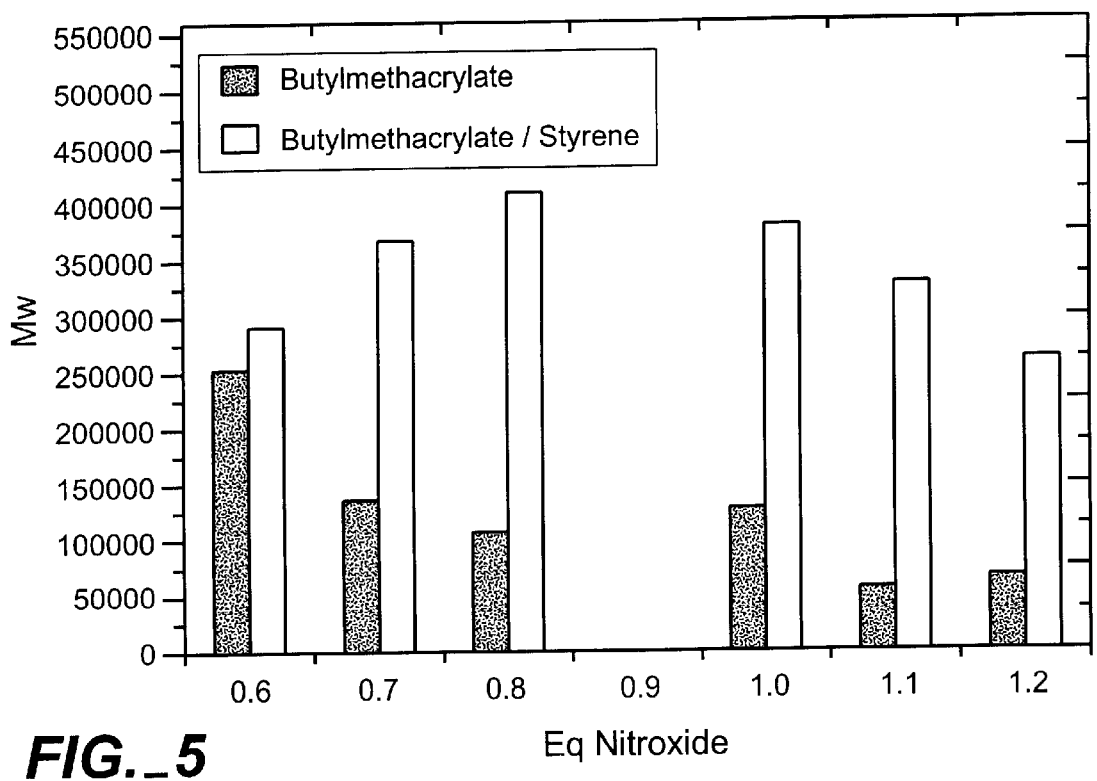
FIG._5
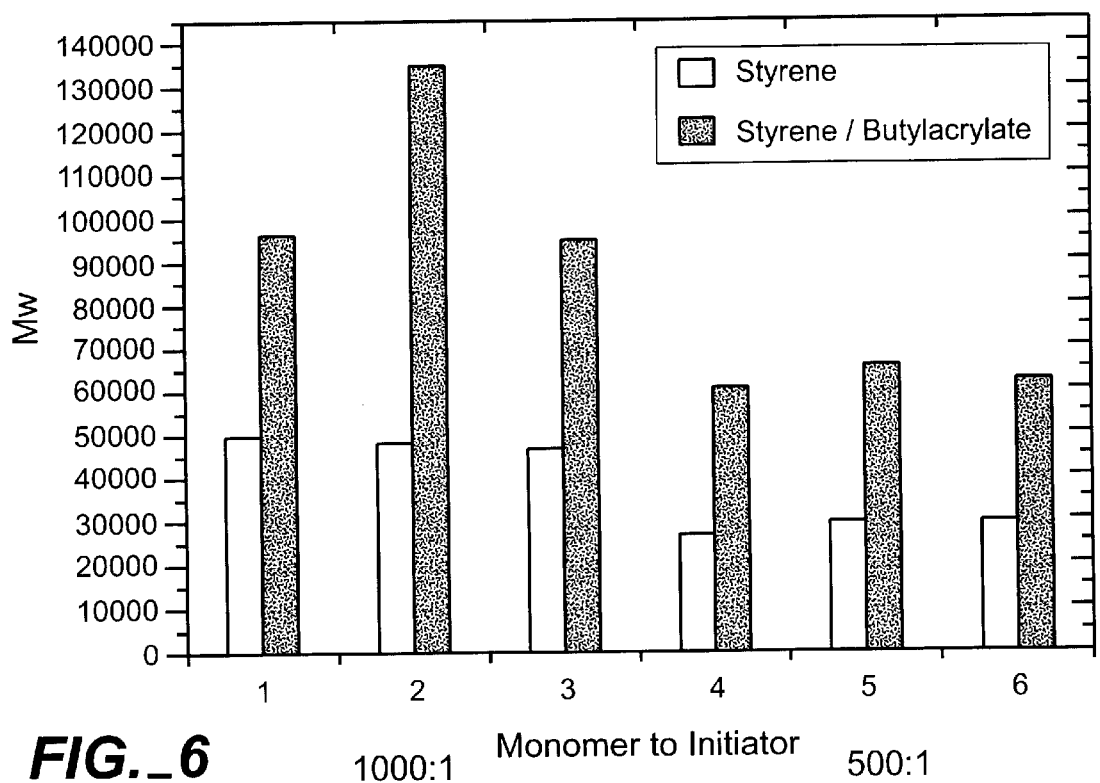
FIG._6

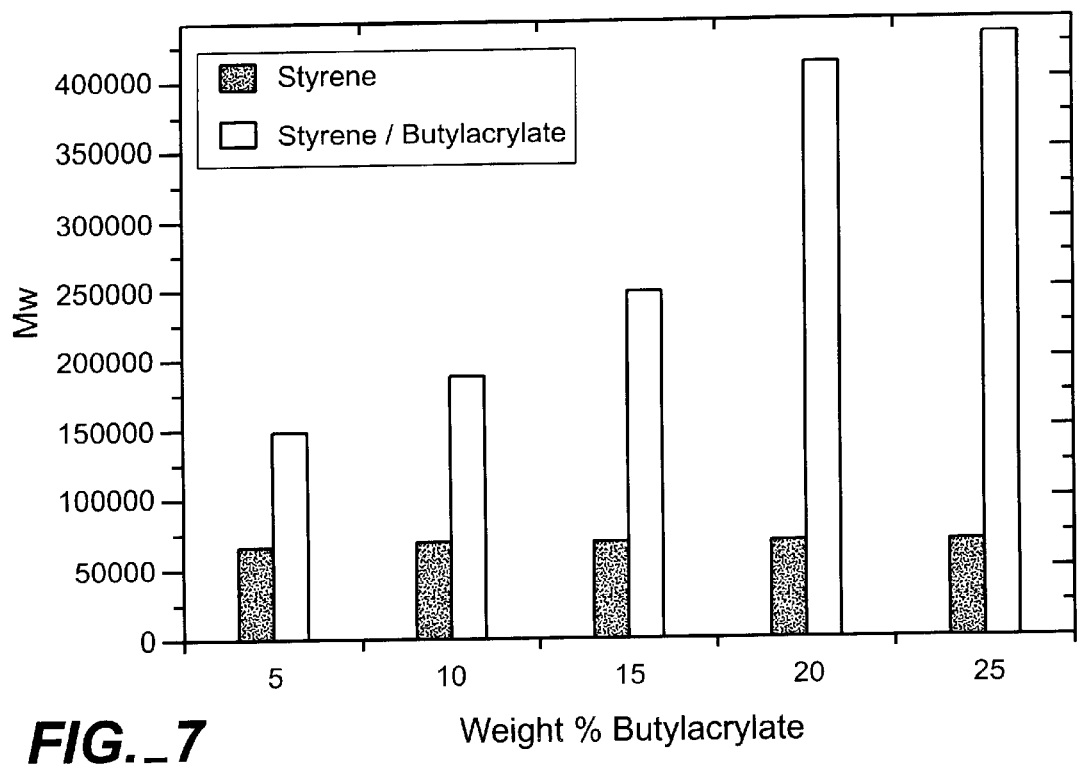
FIG._7
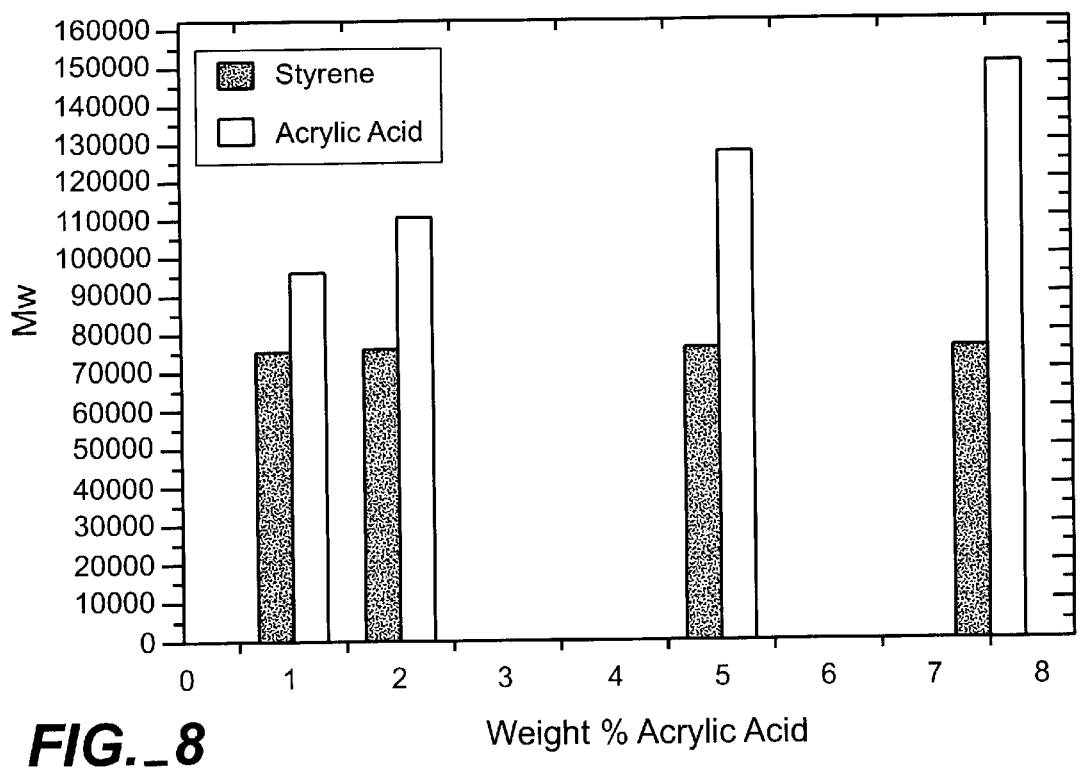
FIG._8

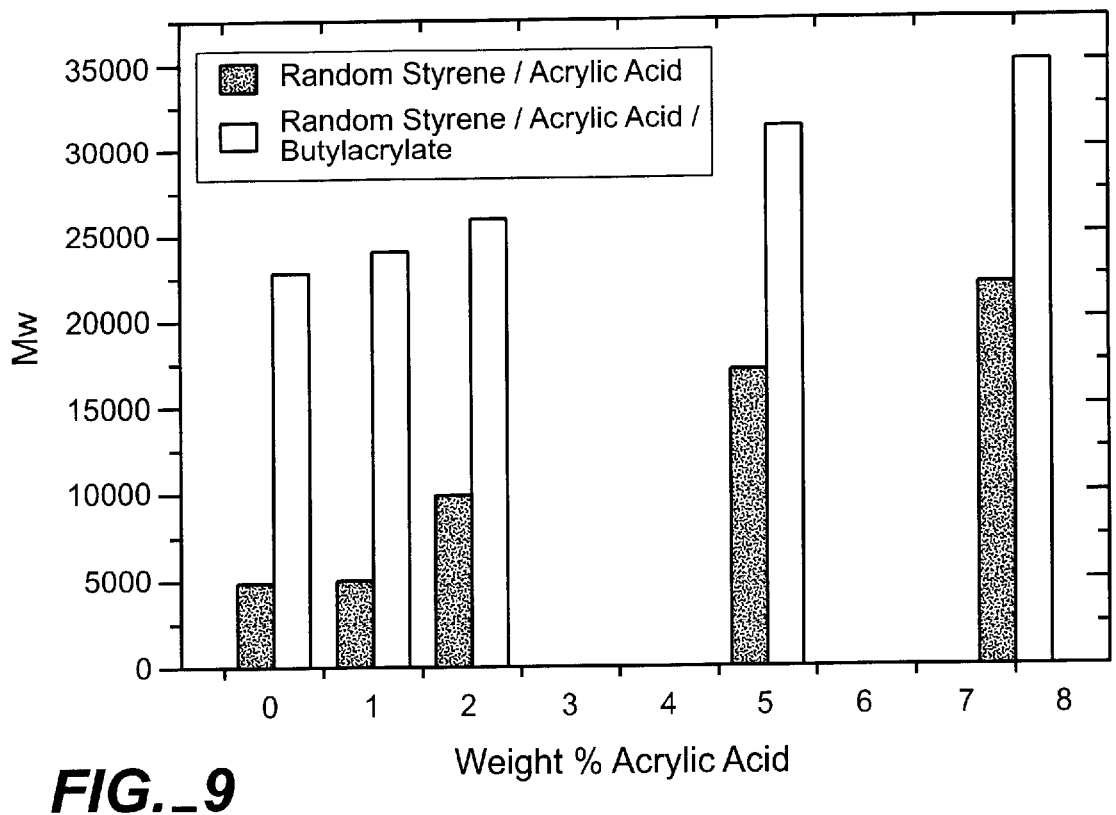
FIG._9
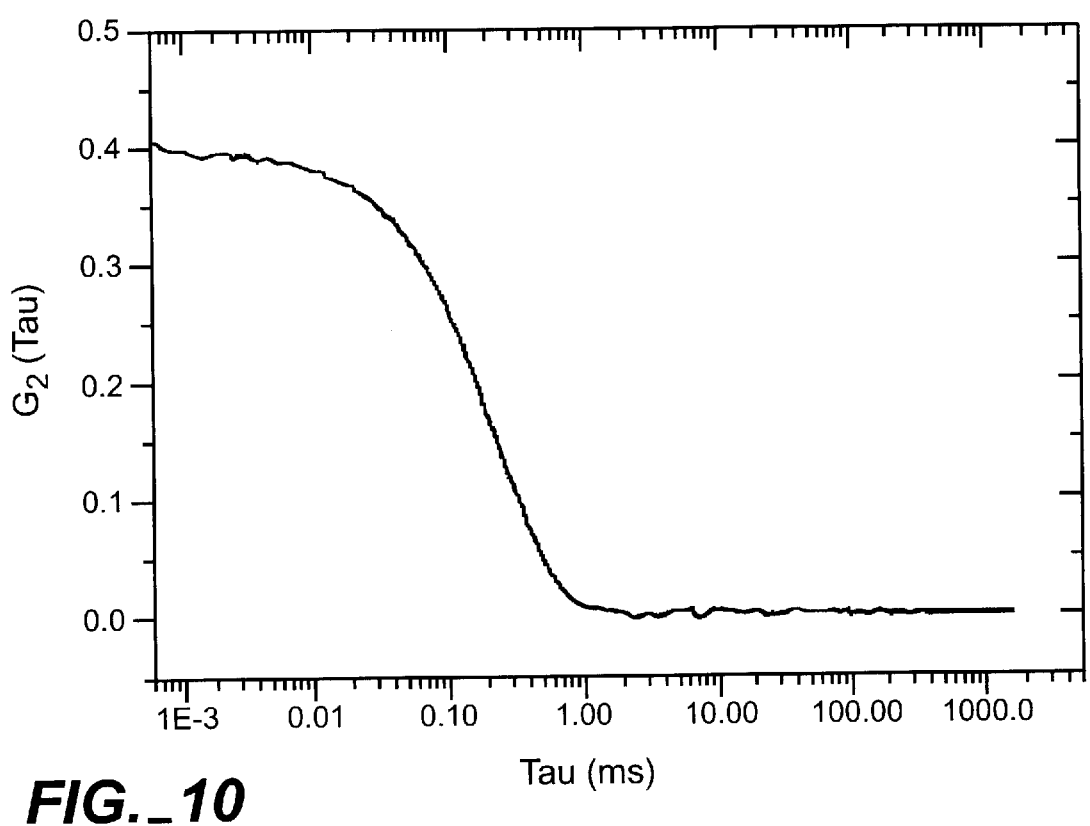
FIG._10

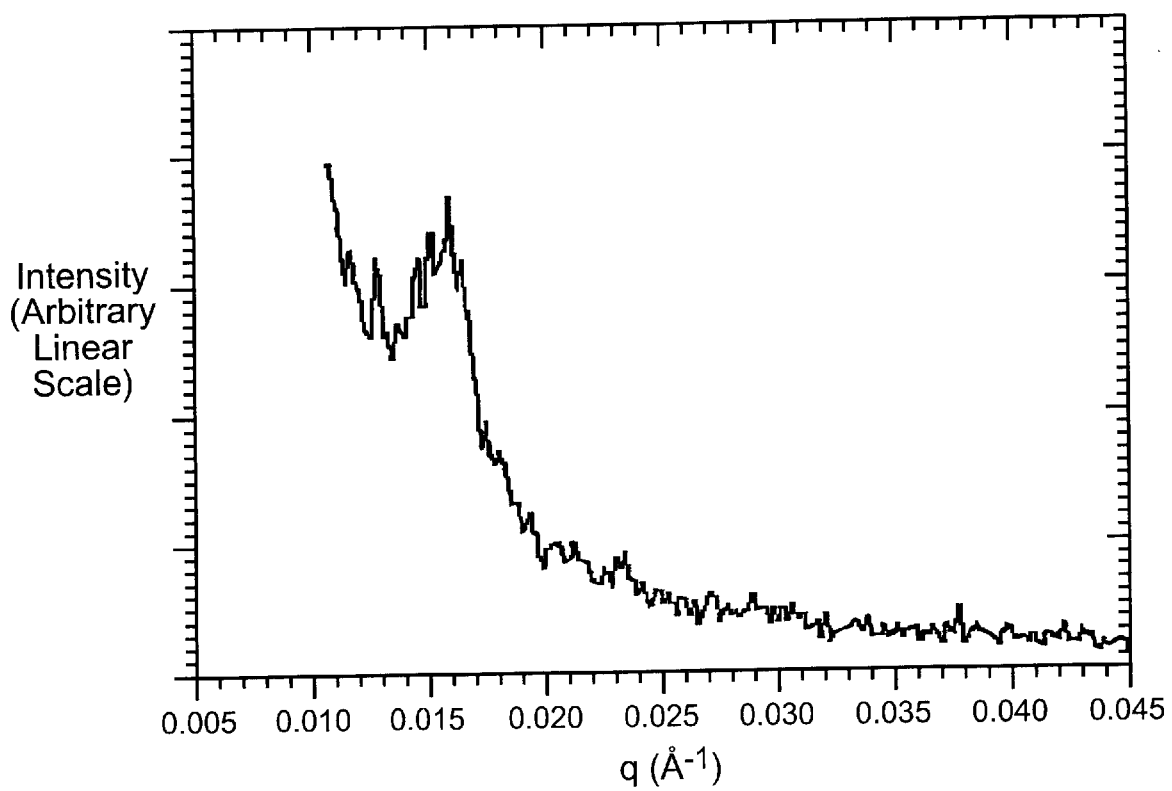
FIG._11
FIG._12

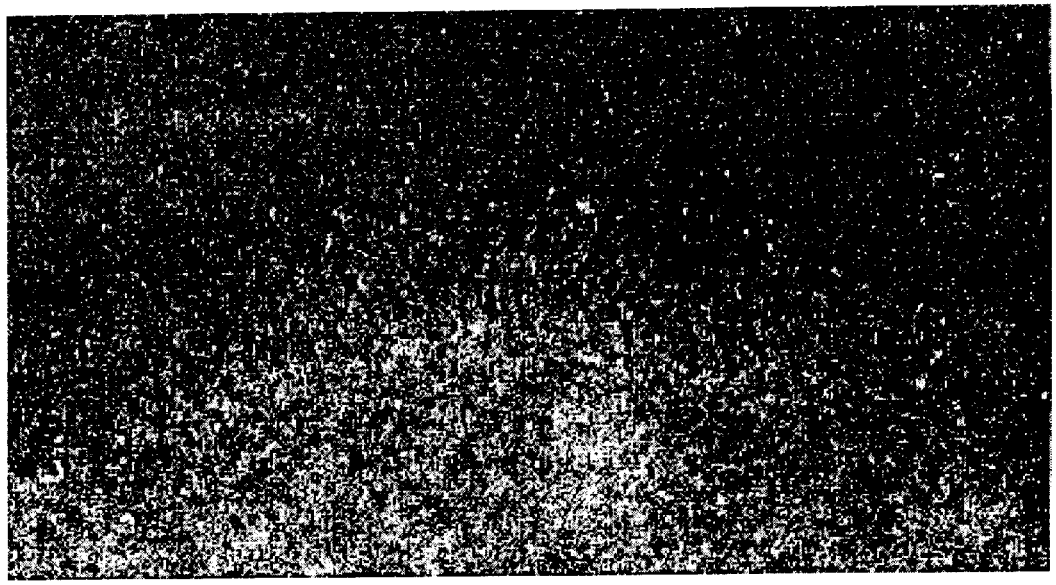
FIG._13A
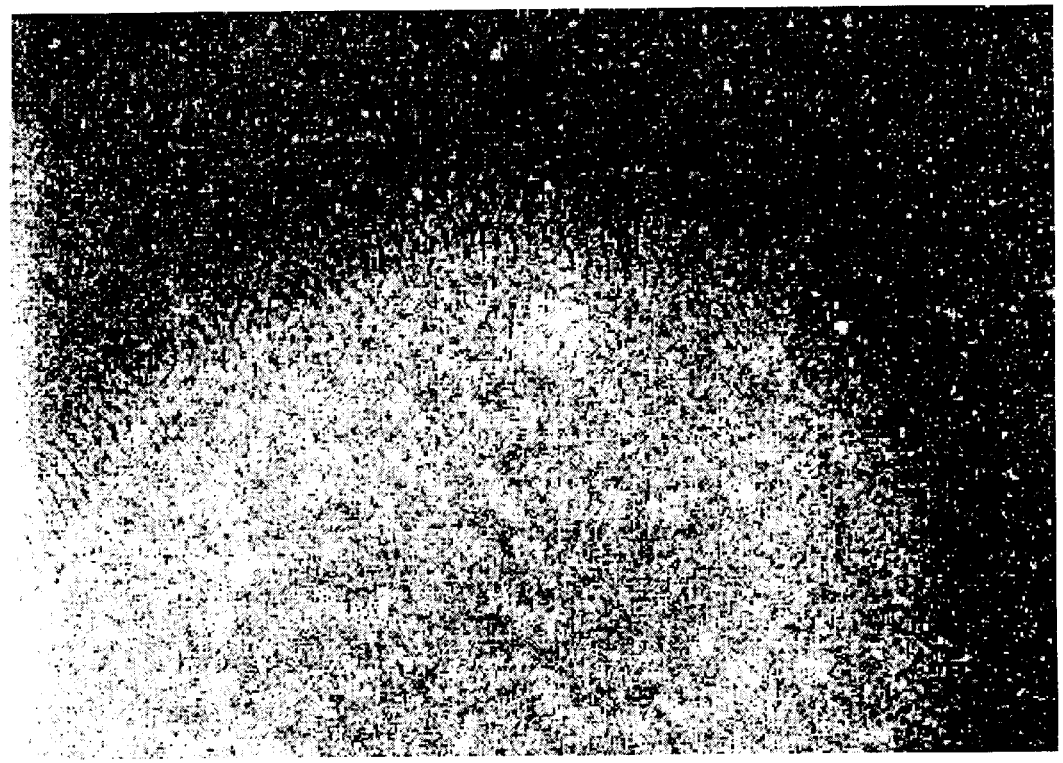
FIG._13B

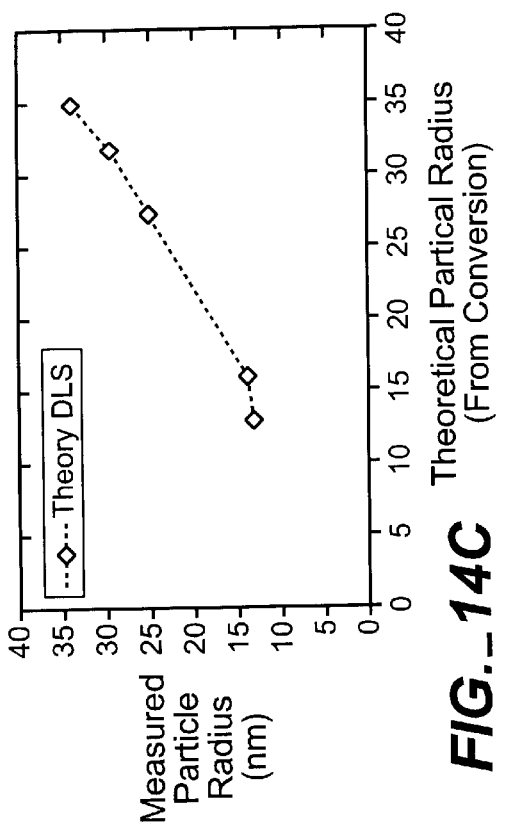
FIG._14C
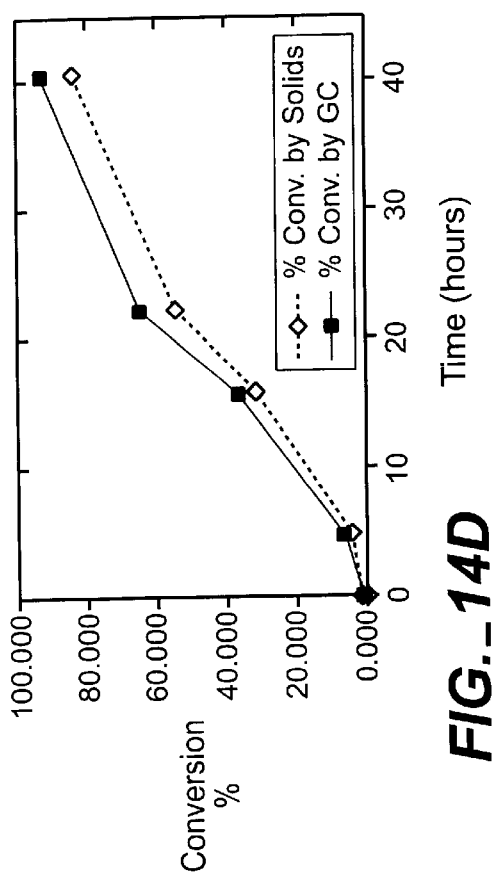
FIG._14D
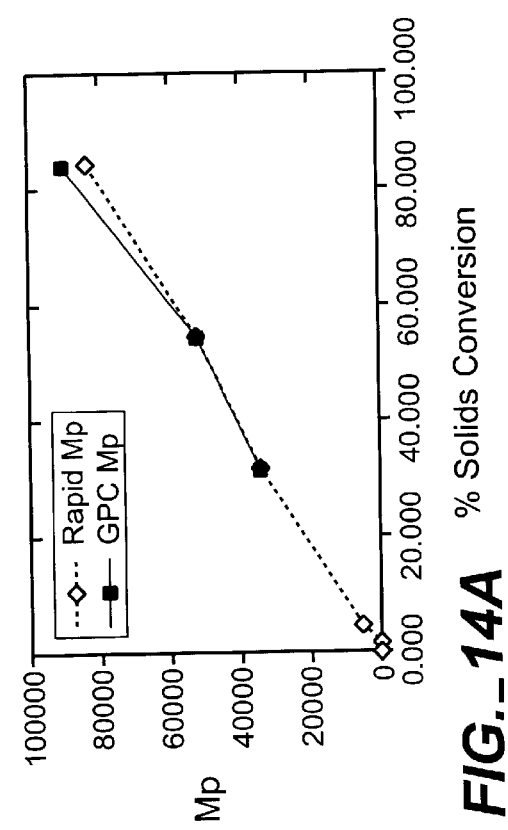
FIG._14A
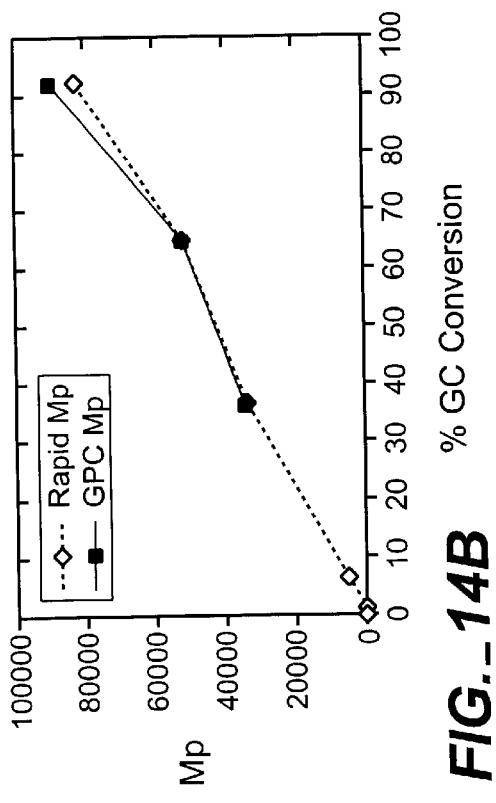
FIG._14B

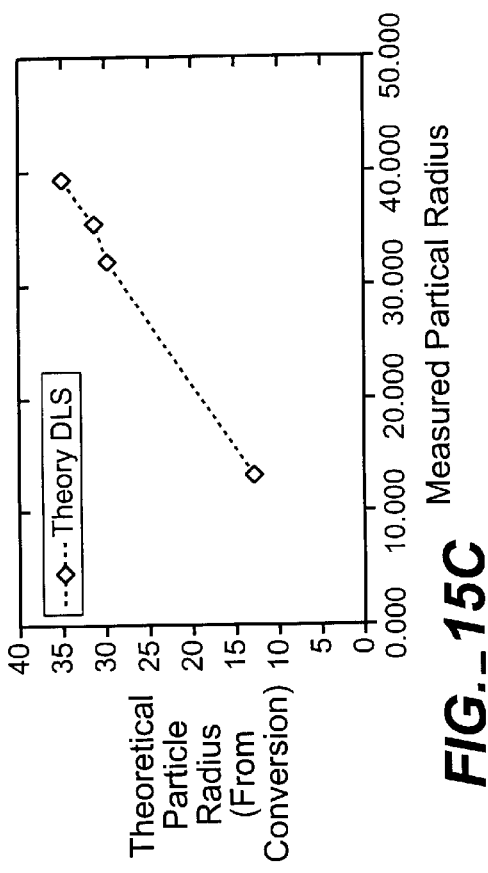
FIG._15C
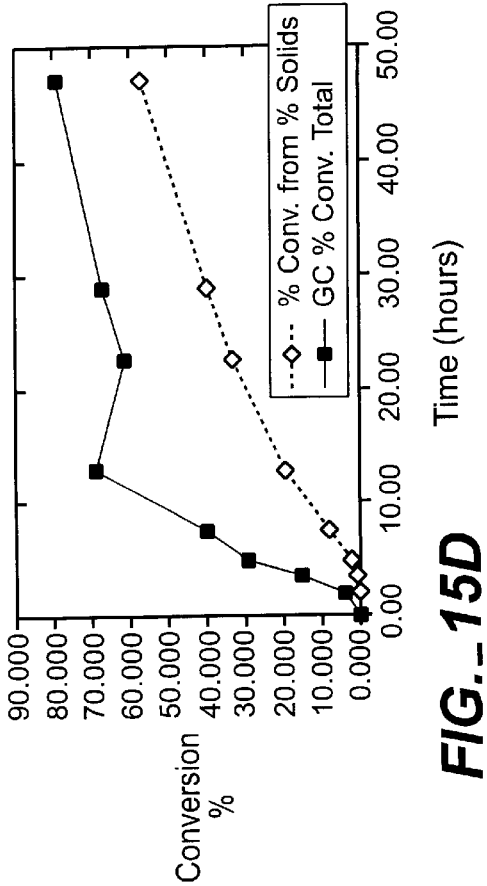
FIG._15D
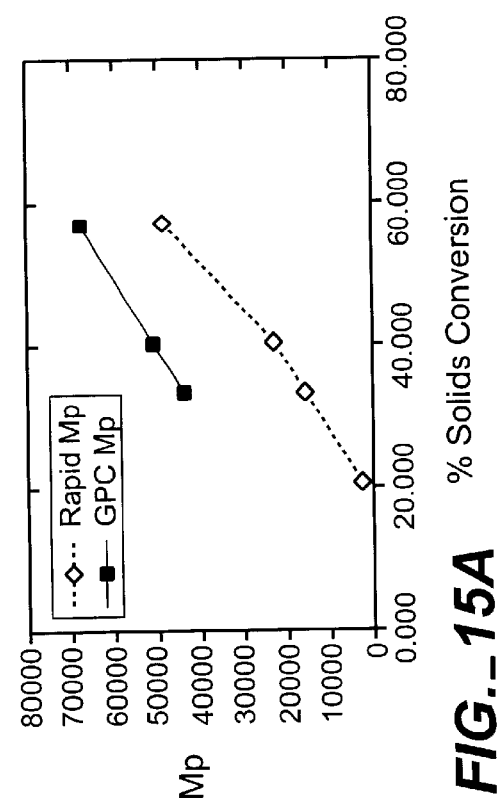
FIG._15A
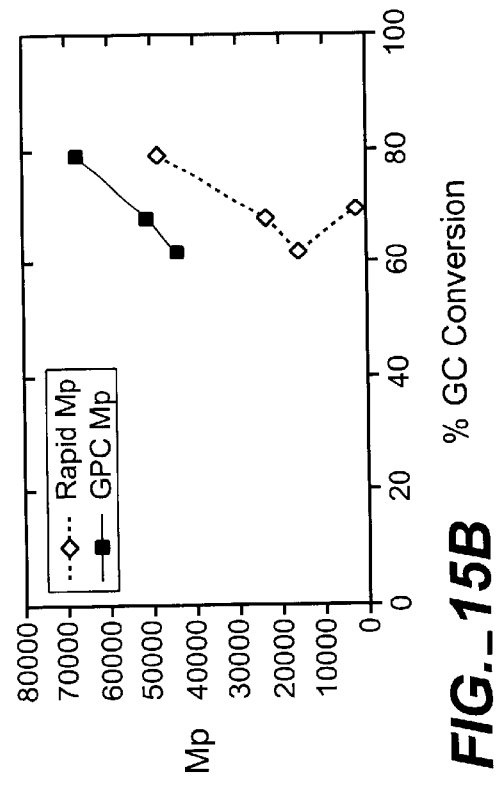
FIG._15B

CONTROLLED FREE RADICAL EMULSION AND WATER-BASED POLYMERIZATIONS AND SEEDED METHODOLOGIES

This application claims priority under 35 U.S.C. §119 to the commonly owned, co-pending U.S. Provisional Application No. 60/123,498, filed Mar. 9, 1999, which is incorporated herein by reference in its entirety. This application is also a continuation-in-part of each of U.S. patent applications Ser. Nos. 09/347,606, now abandoned, 09/347,607, 09/347,608 now abandoned, and 09/347,609, each of which was filed Jul. 2, 1999, and each of which is incorporated herein by reference in its entirety.

BACKGROUND OF THE INVENTION

1. Field of the Invention

This invention pertains to methods and compositions for controlled free radical polymerization in an emulsion or aqueous system using free radicals that provide control under a variety of conditions and with a wide variety of monomers. This invention also pertains to methods for seeding emulsion polymerizations. Furthermore, this invention also pertains to the polymers, copolymers and interpolymers that can be made with such a system.

2. Background Discussion

Controlled free radical polymerizations are generally known, which provide "living" type kinetics. These reactions may proceed by stable free radical or other mechanism. With the stable radical mechanism, it is generally believed that a stable free radical is used to reversibly cap the propagating polymer chain. There are several well-known nitroxide radicals (e.g., nitroxyls) that may be usefully employed in this methodology. See, e.g., U.S. Pat. Nos. 4,581,429, 5,322,912 and 5,401,804, each of which is incorporated herein by reference. The nitroxide radicals disclosed in these references have α-carbon atoms attached to the nitrogen that bear alkyl or aryl moieties (in addition to the oxygen). One of the most common nitroxide radicals is 2,2,6,6-tetramethyl-1-piperidinoxyl radical (TEMPO) and several groups have worked to make this and related radicals commercially viable control agents in a controlled, stable free radical polymerization scheme. See, e.g., WO 98/13392 and WO 98/07758, each of which is incorporated herein by reference. The drawback of TEMPO and related radicals has been the limitation on the monomers that can actually be polymerized. Styrene, substituted styrenes and copolymers including styrene have been prepared, but other desirable, commercially important monomers have not been polymerized in a controlled manner to desired molecular weights. German, et al, "Controlled Radical Polymerization in Emulsion," *Macromolecule*, 1997, 30, 324–326 and Claverie et al, "Nitroxide Mediated Living Radical Polymerization of Styrene in Emulsion," *Macromolecules*, 1998, 31, 4041–4044, both of which are incorporated herein by reference, have investigated TEMPO and other nitroxide radicals in emulsion; however, even in these studies styrene was the only monomer used and the polymerizations proceeded at high temperatures (125° C. or higher). TEMPO has proven to be limited in its usefulness. See also WO 98/30601, which is incorporated herein by reference.

Alternative nitroxide radicals were suggested by Grimaldi et al. bearing an electron withdrawing dialkoxyphosphonyl substituent and a hydrogen atom on the α-carbon atoms from the nitrogen. Grimaldi et al. "Synthesis and Applications to 'Living' Free Radical Polymerization of a New Class of Nitroxyl Radicals," Polymer Preprints, vol. 38, no. 1 (April 1997) and WO 96/24620, both of which is incorporated herein by reference. However, Grimaldi et al. did not focus on water-soluble systems or emulsions. See also EP 0891 986 A1, which is incorporated herein by reference.

More recently, Hawker et al., "Development of a Universal Alkoxyamine for 'Living' Free Radical Polymerizations," *J. Am. Chem. Soc.*, 1999, 121(16), pp. 3904–3920, which is incorporated herein by reference, discussed the general use of α-hydrido nitroxide radicals. Hawker et al. did not however considered emulsions or water-soluble systems. Also, many nitroxide radicals having a hydrogen atom on the a-carbon (sometimes referred herein to as an α-hydrido nitroxide radical) are known. See, e.g., Janzen et al., *J. Am. Chem. Soc.*, 91:16, pp. 4481–4490 (Jul. 30, 1969); Janzen et al., *J. Am. Chem. Soc.*, 1989, 111, 2206–2070; Janzen et al., *J. Am. Chem. Soc.*, 1986, 108, 6858–6863; and U.S. Pat. No. 3,422,144; each of which is incorporated herein by reference.

The use of water as a dispersing medium or solvent for control free radical polymerization is commercially important for several reasons. First, water is the safest medium from an environmental viewpoint, facilitating the manufacture of consumer products (such as paints or glues). Also, water is one of the least expensive media, providing an economical process. Moreover, the emulsion polymerization process is unique in that aqueous dispersions and emulsion that have direct utility in this for in various applications.

Also, seeded emulsion polymerizations are generally known in order to avoid or simplify the nucleation step. See, e.g., Poehlein et al, "Characterization of Water-Soluble Oligomer in Acrylic Acit-Styrene Emulsion Copolymerization," *J. Appl. Polym. Sci.*, vol. 50, pp. 2173–2183 (1993) or Ugelstad, et al., "A kinetic Investigation of the Emulsion Polymerization of Vinyl Chloride," *J. Polymer Sci., Part C*, no. 27, pp. 49–68 (1969), both of which are incorporated herein by reference. Seeded emulsions have also been attempted with TEMPO and TEMPO-like free radicals. See German et al. (cited above). The problem with these attempts is that the systems did not provide particle size control or emulsion quality for commercially important emulsions.

A need exists for a versatile, water-based controlled free radical polymerization process, which can use many types of initiators and can polymerize many types of monomers with a wide variety of process conditions.

SUMMARY OF THE INVENTION

This invention provides a method of free radically polymerizing a wide variety of monomers using water-soluble systems or emulsions, and thus provides access to a wide variety of resultant polymers that may be made from such processes. The methods, emulsions and polymers of this invention provide living-type free radical polymerizations, including the ability to re-initiate polymer chains and thus prepare unique polymers, including block copolymers. It is thus an object of this invention to provide a polymerization process that allows access to a wide variety of monomers that may be polymerized alone or together in emulsions or in an aqueous solution system. Moreover, the methods of this invention enable access to a full range of initiators, including fast and water-soluble initiators as well as slow and organic-soluble initiators that might otherwise appear to be less favorable for aqueous-based living-type polymerizations.

These and other benefits can be realized by an emulsion polymerization process that uses water, surfactant, initiator, at least one monomer and a control agent that comprises an α-hydrido nitroxide radical. The control agent can be added to the emulsion as a free radical or as an adduct of the initiator or initiator fragment attached to the control agent. The ratio of control agent to initiator can be in the range of from about 0.01:1 to about 4:1, but is generally most preferably close to 1:1 to provide a commercially reasonable balance between reaction time and living character. The ratio of initiator to monomer is important to the desired molecular weight of the resultant polymer and this ratio can be adjusted to a desired target molecular weight. The control agent may be water soluble in the emulsion process, but may also be relatively water-insoluble.

Another aspect of this invention is an aqueous-solution homogeneous polymerization process having living-type characteristics where water, a water soluble initiator, at least one water soluble monomer and a water soluble control agent that comprises an α-hydrido nitroxide radical are mixed together under polymerization conditions. This system forms water-soluble polymers, including block copolymers. Thus, it is an object of this invention to provide a system for the free radical polymerization of water-soluble polymers in a living type polymerization system using α-hydrido nitroxide radicals.

Yet another aspect of this invention is a seeding process for an emulsion polymerization. First, a fraction of the total monomer that is planned to be added to the polymerization reaction is first mixed with the initiator, control agent (or initiator-control agent adduct), water and surfactant. This combination is mixed and allowed to react for a predetermined period of time under predetermined polymerization conditions. The intent of this first stage is to allow the initiator to form "living" oligomers or seeds with the monomer in the system and the control agent. These are generally referred to herein as "loaded seeds," which are another aspect of this invention. Second and optionally subsequent stages provide for the addition of additional monomer, which can be the same or different from the monomer used in the first stage.

Another aspect of this invention includes the use of lower polymerization temperatures than are traditional with living free radical polymerizations. In some preferred embodiments of this invention, the temperature is about 110° C. or less. Another aspect of this invention is block copolymers having blocks with a weight average molecular weight of at least about 25,000.

Other aspects of this invention will be evident to those of skill in the art upon review of this specification, drawings and examples.

BRIEF DESCRIPTION OF THE DRAWINGS

FIGS. 1A and 1B are graphs showing molecular weight and conversion as a function of increasing nitroxide radical concentration for the TEMPO-controlled heterogeneous polymerization of styrene;

FIGS. 2A and 2B are graphs showing molecular weight and conversion as a function of increasing concentration of an α-hydrido nitroxide control agent for the heterogeneous polymerization of styrene.

FIGS. 3A–3E are graphs demonstrating the living kinetics achieved with this invention as well as control of molecular weight and conversion based concentration of an α-hydrido nitroxide radical control agent.

FIG. 4 is a bar graph showing molecular weight as a function of the concentration of an α-hydrido nitroxide radical control agent for both styrene polymers and styrene/butylacrylate copolymers.

FIG. 5 is a bar graph showing molecular weight as a function of the concentration of an α-hydrido nitroxide control agent for both butylmethacrylate polymers and styrene/butylmethacrylate copolymers.

FIG. 6 is a bar graph showing molecular weight as a function of the ratio of monomer to initiator for both styrene polymers and styrene/butylacrylate copolymers.

FIG. 7 is a bar graph illustrating the reinitiation of a living free radical polymerization after the addition of n-butylacrylate according to the invention.

FIG. 8 is a bar graph illustrating the reinitiation of a living free radical polymerization after the addition of acrylic acid according to the invention.

FIG. 9 is a bar graph illustrating the relationship between the overall molecular weight of the random copolymer and the amount of acrylic acid described in the example.

FIG. 10 illustrates a plot of an intensity-intensity auto-correlation function derived from dynamic light scattering measurements of a polymer emulsion prepared according to the invention.

FIG. 11 illustrates the results of a small angle X-ray scattering experiment on a copolymer produced according to the invention.

FIG. 12 is a reflection optical micrographs from copolymer emulsions synthesized according to the invention.

FIGS. 13A and 13B are transmission electron micrographs of a copolymer emulsion synthesized according to the invention.

FIGS. 14A, 14B, 14C and 14D are show the progression of molecular weight, conversion and particle size for the polymerization of the invention described in the example and wherein MP or Mp refers to peak molecular weight.

FIGS. 15A, 15B, 15C and 15D are show the progression of molecular weight, conversion and particle size for the polymerization of the invention described in the example and wherein MP or Mp refers to peak molecular weight.

DETAILED DESCRIPTION

The present invention is directed toward a polymerization process that uses a nitroxide radical control agent in an emulsion or water-soluble polymerization system. The control agent provides living type kinetics to the polymerization system.

As used herein, the phrase "characterized by the formula" is not intended to be limiting and is used in the same way that "comprising" is commonly used. The term "independently selected" is used herein to indicate that the R groups, e.g., $R^1$, $R^2$ and $R^3$ can be identical or different (e.g., $R^1$, $R^2$ and $R^3$ may all be substituted alkyls or $R^1$ and $R^2$ may be a substituted alkyl and $R^3$ may be an aryl, etc.). A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), hexyl, vinyl, n-butyl, tert-butyl, i-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to an alkyl as just described in which one or more hydrogen atom to any carbon of the alkyl is replaced by another group such as a halogen, aryl, substituted aryl, cycloalkyl, substituted cycloalkyl, and combinations thereof. Suitable substituted alkyls include, for example, benzyl, trifluoromethyl and the like.

The term "heteroalkyl" refers to an alkyl as described above in which one or more hydrogen atoms to any carbon of the alkyl is replaced by a heteroatom selected from the group consisting of N, O, P, B, S, Si, Se and Ge. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl, $Me_3SiOCH_2(CH_3)_2C$— and the like.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

"Substituted cycloalkyl" refers to cycloalkyl as just described including in which one or more hydrogen atom to any carbon of the cycloalkyl is replaced by another group such as a halogen, alkyl, substituted alkyl, aryl, substituted aryl, cycloalkyl, substituted cycloalkyl, heterocycloalkyl, substituted heterocycloalkyl, heteroaryl, substituted heteroaryl, alkoxy, aryloxy, boryl, phosphino, amino, silyl, thio, seleno and combinations thereof. Suitable substituted cycloalkyl radicals include, for example, 4-dimethylaminocyclohexyl, 4,5-dibromocyclohept-4-enyl, and the like.

The term "heterocycloalkyl" is used herein to refer to a cycloalkyl radical as described, but in which one or more or all carbon atoms of the saturated or unsaturated cyclic radical are replaced by a heteroatom such as nitrogen, phosphorous, oxygen, sulfur, silicon, germanium, selenium, or boron. Suitable heterocycloalkyls include, for example, piperazinyl, morpholinyl, tetrahydropyranyl, tetrahydrofuranyl, piperidinyl, pyrrolidinyl, oxazolinyl, and the like.

"Substituted heterocycloalkyl" refers to heterocycloalkyl as just described including in which one or more hydrogen atom to any atom of the heterocycloalkyl is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heterocycloalkyl radicals include, for example, N-methylpiperazinyl, 3-dimethylaminomorpholine, and the like.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone or oxygen as in diphenylether or nitrogen in diphenylamine. The aromatic ring(s) may include phenyl, naphthyl, biphenyl, diphenylether, diphenylamine and benzophenone among others. In particular embodiments, aryls have between 1 and 200 carbon atoms, between 1 and 50 carbon atoms or between 1 and 20 carbon atoms.

"Substituted aryl" refers to aryl as just described in which one or more hydrogen atom to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, amino, phosphino, alkoxy, amino, thio and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. Specific example of substituted aryls include perfluorophenyl, chlorophenyl, 3,5-dimethylphenyl, 2,6-diisopropylphenyl and the like.

The term "heteroaryl" as used herein refers to aromatic rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Substituted heteroaryl" refers to heteroaryl as just described including in which one or more hydrogen atoms to any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl radicals include, for example, 4-N,N-dimethylaminopyridine.

The term "alkoxy" is used herein to refer to the —$OZ^1$ radical, where $Z^1$ is selected from the group consisting of alkyl, substituted alkyl, cycloalkyl, substituted cycloalkyl, heterocycloalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the —$SiZ^1Z^2Z^3$ radical, where each of $Z^1$, $Z^2$, and $Z^3$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the —$BZ^1Z^2$ group, where each of $Z^1$ and $Z^2$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" refers to the group —$PZ^1Z^2$, where each of $Z^1$ and $Z^2$ is independently selected from the group consisting of hydrogen, substituted or unsubstituted alkyl, cycloalkyl, heterocycloalkyl, heterocyclic, aryl, heteroaryl, silyl, alkoxy, aryloxy, amino and combinations thereof.

The term "amino" is used herein to refer to the group —$NZ^1Z^2$, where each of $Z^1$ and $Z^2$ is independently selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "thio" is used herein to refer to the group —$SZ^1$, where $Z^1$ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to refer to the group —$SeZ^1$, where $Z^1$ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "saturated" refers to lack of double and triple bonds between atoms of a radical group such as ethyl, cyclohexyl, pyrrolidinyl, and the like.

The term "unsaturated" refers to the presence one or more double and triple bonds between atoms of a radical group such as vinyl, acetylenyl, oxazolinyl, cyclohexenyl, acetyl and the like. When a bond is drawn in a chemical formula that is not intended to represent a specific moiety or without a specific moiety or atom at the end, it is intended that standard chemical nomenclature is followed and the bond represents a methyl group at the appropriate position or a point of attachment.

Control Agents

In connection with the nitroxide radical mediated controlled free radical polymerization mechanism, many different types of control agents have been investigated. In some embodiments of this invention (e.g., in the loaded seed methods), the control agent may be of a type known in the art. Useful nitroxide radical control agents in these embodiments include those disclosed in, for example, U.S. Pat. Nos. 4,581,429, 5,322,912 and 5,401,804; PCT published applications WO 98/13392, WO 98/07758, WO 96/24620, WO 99/03894, WO 99/46261 and WO 99/00426; and Grimaldi et al. "Synthesis and Applications to 'Living' Free Radical Polymerization of a New Class of Nitroxyl Radicals," Polymer Preprints, vol. 38, no. 1 (April 1997) and Hawker et al, "Development of a Universal Alkoxyamine for 'Living' Free Radical Polymerizations," *J. Am. Chem. Soc.*, 1999, 121 (16), pp. 3904–3920; all of which are incorporated herein by reference. These patents, patent applications and publications disclose a wide variety of nitroxide radical control agents, which in general can characterized by the general formula •O—$NR_2$ wherein each R is independently selected from the group consisting of hydrocarbyl and substituted hydrocarbyl, and optionally the two R's may be joined together.

In some preferred embodiments of this invention, the free radical control agents may be characterized by the general formula:

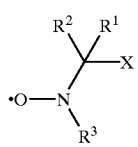

(I)

where each of $R^1$, $R^2$ and $R^3$ is independently selected from the group consisting of alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; and optionally, $R^1$ and $R^2$ are joined together in a ring structure; and also optionally $R^2$ and $R^3$ are joined together in a ring structure. X is a moiety that is capable of destabilizing the free radical, such as hydrogen. By "capable of destabilizing" it is meant that the X moiety allows the free radical to destabilize, decompose, be destroyed or otherwise removed from the reaction mechanism or be destabilized, decomposed, destroyed or removed from the reaction by the addition of a reagent. Generally, there is only destabilizing moiety on a carbon that is in the alpha (α) position. Thus, when X is hydrogen, the group chosen for $R^3$ should not include a hydrogen on the atom bonded to the nitrogen atom; such that $R^3$ is typically selected from the group consisting of tertiary alkyl, substituted tertiary alkyl, aryl, substituted aryl, tertiary cycloalkyl, substituted tertiary cycloalkyl, tertiary heteroalkyl, tertiary heterocycloalkyl, substituted tertiary heterocycloalkyl, heteroaryl, substituted heteroaryl, alkoxy, aryloxy and silyl. For the embodiments of this invention where it is desirable to enhance the water-solubility or transport of the control agent, it is preferred that one of the R groups ($R^1$, $R^2$ or $R^3$) includes a water-solublizing group, such as a sulfonate, sulfate, carboxylate, hydroxyl, amino, ammonium and the like. In other aqueous applications of this invention, it is preferred that the control agents have amphiphilic or hydrophobic substituents, to promote to control agent migration to interfaces, or to inhibit aqueous diffusion of the control agent.

Without wanting to be bound by any particular theory, it is believed that the concentration of free radical control agent, i.e., free nitroxide radical, is important to achieve a balance between controlling the polymerization reaction on one side and the reaction proceeding within a reasonably commercial time frame and with suitable monomer conversion percentages on the other side. In practical terms, the amount of control agent present in the polymerization reaction mixture should be enough to impart living type polymerization kinetics to the system, but not so much so that the polymerization reaction shuts down. Others have stated in connection with a TEMPO controlled system that rate of monomer conversion is controlled by the excess of nitroxide in the polymerization reaction mixture. See Georges et al., "The Stable Free-Radical Polymerization Process: Role of Excess Nitroxide," *Controlled Radical Polymerization* (ACS Symposium Series #685, 1998), pp. 170–179, incorporated herein by reference.

Thus, in this invention, it is preferred that the amount of free radical control agent as compared to "living" polymer chains remains substantially constant during the polymerization, with there being an excess of free radical control agent. Since a certain statistical percentage of "living" polymer control chains will terminate during the polymerization reaction, the free radical control agents useful in this preferred embodiment should have a mechanism available that destroys the free radical either through a decomposition reaction or a neutralization reaction. In this context, the phrase "decomposition reaction" refers to the free radical control agent reacting with itself or with another free radical control agent to yield a product or products that does not have a free radical. Similarly, in this context, the phrase "neutralization reaction" refers to the free radical control agent reacting with a reagent added to the polymerization reaction that removes or destroys the free radical associated with the control agent. In other words, the X moiety allows the free radical to destabilize itself (i.e., a decomposition reaction) so that the control agent has a limited lifetime, or is destabilized by the addition of a reagent (i.e., a neutralization reaction). The amount of the excess of stable free radical as compared to propagating chain ends depends on the exact polymerization conditions, monomers and nitroxide radicals, but typically is in the range of from about $10^{-4}$ to $10^{-8}$ moles per liter.

Another function of control agent structure in the heterogeneous aqueous polymerization mixtures of the invention is to influence the partitioning and concentration of control agent in the various phases of the mixture, such as the water phase, polymer phase, and or monomer phase, if present. Depending on the exact polymerization conditions, this partitioning can be important to the rates and living nature of polymerization at the intended locus of polymerization as well as other locations within the heterogeneous mixture.

In more specific embodiments, each $R^1$, $R^2$ and $R^3$ is independently selected from a group consisting of alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl and silyl. Specific examples of $R^1$, $R^2$ and $R^3$ are methyl, ethyl, propyl, butyl, cyclopentyl, cyclohexyl, cyclooctyl, phenyl, benzyl, trimethylsilyl, those specific moieties listed in the above definitions and the like. In alternative embodiments, $R^1$, $R^2$ or $R^3$ may include a water-solubilizing group, such as $SO_3G$, where G is Na, K and the like. In a preferred embodiment, $R^1$ is an aryl (such as phenyl), $R^2$ is an alkyl (such as isopropyl) and $R^3$ is either an alkyl or a heteroalkyl (such as tert-butyl or $Me_3SiOCH_2(CH_3)_2C$—). In an alternative preferred embodiment, $R^1$ is an aryl (such as phenyl), $R^2$ is a cycloalkyl (such as cyclohexyl or cyclopentyl) or a tertiary alkyl (such as tert-butyl) and $R^3$ is either a tertiary alkyl or a heteroalkyl (such as tert-butyl or $Me_3SiOCH_2(CH_3)_2C$—). In still another preferred embodiment, $R^1$ is a substituted alkyl (such as $NC(CH_3)_2C$—) and $R^2CNR^3$ form a cyclic ring structure.

In other embodiments, the free radical control agents may be characterized by the general formula:

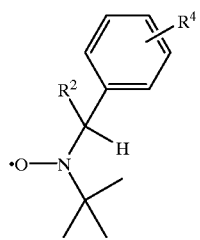

(II)

where each of $R^2$ and $R^4$ is independently selected from the group consisting of alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. There are from 0–5 substituent $R^4$ groups pending from the phenyl ring in general formula II, and when $R^4$ is not present, the phenyl ring has hydrogen atoms at the positions that would be occupied by the $R^4$ groups. Preferably, $R^2$ is an alkyl selected from the group consisting of methyl, ethyl and, especially, isopropyl. Also preferably, $R^4$ is not present. In other embodiments, $R^4$ includes a water-solubilizing group, such as $SO_3G$ (where G is H, Na, K and the like), $NH_2$, COOH, OH and the like.

Specific preferred nitroxide radicals include the following:

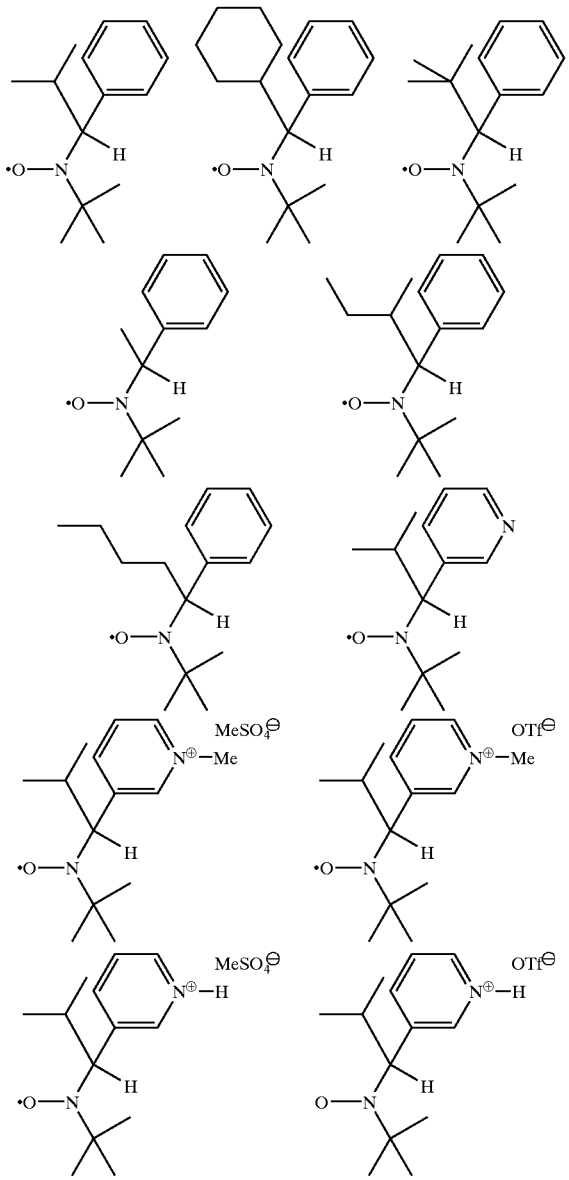

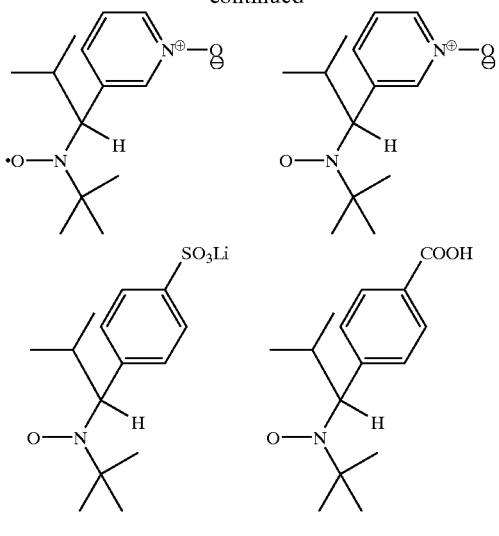

Initiators

Initiators useful in this invention include both water-soluble initiators and solvent-soluble or monomer-soluble initiators. Generally, the initiator must be capable of producing a radical (Y•) that initiates radical polymerization of a monomer and may attach to an end of the polymer.

In general, suitable radical initiators (and from which the Y• radical may be derived) can be selected from the group consisting of alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, azo compounds and halide compounds. Specific initiators include cumene hydroperoxide (CHP), t-butyl hydroperoxide (TBHP), t-butyl perbenzoate (TBPB), sodium carbonateperoxide, benzoyl peroxide (BPO), lauroyl peroxide (LPO), methylethylketone peroxide 45%, potasium persulfate, ammonium persulfate, 2,2-azobis(2,4-dimethyl-valeronitrile) (VAZO®-65), 1,1-azobis(cyclo-hexanecarbonitrile) (VAZO®-40), 2,2-azobis (N,N'-dimethyleneisobutyramidine) dihydrochloride (VAZO®-044), 2,2-azobis(2-amidino-propane) dihydrochloride (VAZO®-50) and 2,2-azobis(2-amido-propane) dihydrochloride. Redox pairs such a persulfate/sulfite and $Fe^{2+}$/peroxide are also useful.

In some embodiments of this invention, a preferred initiating radical is

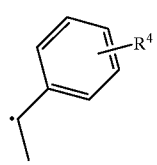

(III)

where $R^4$ is as defined above, with from 0–5 occurrences of $R^4$ on the phenyl ring. Further, in some preferred embodiments, the above-listed initiators or initiating radicals are substituted with a water-solubilizing group, such as $R^4$ is selected from the group consisting of —$SO_3G$ (where G is H, Na, K and the like), —COOH, —$NH_2$, —OH or substituted alkyl, where the substituent is selected from the group consisting of —$SO_3G$ (where G is H, Na, K and the like), —COOH, —$NH_2$, —OH, —COOG, —$NH_3X''$ (where G is Na, K and the like, and X'' is Cl, Br, $CH_3COO$, and the like).

Water transport properties are important for certain heterogeneous embodiments of this invention, including the loading of seeds (discussed in detail below). Thus, in those embodiments, the selected use of water-solubilizing groups on the initiator or initiating radical may be important, especially if water-solubilizing modifications to the nitroxide radical are not readily available. Also, water-solubilizing groups may also be important for the aqueous-solution embodiments of this invention.

Initiator-Control Agent Adducts

In some embodiments, the initiator can be combined with only the control agent to create an adduct, referred to herein as initiator-control agent adducts. The adduct can be characterized by the formula:

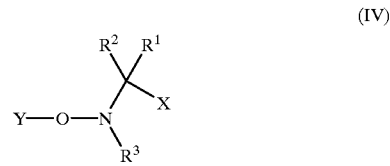

(IV)

where $R^1$, $R^2$, $R^3$, Y and X have the above meanings and preferences. In this context, Y is a residue capable of initiating free radical polymerization upon homolytic cleavage of the Y—O bond, including, for example, alkyl, substituted alkyl, alkoxy, substituted alkoxy, heteroalkyl, substituted heteroalkyl, aryl, and substituted aryl residues. Use of such adducts can eliminate concerns about the speed of initiation of polymer chains, effectively initiating all polymer chains at the same time upon addition of the adduct to the monomer under polymerization conditions. When the adduct is employed, the ratio of control agent to initiator can be adjusted by the addition of free radicals from any source, including, for example, additional free radical control agent (such as shown in connection with formula I, above), additional free radical initiators or radicals derived from other reactions.

When the preferred formulas for the control agent and the initiating radicals are combined, the preferred adducts of this invention may be characterized by any of the following general formulas:

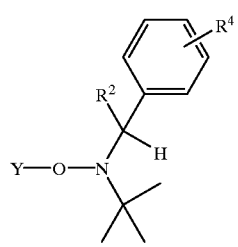

(V)

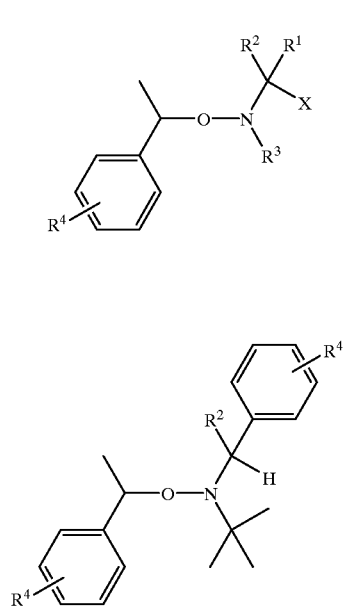

where $R^1$, $R^2$, $R^3$, $R^4$, Y and X have the above meanings and preferences.

The adducts may be prepared by methods known in the art, such as disclosed in WO 99/03894, which is incorporated herein by reference, or as shown in the examples herein. In another such embodiment, the control agent is generated in situ from the nitrone precursor, as is also discussed below and in WO 99/03894. In another embodiment, the adducts useful in this invention encompass compounds having monomer, oligomer or polymer disposed between the Y residue and the oxygen atom of the adduct, as shown in formula VIII, below. Thus, embodiments including compounds of the structure shown in formula VIII are within the definition of "adduct" as that term is applied to the invention. The α-hydrido adduct used in the examples was prepared according to Hawker et al, "Development of a Universal Alkoxyamine for 'Living' Free Radical Polymerizations," *J. Am. Chem. Soc.,* 1999, 121(16), pp. 3904–3920, previously incorporated herein by reference. Additionally, methods of making adducts are discussed in detail in the example section, below.

Specific initiator-control agent adducts that may be used include:

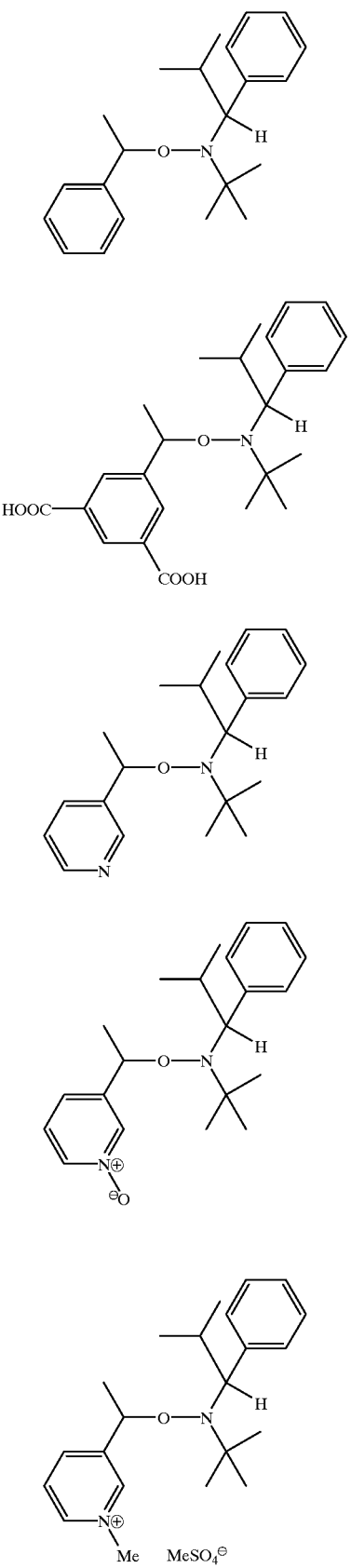

-continued

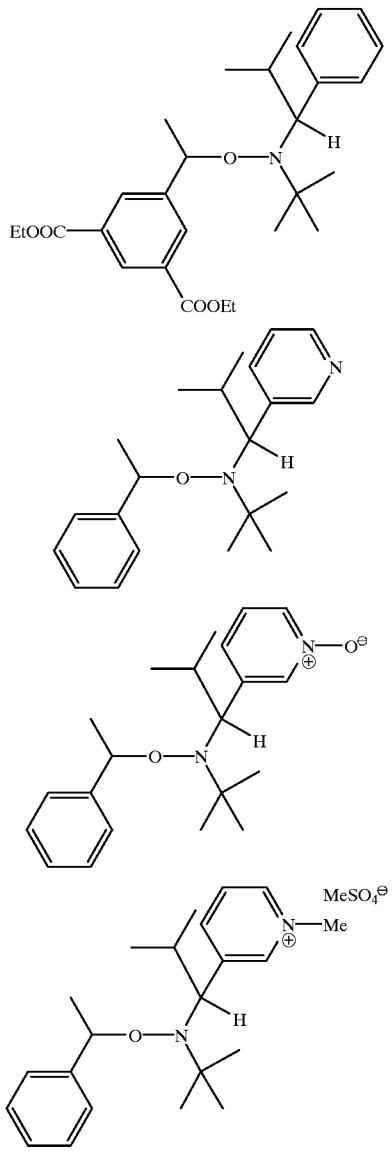

As discussed in various places throughout this specification, the hydrophilicity of the control agent, initiator and/or initiator-control agent adduct can be tuned to account for the desired water-transportability or water-dispersability or water-solubility. Generally, tuning the hydrophilicity comprises the use of one or more hydrophilic functional groups attached to a desired portion of the control agent, initiator and/or initiator-control agent adduct. With regard to adducts, this can be shown in the following general formula:

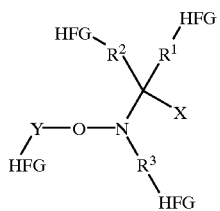

where $R^1$, $R^2$, $R^3$, Y and X have the above meanings and preferences and HFG refers to a hydrophilic functional group. HFG is generally selected from the group consisting of sulfonic acid salts, pyridinium moieties, ammonium salts and carboxylates. Other HFG groups include, —$NH_2$ and —OH. In some embodiments, the sulfonate hydrophilic functional groups are preferred (e.g., —$SO_3G$ (where G is H, Na, K and the like)) because they are more resistant to hydrolysis, particularly in the lower temperatures suggested by the polymerization conditions of this invention. Thus, each HFG may be selected independently from the group consisting of —$SO_3G$ (where G is H, Na, K and the like), —COOH, —$NH_2$, —OH or substituted alkyl, where the substituent is selected from the group consisting of —$SO_3G$ (where G is H, Na, K and the like), —COOH, —$NH_2$, —OH, —COOG, —$NH_3X''$ (where G is Na, K and the like, and X'' is Cl, Br, $CH_3COO$, and the like).

Monomers

Monomers that may be polymerized using the methods of this invention (and from which M may be derived) include at least one monomer selected from the group consisting of styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate and combinations thereof. Functionalized versions of these monomers may also be used. Specific monomers or comonomers that may be used in this invention and from which M is derivable include methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, α-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, vinyl benzoic acid (all isomers), diethylaminostyrene (all isomers), α-methylvinyl benzoic acid (all isomers), diethylamino α-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, butadiene, isoprene, chloroprene, ethylene, vinyl acetate, 2-(2-oxo-1-imidazolidinyl)ethyl 2-methyl-2-propenoate, 1-[2-[[2-hydroxy-3-(2-propyl)propyl)]amino]ethyl]-2-imidazolidinone, W-vinyl pyrrolidone, N-vinyl imidazole, crotonic acid, vinyl sulfonic acid, and combinations thereof.

Depending on the embodiment of the invention being practiced, these monomers may be referred to as the first polymerizable monomer, the second polymerizable monomer, at least one monomer, etc.

Surfactants

Surfactants can be useful in the processes and composition of this invention. Suitable surfactants include any species or mixture of species capable of stabilizing colloidal emulsions. Generally surfactants are amphiphilic molecules comprising both hydrophobic and hydrophilic regions, which are capable of adsorbing to surfaces. Surfactants may be small molecules or polymers, micelle forming or non-micelle forming and may be anionic, cationic, zwitterionic or nonionic. In some embodiments, it may be desirable to use mixtures of surfactants, for example to enhance particle stability or control particle formation. Surfactants can play an important role in determining particle size, particle distribution, particle formation and the stability of the resulting polymer emulsion, which are factors that those of skill in the art typically consider when choosing a surfactant for any specific embodiment. Economic factors may also be considered in choosing surfactants for a particular application. Typical amounts of surfactants range from about 0.01 to about 200% by weight relative to the monomer, with a more preferred range being from about 0.1 to about 5% by weight and more specifically preferred being from about 0.5 to about 3% by weight.

Suitable surfactants include anionic, small molecule surfactants including substituted or unsubstituted hydrocarbyl sulfates, sulfonates, carboxylates, phosphonates and phosphates, having between 6 and 30 carbon atoms per anionic functional group. When the hydrocarbyl group is substituted, it may have one or more hydrogen or carbon atoms replaced with another atom selected from the group consisting of N, S, O, Si, F, Cl, Br and I. The hydrocarbyl may also have one or more hydrogen or carbon atom replaced with a functionality such as a keto, ester, amide, ether, thioether and the like. Specific examples of anionic, non-polymeric surfactants include sodium dodecyl sulfate, sodium dodecylbenzene sulfonate, $C_{14}$–$C_{16}$ α-olefin sulfonate, oleoyl methyltaurine, alkyl sulfosuccinate, sodium stearate, alkyl substituted disulfonated diphenyloxide and nonylphenoxy oligo(ethylene glycol) sulfate. Ionic polymers can be used, including polyethyleneimine, polyacrylic acid, carboxymethyl cellulose and the like. Suitable cationic surfactants include cetyltrimethyl ammonium bromide, N-methyl(4-dodecylpyridinium bromide). Suitable nonionic surfactants include random and block copolymers of polyvinyl alcohol, polyvinylacteate co-polyvinyl alcohol, polyethyleneoxide co-buyleneoxide, polyethyleneoxide-co-propyleneoxide, polyalkyl-glycidol, substituted polyalkyl-glycidol. In other embodiments, useful surfactants include, for example, ethoxylated mono-, di- and trialkylphenols (degree of ethoxylation: 3 to 100, alkyl radical: $C_4$ to $C_{12}$), ethoxylated fatty alcohols (degree of ethoxylation: 3 to 100, preferably 6 to 50, alkyl radical: $C_6$ to $C_{20}$) and alkali metal and ammonium salts of alkylsulfates (alkyl radical: $C_8$ to $C_{18}$), of sulfuric half-esters of ethoxylated alkanols (degree of ethoxylation: 1 to 70, in particular 2 to 10, alkyl radical: $C_{10}$ to $C_{18}$) and of ethoxylated alkylphenols (degree of ethoxylation: 3 to 100, preferably 6 to 50, alkyl radical: $C_4$ to $C_{18}$) and alkali metal and ammonium salts of alkanesulfonic acids (alkyl radical: $C_{10}$ to $C_{18}$) and of alkylarylsulfonic acids (alkyl radical: $C_9$ to $C_{18}$). Further suitable surfactants, such as sulfosuccinates, are described in Houben-Weyl, Methoden der organischen Chemie, Volume XIV/1, Makromolekulare Stoffe, Georg-Thieme Verlag, Stuttgart, 1961, pages 192 to 208. Alternative surfactants include functional monomers, polymerizable surfactants and water-soluble surface-active polymers, including block copolymers. Specific examples include polyvinyl alcohols, cellulose derivatives or vinylpyrrolidone-containing copolymers. A detailed description of further suitable protective colloids is given in Houben-Weyl, Methoden der organischen Chemie, Volume XIV/1, Makromolekulare Stoffe, Georg-Thieme-Verlag, Stuttgart, 1961, pages 411 to 420. Currently commercially available surfactants that are useful in this invention are listed below in Table 1.

TABLE 1

| Trade Name | Supplier | Contents |
| --- | --- | --- |
| Ionics | | |
| Abex VA-50 | Rhodia | 46%; 1:1 mix of anionic and ethoxylated octyl phenol |
| Abex 2020 | Rhodia | Anionic/non-ionic mix (APE free), 30% |
| Abex 2030 | Rhodia | Anionic/non-ionic mix (APE free), 30% |
| Abex 18-S | Rhodia | Na Ether Sulfates; APE-free, 35% |
| Abex 12-S | Rhodia | Na Ether Sulfates; APE-free, 30% |
| Aerosol OT | Sigma | [(Bis-2-ethylhexyl)sodium sulfosuccinate, $C_{20}H_{37}O_7S.Na$, $M_w$ 444.6, 10% |
| Aerosol 22 | Sigma | [(Bis-2-ethylhexyl)sodium sulfosuccinate, $C_{20}H_{37}O_7S.Na$, $M_w$ 444.6, neat d = 1.12 |
| Calfax DB-45 | Pilot Chemical | $C_{12}$ (branched) Sodium diphenyloxide disulfonate, 45% |
| Calfax 16L-35 | Pilot Chemical | $C_{16}$ (linear) Sodium diphenyloxide disulfonate, 35% |
| Calimulse L-30 | Pilot Chemical | Sodium linear alkyl benzene sulfonate 30% |
| Calimulse EM-30 | Pilot Chemical | Sodium branched dodecyl benzene sulfonate 30% |
| Calsoft F-90 | Pilot Chemical | Sodium linear alkyl benzene sulfonate, solid, 90+% |
| Dowfax C6L | Dow | Disulfonated diphenyloxide with $C_6$ backbone |
| Dowfax C10L | Dow | Disulfonated diphenyloxide with $C_{10}$ backbone |
| Dowfax 8390 | Dow | Disulfonated diphenyloxide with $C_{16}$ backbone, 45% |

TABLE 1-continued

| Trade Name | Supplier | Contents |
| --- | --- | --- |
| Emulgator 825 | BASF | anionic/non-ionic mix |
| Emulgator 825-S | BASF | anionic/non-ionic mix |
| Rhodacal A-246/L | Rhodia | sodium alpha C14—C16 olefin sulfonate (38–41%) |
| Rhodacal DS-4 | Rhodia | sodium dodecyl benzene sulfonate 23% |
| SDS | Aldrich | sodium dodecyl sulfate |
| SDBS | Aldrich | sodium dodecyl benzene sulfonate 90% |
| Triton QS-30 | Union Carbide | 90%, gel like |
| Triton X-200 | Union Carbide | 28% aq dispersion |
| Atphos 3232 | ICI | Polyoxyethylene phosphate ester |
| Atphos 3226 | ICI | anionic sfac, phosphoric acid |
| Atphos 3202 | ICI | NonylPE n = 6, acid form, 100% |
| Nonionics | | |
| Abex 2545 | Rhodia | |
| Abex 2535 | Rhodia | |
| Dynol 604 | Air Products | Ethoxylated acetylenic diols, 100% |
| Igepal CO-210 | Aldrich | APE ($C_9H_{19}$—$C_6H_4$—$(OCH_2CH_2)_2OH$) 100% |
| Igepal CO-520 | Aldrich | APE ($C_9H_{19}$—$C_6H_4$—$(OCH_2CH_2)_5OH$) 100% |
| Igepal CA-897 | Rhodia | APE (octylphenol ethoxylate) 70%, n = 40 |
| Igepal CO-897 | Rhodia | APE (nonylphenol ethoxylate) 70% n = 40 |
| Pluronic F38 | BASF | EO-PO-EO block, average $M_w$ 4700 HLB 31 |
| Pluronic F98 | BASF | EO-PO-EO block, average $M_w$ 13K, HLB 28 |
| Pluronic P65 | BASF | EO-PO-EO block, average $M_w$ 3400 HLB 17 |
| Surfynol 104 PA | Air Products | 50% in isopropyl alcohol, 50% 2,4,7,9-tetramethyl-5-decyne-4,7,-diol |
| Surfynol 104 PG-50 | Air Products | 50% in propylene glycol, 50% 2,4,7,9-tetramethyl-5-decyne-4,7,-diol |
| Surfynol DF-58 | Air Products | silicone-based |
| Surfynol 440 | Air Products | Surfynol 104 with ethylene oxide chains, more hydrophilic, 100% |
| Surfynol 465 | Air Products | Surfynol 104 with ethylene oxide chains, more hydrophobic, 100% |
| Triton X-100 | Union Carbide | t-octylphenoxy-polyethoxyethanol (n = 9.5), 100% |
| Triton X-405 | Union Carbide | t-octylphenoxy-polyethoxyethanol, 70% |

Accelerators

Optionally, an accelerator may be added to the polymerization system. Suitable accelerators useful in this invention include alkylating and acylating agents, Lewis Acids, ketones, aldehydes, anhydrides, acid esters, imides, oxidants and reducing agents. Specific accelerators include acetic acid, acetic anhydride, camphor sulfonic acid, acetole (1-hydroxyacetone) and the like. Other accelerators useful herein are recited in Hawker et al., "Development of a New Class of Rate-Accelerating Additives for Nitroxide-Mediated 'Living' Free Radical Polymerization," Tetrahedron, Vol. 53, No. 45, pp. 15225–15236 (1997), which is incorporated herein by reference. A second, related, method for increasing the rate of polymerization in these living-type systems, it has been found, is to lower the pH of the polymerization system by the addition of an acid to the system. Any compatible acid may be used including organic acids, inorganic acids, Lewis acids and Bronsted acids. Preferred acids include acetic acid, sulfuric acid, methane sulfonic acid, p-toluene sulfonic acid, and polymerizable acids such as acrylic acid, methacrylic acid, and 2-acrylamido-2-methylpropanesulfonic acid (AMPS). The pH can be lowered to about 5 or below for an accelerated polymerization reaction, depending on the exact nitroxide radical used. In other embodiments, the pH is about 4 or lower or about 3.5 or lower.

Polymerization Systems

The polymerization systems of this invention are combinations or mixtures of components, which include water, control agent, initiating radical and at least one monomer. The addition of a surfactant to the polymerization system is optional, but typically preferred for the emulsion embodiments of this invention. In embodiments that employ the adducts of this invention, the adduct can be thought of as combining the structures and functions of the initiating radical and control agent. The polymerization system is subjected to polymerization conditions to effect polymerization of the at least one monomer. At least one monomer is added to the polymerization system. For random copolymers or higher order interpolymers, two or more monomers may be added to the polymerization system at the same time. For block copolymers, the monomers are typically added in a desired sequence in order to grow the desired block. For the emulsion polymerization systems, the polymerization system is considered to be the starting components, which are subjected to the polymerization conditions. The products of such polymerization systems are the emulsions themselves or the polymers, after drying. For the aqueous solution polymerizations, the polymerization system is typically the combination or mixture of water, control agent, initiating radical and at least one monomer, where the components of the polymerization system are soluble to some degree in water. The amount of solubility depends on the exact polymerization system chosen.

The ratios of components (e.g., initiators, surfactants, monomers, control agents, etc.) in the polymerization system may be important and can vary widely depending on the particular embodiment being practiced. The ratio of monomer to initiator can be used to determine the molecular weight of polymers produced using the controlled heterogeneous free radical polymerization processes of the invention. According to these processes, the number average molecular weight of the resulting polymers depends linearly on the number of free radical chains in the polymerization and the mass of monomer. Assuming every initiator initiates one chain, the selection of a monomer to initiator ratio provides an opportunity to "dial in" to a desired molecular weight (or degree of polymerization) (taking into account the ratio of chains formed to initiating fragments formed by the particular initiator in question). Typically, however, initiator efficiency ranges from about 1 to about 0.1 depending on the exact chemistry in the polymerization system (e.g., initiator or monomer chosen) and this efficiency should be taken into account when dialing in the desired molecular weight.

In typical embodiments, the monomer to initiator ratio may be in the range of from about 10:1 to about 10,000:1, more preferably the range of from about 50:1 to about 10,000:1 and most preferably the range of from about 100:1 to about 5000:1. Another ratio that may be controlled is the ratio of equivalents of initiator to free radical control agent, (with the assumption that the amount of initiator is approximately equivalent to the number of initiating radicals produced), which is typically in the range of from about 1:0.1 to about 1:4, more preferably the range of from about 1:0.3 to about 1:2 and most preferably the range of from about 1:0.4 to about 1: 1.6. When an accelerator is present the ratio of free radical control agent to accelerator is typically in the range of from about 1:0.1 to about 1:4, more preferably the range of from about 1:0.3 to about 1:2 and most preferably the range of from about 1:0.4 to about 1:1.6. The surfactant to monomer ratio may be controlled and is typically in the range of from about 0.0001 to about 2:1, more preferably the range of from about 0.001:1 to about 0.05:1 and most preferably the range of from about 0.001:1 to about 0.02:1 (although for some emulsions there may be no surfactant added at all where other reaction components perform that function). Once emulsions are formed, the percent solids may be in the range of from 0.001% to about 90% by volume. In some preferred applications, the novel aqueous polymer emulsions are produced with a solids content of =40, advantageously =50%, by volume, based on the total aqueous polymer emulsion. The useful solids content for other applications is from 0.5 to 95% by volume. The preparation of the novel aqueous polymer emulsions is carried out according to the product by process definition of the subject according to the invention, as stated at the outset, i.e., by the free radical aqueous emulsion polymerization method in the presence of dispersants and free radical polymerization initiators. The ratio of the aqueous phase to the total amount of the monomers used in both stages is chosen according to the desired solids content of the aqueous polymer emulsion to be prepared.

Polymerization conditions include the ratio of components, temperature, pressure, atmosphere, reaction time and other conditions generally known to those of skill in the art. Polymerization temperature can range from about −40° C. to about 300° C., preferably between about 0° C. and about 200° C., more preferably between about 25° C. and about 150° C., and most preferably between about 40° C. and about 110° C. Alternatively, the temperature may be between about −40° C. and 250° C. In other preferred embodiments, the temperature of the polymerization system is controlled to a temperature of less than or equal to about 110° C., more preferably less than or equal to about 100° C., even more preferably less than or equal to about 95° C. and for some embodiments less than or equal to about 90° C. This lower temperature embodiment is may possible, in part, due to the preferred nitroxide radical control agents having a destabilizing mechanism available, as discussed in detail above. More preferred is a polymerization temperature below about 100° C. and even more preferable below about 95° C. Polymerization conditions also include a pressure between about ambient pressure up to about 100 atmospheres. The atmosphere above the emulsion may also be one of the polymerization conditions, and the atmosphere may be air, nitrogen, argon or another suitable atmosphere. Polymerization conditions also include the time for reaction, which may be from about 0.5 hours to about 72 hours, preferably in the range of from about 1 hour to about 24 hours, more preferably in the range of from about 2 hours to about 12 hours.

Emulsion Polymerization Systems

In the broadest sense, an emulsion polymerization is any heterogeneous polymerization in an aqueous environment. Typically, these systems produce particles of polymer as product. Those skilled in the art recognize many variants of these polymerizations, with typical classifications distinguishing between polymerizations occurring in true emulsions, micro emulsions, mini emulsions, suspensions and dispersions. These processes are generally distinguished by differences in process, components or results, with specific factors including the presence, amount and type of surfactant required; presence, amount and type of intitiator; type and amount of monomer, including monomer solubility; polymerization kinetics; temperature; order of addition of the components, including the timing of addition of the components (e.g., monomer); solubility of the polymeric product; agitation; presence of cosolvents; resulting particle size; particle stability in the polymerization system toward coagulation or sedimentation; and other factors known to those skilled in the art.

The systems of the invention may not fall completely into any of the traditional definitions typically applied by those skilled in the art (e.g., true emulsions vs. micro emulsions). These systems may fall between the traditional definitions, while having properties characteristic of one or many traditionally-classified systems. Accordingly, the polymerizations of the invention can be considered to encompass traditional (or true) emulsion polymerizations, micro and mini emulsions as well as to suspension and dispersion polymerizations. Characteristics that can be used to distinguish these heterogeneous polymerization systems are set out in Table 2, below.

TABLE 2

| Property | Traditional Emulsion | Mini Emulsion | Micro Emulsion | Suspension | Dispersion |
| --- | --- | --- | --- | --- | --- |
| Locus of polymerization | Particles | Droplets | Particles | droplets | Water |
| Distribution of monomer | Droplets/ Particles | Droplets | Particles | droplets | Droplets/ water |

TABLE 2-continued

| Property | Traditional Emulsion | Mini Emulsion | Micro Emulsion | Suspension | Dispersion |
|---|---|---|---|---|---|
| Distribution of polymer | Particles | Droplets | Particles | droplets | Particles |
| Aqueous solubility of monomer | Moderate to high | low to moderate | Moderate | low to moderate | High |
| Importance of agitation | Moderate to low | high (at start) | Low | high | High |
| Typical resulting particle size | 10 to 200 nm | 50 to 500 nm | 10 to 100 nm | 500 to 5000 nm | 500 to 5000 nm |
| Typical particle size distribution | Narrow | Broad | Narrow | broad | Broad |
| Typical amount of surfactant (relative to monomer) | 0 to 5% | 0.1 to 10% | ≈100% | 0 to 5% | 0 to 5% |
| Thermodynamic stability of particles before polymerization | not stable | not stable | Stable | not stable | Not stable |
| Typical maximum solids content | 50% | 20% | <10% | 40 to 50% | 40 to 50% |

Some of these ranges are subjective and extremes may often only be obtained in exceptional circumstances. Terms such as low, medium and high are subjective, and are intended to illustrate differences in the classifications known to those skilled in the art. The processes of the invention are distinguished as discussed herein.

One specifically preferred embodiment of the invention is a controlled heterogenous polymerization reaction in an emulsion characterized by particle sizes ranging from 10 to 150 nm, and preferably from 15 to 100 nm or from 20 to 70 nm in hydrodynamic radius. Polymerizations of this embodiment may have process parameters similar to those discussed above for "traditional" or "true" emulsion polymerizations. These emulsions are stable (on the order of many months with no observed coagulation or sedimentation, yet are prepared using surfactant in amounts less than 2% by weight to monomer. These emulsions feature a uniform distribution of particle sizes (nonuniformity of the polymer particle radius distribution— e.g., R.M.S. variation in average polymer particle radius of less than about 50%).

The controlled particle sizes that characterize the controlled polymer emulsions of some embodiments of the invention provide a number of benefits in many applications. The living nature of the polymerization processes of the invention allow for novel means for controlling particle size and distribution of the resulting polymer emulsions. Emulsions of smaller particles are generally very stable and have useful process advantages such as faster reaction kinetics and more scalable and reproducible preparations. Such emulsions have useful optical properties (e.g., lower turbidity), high viscosity, greater surface area and coalesce to form more uniform or thinner films, all of which may be advantageous in typical applications such as adhesives, dispersants, coatings and separation media. In other embodiments directed to different applications, larger particles may be desirable and can be obtained using the heterogeneous aqueous free radical polymerizations of the invention. Desirable properties of large-particle emulsions include opacity, low viscosity, and ease of polymer isolation. Emulsions with uniform or broad particle size distribution can result from processes of the invention, with various advantages of particle size distribution known to those skilled in the art. For example, broad particle size distribution may result from properly chosen polymerization conditions, or may be obtained by blending particles of narrow size distribution obtained from several different polymerizations.

Unless otherwise specified, polydispersity index or PDI refers to the ratio of mean/median for a distribution, or more specifically for the case of molecular weight measurements, polydispersity index is known in the art as $M_w/M_N$, where $M_w$ is the weight average molecular weight and $M_N$ is the number average molecular weight of a polymer sample. Values of PDI in this specification range from 1.0 and higher, with values near 1 representing relatively monodisperse samples. With regard to dynamic light scattering used for particle size determinations, the common use of second cumulant analyses to fit the autocorrelation function leads to use of the term "second cumulant analysis PDI," which is the PDI describe in the below referenced software and manuals. The absolute value of the "second cumulant analysis PDI" ranges from zero and higher, preferably from about 0 to about 0.3 for relatively monodisperse particle size distributions. This is generally known in the art of dynamic light scattering for particle size determinations. Such analyses were performed herein using into autocorrelator equipment for computers, such as that supplied by ALV GmbH, Langen, Germany, using ALV 5000/E Correlator Board, and the software and manuals used therewith, which is incorporated herein by reference.

The use of nitroxide control agents under emulsion conditions offers other benefits associated with living kinetics (e.g., linear increase in molecular weight as a function of conversion). The controlled free radical emulsion polymerizations of the invention provide a high degree of control over molecular weight, especially at high molecular weight, (as high as ≧50,000, or even ≧100,000), often with narrow molecular weight distribution (polydispersity ($M_w/M_N$) generally less than 2 and preferably between 1.1 and 1.8, also below 1.4). Likewise, nitroxide control agents provide significant control of particle sizes. While typical particle sizes for uncontrolled radical emulsion polymerizations range from 50 to about 200 nm depending on the amount of monomer and surfactant, polymerizations of the invention have been shown to provide emulsions with smaller particle size, under similar condition of surfactant and monomer concentration. For example, uncontrolled emulsion polymerizations of styrene (1% surfactant, 20% solids and target $M_w$ of 100,000) yield particle sizes that range from about 50 to about 75 nm radius. By contrast, the emulsion polymerization processes of this invention with loaded seed can readily produce emulsion polymers with particle sizes less than 40 nm.

In the emulsion polymerization process of this invention, the control agent in radical form is combined with water, surfactant, initiator (or initiating radical), at least one monomer and optionally an accelerator and/or a reagent to react with the control agent under polymerization conditions. Emulsion polymerization conditions include those discussed above, but most preferably are at a temperature below about 95° C.

Seeded Emulsion Polymerization Systems

The use of seeds in the controlled emulsion polymerization systems of this invention may be an important method for controlling the particle nucleation process, number of particles formed, particle size of the final emulsion, and minimizing the amount of coagulum formed in the polymerization. In particular, the use of a seed helps to better control the nucleation step by separating it from the controlled radical polymerization process and thus helps control the final particle size using convention radical emulsion processes. With polymerization systems that have living kinetics, this invention provides methods for both achieving a desired particle size with a desired number of chains per particle and a desired molecular weight of those chains, factors that are generally difficult to control separately in conventional radical polymerization processes. In conventional radical emulsion polymerization, surfactant micelles typically provide a locus for polymerization and particle nucleation, because of the rapid growth of the first few polymerizing chains introduced into the system. However, with the slower chain-growth as compared to uncontrolled polymerizations that are experienced in controlled radical processes, and in order to arrive at typical desired molecular weights (i.e., 20,000–500,000) and typical particle sizes (i.e, 25–75 nm radius), it is generally necessary to nucleate particles that have between 300 and 30,000 polymer chains per particle, with each chain requiring at least one control agent. This is difficult to achieve with typical small-molecule surfactant micelles that are usually in the range of 1–2.5 nm in radius, and comprise typically between 50 and 300 surfactant molecules. The use of loaded seed particles that are larger than micelles but smaller than typical final emulsion particles as described in this invention allows for the localization of the desired number of chains per particle, and for particle volume growth to result in final emulsions of the desired size as the chains grow to the target molecular weight, which is determined by the initiator to monomer ratio.

This invention is directed toward an emulsion process for polymerization that allows the effective use of organic or water soluble initiators and otherwise slow initiators in an emulsion polymerization process that has living type kinetics. Typically, initiation in a living type polymerization system is intended to be as fast as possible in an effort to have most of the polymer chains begin propagating at about the same time. If an initiator is slow in its creation of radicals, then new propagating chains may be created much later in the process than other chains, leading to broadened molecular weight distributions (or polydispersities or weight average molecular weight over number average molecular weight or $M_w/M_n$), which may be desirable in some embodiments. Also, organic soluble initiators are not typically used in an emulsion polymerization mixture because they may reside in the monomer pools (or droplets), which may lead to loss of control, large particle sizes, unstable emulsions, undesirable polymerization in the monomer pools (and related issues, such as bimodal or multi-modal polydispersities). As used herein a "seed" means a polymer particle that maintains its integrity in water. Those of skill in the art may consider the seed to be kinetically "stable" in water, which typically implies some amount of surfactant, but the polymer in the seed may be chosen so as eliminate the surfactant. Typically a seed has a hydrodynamic radius that is less than or equal to about 25 nanometers (nm), preferably less than or equal to about 15 nm and in some applications may be less than or equal to about 7 nm. The hydrodynamic radius is measured in a method known to those of skill in the art, such as with dynamic light scattering or cryogenic transmission electron microscopy. As discussed in detail below, the seed typically comprises polymer chains that cannot be further grown or propagated in a polymerization system and/or "living" oligomers, as well as or alternatively other components. In those embodiments where one or more components of the seed may be further grown or propagated in a polymerization system, the seed is referred to herein as a "loaded seed."

One embodiment of the seeded processes of this invention takes advantage of the living type kinetics of the polymerization systems of this invention (including the ability to re-initiate chains) by supplying the monomer to the system in at least two stages. In the first stage, a seed is made. Depending on the embodiment of the invention being practiced, the second step is optional, and, comprises loading the seed with either (1) a composition comprised of initiator or initiating radical and/or a control agent or (2) initiator-control agent adduct. The third stage or step is to polymerize a heterogeneous mixture comprising the loaded seed under polymerization conditions. In other embodiments, this process can be described as forming a first mixture comprised of a first polymerizable monomer, initiator, water and surfactant, wherein said first polymerizable monomer comprises no more than about 10% by weight of said first mixture; subjecting said first mixture to polymerization conditions to give a first heterogeneous polymerization; ending said first heterogeneous polymerization to provide a seed, and optionally recovering said seed; forming a second mixture comprised of said seed, water and either (1) a composition comprised of an initiator or initiating radical and/or a control agent or (2) an initiator-control agent adduct; optionally maintaining the second mixture for a sufficient time under appropriate conditions for either of the composition or adduct to migrate into the seed; forming a third mixture comprised of the second mixture, optionally additional water and/or surfactant and at least one monomer, which may be the same or different from the first polymerizable monomer; and subjecting the third mixture to polymerization conditions to polymerize the at least one monomer. This third mixture is typically a living type polymerization system. In this alternative description, the first mixture forms the seed, the second mixture loads the seed and the third mixture is the heterogeneous polymerization using the loaded seed. Unloaded seeds may be provided in a manner known to those of skill in the art, such as by uncontrolled polymerization to the desired seed size, using one or more monomers of choice. In some embodiments it may be desirable to add all of the desired surfactant for the polymerization system in the process to prepare the seed and/or the loaded seed, so that no additional surfactant is added during the final polymerization step.

The seeded emulsion polymerization systems of this invention include the use of seeds as is known in the art. This simply refers to the practice of including seeds in the heterogeneous polymerization system to assist with the nucleation step. See, e.g., German, et al, "Controlled Radical Polymerization in Emulsion," *Macromolecule,* 1997, 30, 324–326. In these embodiments of this invention, the seed may be made via un-controlled polymerization using any polymerizable monomer, so long as the seed is not grown so large as to affect the end use of the emulsion. Those of skill in the art will appreciate that seeds of this embodiment include polymer chains that cannot be further grown or propagated in a polymerization system, which might be thought of as "dead" chains in the context of this invention. The end use of the emulsions of this invention typically tolerate a certain amount of "dead" polymer chains in the polymer particles, with the hydrodynamic radius of the seed being the limit used herein. Thus, for example, seeds having a hydrodynamic radius of about 10 nm generally will contribute about 1 dead chain per 1000 chains in the final polymer particle that has a radius of about 100 nm.

One preferred method of preparing seeds in an uncontrolled polymerization methodology is to mix water, at least one monomer and surfactant. The ratios of components may vary, as discussed above, but most preferably, there is between about 5–15% by weight of monomer, 2–7% by weight of surfactant and the remainder water. This combination is heated to a polymerization temperature (for example, above about 75° C.) and an initiator is added. The initiator may be chosen from those detailed above, but preferably is a low temperature, water-soluble initiator, such as potassium persulfate or the others listed above. The amount of initiator is in the range of from about 0.05–3% by weight of the monomer. This combination is maintained under polymerization conditions until the desired seed particle size is obtained, which it typically controlled by the amount of monomer added. The initiator is typically removed, for example, by heating the mixture to a temperature for a time sufficient to destroy the initiator (e.g., above about 95° C. for at least about 2 hours). Other preferred embodiments include higher percent solids (e.g., up to about 50 percent by weight) in the seed preparation (obtained using processes such as the semi-continuous addition of monomer to a polymerization system comprising surfactant, water and initiator). The seed may be recovered from the polymerization system used to make the seed if the seed is redispersible in a polymerization system or may be used without recovery from the polymerization system. The monomer used for the seed depends on the type of dead polymer chains that the emulsion application can tolerate. In some embodiments, the seed monomer is selected from the group consisting of styrene, tert-butyl acrylamide, styrene sulfonate, etc.

Loaded seeds may be prepared by a choice of methods. In one embodiment, water, surfactant, control agent and initiator are mixed with a fraction of the total desired amount of monomer. This first combination is mixed for a predetermined period of time at a predetermined temperature. Since the amount of monomer is limited, the polymerization reaction proceeds until the monomer is used up, effectively creating at least some "living" oligomers that can be re-initiated (for example, the living oligomers may be characterized by formula VIII, discussed below). Longer dead polymer chains might also be created in this procedure, depending on the conditions chosen. In this manner, an otherwise slow initiator is given the time it needs to initiate as many chains as it can and an organic soluble initiator cannot cause polymerization outside of the desired control mechanism. The amount of time and/or the temperature for this first step is chosen so that the chosen initiator is substantially completely reacted prior to the second or subsequent steps of the polymerization process. In this embodiment, the seeds are loaded in situ with the living oligomers, which then polymerize the remainder of the same or different monomer, which is added in the second step and essentially re-initiates the propagation step. Additional steps can be added for different monomers (to create block copolymers, such as di-block, tri-block or higher order block polymers).

An alternative method for loading seeds is to first polymerize the seed and then load the seed in a second step. Those of skill in the art, as discussed above, generally know about the polymerization of the seed. Whether the seed is recovered from the polymerization system or not, the loading of prepared seeds proceeds by forming a loading system, which comprises a mixture of the seed with either (1) a composition comprised of an initiator, initiating radical and/or control agent or (2) an initiator-control agent adduct in water. In this embodiment, with the composition or adduct should desire to reside in the organic environment of the seed as opposed to the aqueous environment. Thus, the composition or adduct typically will be selected to have greater solubility in the seed than the water. In some embodiments, simply placing the composition or adduct into the water with the seed will be enough for the composition or adduct to migrate into the seed. For example, water-solubilizing or water-dispersing groups may be placed on the nitroxide radical or initiating radical or adduct, as discussed above, in order to impart some water solubility, which may allow the nitroxide radical or adduct to migrate through the water into the seed. Compositions or adducts that have more than about 20 carbon atoms and no hydrophilic functional groups typically load slowly.

In other embodiments, a balanced loading system is formed, which "balances" water solubility with organic solubility. Adding an acid or base and/or organic solvent to the loading system forms the balanced loading system. The balanced loading system is believed to improve the rate of loading and thus the addition of acid or base and/or organic solvent should be chosen to minimize other effects, such as destabilization of the loaded seed by providing a pathway for the nitroxide radical or initiating species or adduct to migrate out of the loaded seed. A base is typically used for balancing the loading system, for example, if carboxyl or other acidic groups are substituted onto the nitroxide radical or initiating species or adduct in order to impart some water-solubility to the molecule. Conversely, acids are used with nitroxide radicals or initiating species or adducts comprising basic functional groups (such as amino groups). Acids or bases are well known in the art. For example, a specific bases include triethylamine, ammonia, sodium hydroxide and the like. Typical acids include hydrochloric acid, acetic acid and the like. Organic solvents modify the solubility of organic species in water or may assist in dissolving crystalline molecules so that loading rate is increased. The organic solvent may also modify the solubility of the loaded species in the polymeric environment of the seed. Organic solvents are well known in the art and may be selected from the group consisting of dichloromethane, ethyl acetate, acetone, dimethylformamide, methylethylketone and the like. The ratio of components in the balanced loading system is selected to maximize the loading rate, maximize the solubility of the loaded species in the seed particles and to minimize processes that may destabilize seed integrity or cause environment or economic concerns. Specific perferred embodiments are shown in the examples below.

This invention is also directed toward a loaded seed. A loaded seed may comprise polymer chains that are generally un-reactive in a free radical polymerization and either (1) a composition comprised of initiating radical and/or control agent or (2) an initiator-control agent adduct. In other embodiments, a loaded seed comprises polymer chains that are unreactive in a free radical polymerization system; and a composition comprised of initiating radical and control agent said control agent being characterized by the general formula:

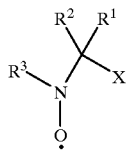

where X, $R^1$, $R^2$ and $R^3$ are defined above. In still other embodiments, the loaded seeds comprise polymer chains that are generally un-reactive in a free radical polymerization; and an initiator-control agent adduct, said initiator-control agent adduct being characterized by the general formula:

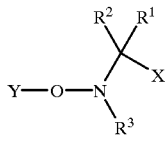

where X, Y, $R^1$, $R^2$ and $R^3$ are defined above. In still further embodiments, the loaded seeds will comprise the "living" oligomers characterized by formula VIII, below, where n is a relative low integer, such as between about 5 and 100. After the seed is loaded, the loaded seed may be recovered by separating the loaded seed from the loading system, such as by drying the solvent in loading system or with other methods as are known to those of skill in the art.

The loaded seed is subsequently used in the emulsion polymerization system. If the loaded seed is not recovered from the loading system, then the loading system (e.g., the second mixture) is used in a third mixture, the polymerization system. The polymerization system comprises additional one or more monomers and optionally more water. The monomer may be added to the polymerization system all at once or drop wise or otherwise in a controlled fashion. Also, the additional monomer may be the same or different from the monomer used to form the seed. The polymerization system is placed under polymerization conditions for the polymerization of the added monomer(s). Additional options that may be used in the polymerization system are all of those discussed above, including surfactant, accelerators, etc.

In performing this seeding process, the time and temperature of the first step (i.e., seed formation) is dependent on the exact choice of initiator and monomer. In this first step the ratio of initiator to monomer is in the molar range from about 1:10 to about 1:1000 and preferable in the range of from about 1:10 to about 1:500. Typically, the first step is carried out for between about 0.5 hours to 20 hours, preferably between about 1 and 15 hours. Also typically, the first step is carried out at a temperature of between about 50° C. and 200° C., preferably between about 70° C. to about 90° C.

Aqueous Solution Polymerization Systems

This invention also includes controlled free radical aqueous solution polymerization systems, which comprise a polymerizable composition comprising water, at least one water-soluble monomer, an initiator or initiating radical and a nitroxide radical, with the radical being characterized by formula I, above. This mixture is subjected to polymerization conditions (e.g., mixing and heating) to form a water-soluble polymer. As used in this embodiment, water-soluble refers to the ability of the monomer or polymer to effectively dissolve in water to a measurable degree, namely sufficiently so that a homogeneous polymerization system is achieved. In some preferred embodiments, the monomer is soluble or miscible in the water and the monomer may be more than 50% by weight of the mixture, so that solubility of other species in the monomer/water combination is enhanced relative to water alone. The above discussion of the general polymerization system and polymerization conditions otherwise apply to this embodiment.

Polymers—Including Block Polymers

The methods of this invention may be practiced to form new polymers. In one preferred embodiment, a "living" oligomer or polymer of this invention may be characterized by the formula:

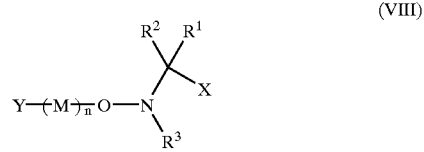

(VIII)

where $R^1$, $R^2$, $R^3$ and X have the above meanings, and Y is a residue derived from a species that initiates free radical polymerization (as discussed above) and may be selected from the group consisting of alkyl, substituted alkyl, alkoxy, substituted alkoxy, heteroalkyl, substituted heteroalkyl, aryl, and substituted aryl (Y may also be derived from the list of initiators discussed above); M is one or more monomers (as discussed above) and may be selected from the group consisting of styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate and combinations thereof; and n is an integer greater than 1, preferably greater than 10, also preferably greater than 100. As discussed above, these oligomers or polymers may be in emulsion, water-soluble or a loaded seed.

The polymers shown in formula VIII show the nitroxide radical and Y residue at each end of the polymer. These end groups may be removed or modified as is known to those of skill in the art. Specific methods that may be used include reduction with ascorbate or tin hydrides to replace the nitroxyl group with a hydrogen, addition of other radical species (such as halogens or sulfur species), and destruction of free nitroxide radical to force coupling of chains.

The living nature of the polymerization processes of this invention provide those of skill in the art the ability to create virtually any type of polymer architecture desired as well as selection from a wide variety of monomers. Thus, this invention includes novel block copolymers of styrene and acrylic acid; styrene and acrylamides (such as t-butyl acrylamide and dimetyl acrylamide); styrene and acrylates (such as n-butyl acrylate and ethyl acrylate); styrene and methacrylates (such as n-butyl methacrylate and methyl methacrylate); acrylic acid and methacrylic acid; acrylic acid and acrylamides; acrylic acid and acrylates; acrylic acid and methacrylates; methacrylic acid and acrylamides; methacrylic acid and acrylates; methacrylic acid and methacrylates; acrylamides and acrylates; acrylamides and methacrylates; and acrylates and methacrylates. Some of these block copolymers are exemplified in the below examples. Although some of these types of block copolymers may have been prepared by other methods, this invention provides a controlled free radical method of synthesis with living type kinetics that leads to novel properties. Novel properties include higher molecular weights (e.g., above 50,000 weight average molecular weight) and better particle size control, as discussed above. Molecular weights for the polymer (or blocks, as discussed below, to achieve aggregate molecular weights) can be from 25,000 and higher, preferably 50,000 and higher, more preferably from 100,000 and higher. From these properties, other properties can be derived, as discussed elsewhere in this specification. For some applications, the polymers may be used in the heterogeneous medium in which they are created; in others, the polymers may be isolated from the emulsion. Polymers may be isolated using a variety of well-known techniques, including, for example, coating, drying, spray drying, coagulation (i.e., with salt, solvent, thermal cycling, shear, etc.), extraction with solvent, chemical modification of the polymer and the like, depending on the application. Modifiers, stabilizers or other additives may be added to the polymers for particular applications, whether in emulsion or not, as is known to those of skill in the art.

As used herein, "block copolymer" refers to a polymer comprising at least two segments of differing composition; having any one of a number of different architectures, where the monomers are not incorporated into the polymer architecture in a solely statistical or uncontrolled manner. Although there may be three, four or more monomers in a single block-type polymer architecture, it will still be referred to herein as a block copolymer. In some embodiments, the block copolymer will have an A-B architecture (with "A" and "B" representing the monomers). Other architectures included within the definition of block copolymer include A-B-A, A-B-A-B, A-B-C, A-B-C-A, A-B-C-A-B, A-B-C-B, A-B-A-C (with "C" representing a third monomer), and other combinations that will be obvious to those of skill in the art.

In another embodiment, the block copolymers of this invention include one or more blocks of random copolymer together with one or more blocks of single monomers. Thus, a polymer architecture of A-R, R-R', A-R-B, A-B-R, A-R-B-R-C, etc. is included herein, where R is a random block of monomers A and B or of monomers B and C. Moreover, the random block can vary in composition or size with respect to the overall block copolymer. In some embodiments, for example, the random block R will account for between 5 and 80% by weight of the mass of the block copolymer. In other embodiments, the random block R will account for more or less of the mass of the block copolymer, depending on the application. Furthermore, the random block may have a compositional gradient of one monomer to the other (e.g., A:B) that varies across the random block in an algorithmic fashion, with such algorithm being either linear having a desired slope, exponential having a desired exponent (such as a number from 0.1–5) or logarithmic. The random block may be subject to the same kinetic effects, such as composition draft, that would be present in any other radical copolymerization and its composition, and size may be affected by such kinetics, such as Markov kinetics. For example, as shown below in the examples, a block copolymer of (random methyl methacrylate-ureidoethylmethacrylate) and styrene is made that is within the scope of this definition. Any of the monomers listed elsewhere in this specification may be used in the block copolymers of this invention.

A "block" within the scope of the block copolymers of this invention typically comprises about 10 or more monomers of a single type (with the random blocks being defined by composition and/or weight percent, as described above). In preferred embodiments, the number of monomers within a single block may be about 15 or more, about 20 or more or about 50 or more. However, in an alternative embodiment, the block copolymers of this invention include blocks where a block is defined as two or more monomers that are not represented elsewhere in the copolymer. This definition is intended to encompass adding small amounts of a second monomer at one or both ends of a substantially homopolymeric polymer. In this alternative embodiment, the same copolymer architectures discussed above apply. This definition is therefore intended to include telechelic polymers, which include one or more functional end groups capable of reacting with other molecules. Thus, generally, a telechelic polymer is a block copolymer with in the definitions of this invention. The functional groups present at one or both ends of a telechelic polymer may be those known to those of skill in the art, including, for example, hydroxide, aldehyde, carboxylic acid or carboxylate, halogen, amine and the like, which have the ability to associate or form bonds with another molecule. Likewise, the block copolymers of the invention are intended to encompass telechelic polymers containing bifunctional groups, such as allyl-terminated or vinyl-terminated telechelics, sometimes referred to as macromonomers or macromers because of their ability to participate in polymerization reactions through the terminal functional group.

Combining the above embodiments provides a particularly powerful method of designing block copolymers. For example, a block copolymer may have the architecture F-A-B-F, where F represents functional groups that may be the same or different within a single F-A-B-F structure (which, therefore, may encompass F-A-B-F'). Other block copolymer architectures within the scope of this invention include A-R-B-F and F-A-R-B-F. Other architectures will be apparent to those of skill in the art upon review of this specification—indeed, without wishing to be bound by any particular theory—it is the living nature of the emulsions of this invention that provide the ability to even make these novel block copolymers.

In one embodiment, block copolymers are assembled by the sequential addition of different monomers or monomer mixtures to living polymerization reactions. In another embodiment, the addition of a pre-assembled functionalized block (such as a telechelic oligomer or polymer) to a living free radical polymerization mixture yields a block copolymer. Ideally, the growth of each block occurs with high conversion. Conversions are determined by size exclusion chromatography (SEC) via integration of polymer to monomer peak. For UV detection, the polymer response factor must be determined for each polymer/monomer polymerization mixture. Typical conversions can be 50% to 100% for each block. Intermediate conversion can lead to block copolymers with a random copolymer block separating the two or more homopolymer blocks, depending on the relative rates of polymerization and monomer addition. At high conversion, the size of this random block is sufficiently small such that it is less to affect polymer properties such as phase separation, thermal behavior and mechanical modulus. This fact can be intentionally exploited to improve polymerization times for many applications without measurably affecting the performance characteristics of the resulting polymer. This is achieved by intentionally "killing" or terminating the living nature of the polymerization when a desired level of conversion (e.g., >80%) is reached by neutralizing the control agent, for example by introducing acids, bases, oxidizing agents, reducing agents, radical sources, scavengers, etc. In the absence of control agent, the polymerization continues uncontrolled (typically at much higher reaction rates) until the remaining monomer is consumed. Block copolymer can also be created by grafting monomers, monomer mixtures, oligomers or polymers only polymers having multiple available functional groups.

In other embodiments, block copolymers can be prepared by grafting processes, preparation of telechelic polymers, preparation of macromonomers, etc. In these embodiments, at least one polymer segment is derived from a living or controlled process of the invention, while other segments can be derived from any polymerization process, including, for example, controlled or uncontrolled radical polymerization, condensation polymerization, ionic polymerization, surface modification or grafting, or other addition or step-growth processes.

The combination of heterogeneous (and particularly emulsion) conditions with living-type free radical kinetics provides a high degree of control over the composition, architecture, phase morphology and microstructure of polymers produced according to the invention. These methods may be practiced to form new polymers, including, for example, di-, tri-, poly-, multi-arm, star and graft block copolymers in addition to novel homopolymers.

Block copolymers allow the combination of potentially diverse polymer properties (such as hard/soft and/or hydrophilic/hydrophobic (amphiphilic) blocks) into a single polymer chain. Hard/soft block copolymers combine segments with significantly different glass transition temperatures $T_g$. A typical hard/soft copolymer pairs a relatively "hard" block (e.g., styrene) with a relatively "soft" block (e.g., butyl acrylate). The resulting materials can possess performance attributes not found in any of the constituent segments. The presence of microphase separation and various phase morphologies in block copolymers is associated with unique performance attributes of many block copolymers. For example, by combining the stiffness or rigidity characteristic of hard materials with the compliance of soft materials, block copolymers may exhibit advantageous properties, such as processability under melt conditions, elasticity, resistance to abrasion and cracking and desired creep characteristics (corresponding to the material's ability to hold its shape under external stresses) depending on morphology, making them appropriate for use as extrudable bulk materials, coatings and separation media. The exact properties of a hard/soft copolymer depend significantly on the difference between the glass transition temperatures of the constituent blocks; accordingly, selection of monomers having glass transition temperatures a particular distance apart can lead to hard/soft block copolymers having particular desired characteristics. Thus, while for one application it may be appropriate to combine blocks having glass transition temperatures that differ by, for example, 20° C., the choice of $T_g$ (and therefore of materials) depends on the application. Monomers that can be combined to form hard and soft blocks are known in the art. See e.g., U.S. Pat. No. 5,755,540.

Likewise, the amphiphilic block copolymers produced according to the invention display combinations of hydrophobic and hydrophilic properties that make such materials appropriate for use as surfactants or dispersants, scavengers, surface treatments and the like. Different block sizes over all ratios of monomers and molecular weights lead to families of novel compounds, for example thermoplastics, elastomers, adhesives, and polymeric micelles.

The existence of a block copolymer according to this invention is determined by methods known to those of skill in the art. For example, those of skill in the art may consider nuclear magnetic resonance (NMR) studies of the block copolymer. Those of skill in the art would also consider the measured increase of molecular weight upon addition of a second monomer to chain-extend a living polymerization of a first monomer. Block copolymer structure can be suggested by observation microphase separation, including long range order (determined by X-ray diffraction), microscopy and/or birefringence measurements. Other methods of determining the presence of a block copolymer include mechanical property measurements, (e.g., elasticity of hard/soft block copolymers), thermal analysis and chromatography (e.g., absence of homopolymer).

Measurement of optical properties, such as absorbance (color and clarity), provides information about the phase morphology and microstructure of the polymer emulsions. Thus, for example, birefringence measurements may indicate the presence of optical anisotropy resulting from microphase separation in hard/soft block copolymers of styrene and butyl acrylate. Likewise, sharp color delineations in optical micrographs of annealed polymer films can indicate the presence of ordered, microphase-separated block copolymer structure.

Block copolymers of sufficiently high molecular weight phase separate on a microscopic scale, to form periodically arranged microdomains which typically comprise predominantly one or the other polymer. These may take the form of lamellae, cylinders, spheres, and other more complex morphologies, and the domain sizes and periods are typically in the range 10–100 nm. Such microphase separation can be detected obtained in a variety of ways, including electron microscopy, x-ray or neutron scattering or reflectivity, measurement of optical anisotropy, and rheological measurements. The absence of a periodic microstructure is not necessarily evidence against having synthesized a block copolymer, as such absence may be due to low molecular weight, weak intermolecular interactions, or inadequate time and slow kinetics for microphase separation. However, the presence of a periodic microstructure on the 10–100 nm scale is considered extremely compelling evidence for block copolymer formation in accord with this invention.

Block copolymers are well-known to form terraced films, where the film thickness is restricted to integer or half-integer multiples of the microstructure period. This occurs because preferential interactions of one or the other block with the substrate and/or free surface cause a layering of the microdomains parallel to the film surface (see for example G. Coulon, D. Ausserre, and T. P. Russell, *J. Phys. (Paris)* 51, 777 (1990); and T. P. Russell, G. Coulon, V. R. Deline, and D. C. Miller, *Macromolecules* 22, 4600–6 (1989)). When observed in a reflection microscope (on a reflecting substrate such as a silicon wafer), the terracing manifests itself as a series of discrete, well-defined colors with sharp boundaries between them as shown in FIG. 12. The colors are a result of interference between light reflected from the top and bottom surfaces of the film, and depend on the local film thickness ("Newton's rings"). If terracing does not occur, the colors blend continuously from one into the other.

The presence of block copolymer can also be determined using transmission electron microscopy as illustrated in FIGS. 13A and 13B.

The novel properties of the copolymers and emulsions, including the high molecular weight, low polydispersity and controlled phase morphology and microstructure of the copolymers and the particle size and optical purity of the emulsions make them suitable for a wide variety of applications including adhesives, binders, coatings, dispersants, scavengers, rheology modifiers, bulk extrudable materials and health and personal care products. Thus, for example, pressure sensitive adhesives may be prepared using the emulsions or dispersions of this invention, with such adhesives including tackifiers and/or plasticizers, as known in the art (see, e.g., U.S. Pat. No. 4,879,333, which is incorporated herein by reference).

EXAMPLES

Synthesis work was carried out under an inert atmosphere in a glove box under a nitrogen or argon atmosphere. Typically, simultaneous, multiple polymerization experiments were carried out in 1 mL glass vials fitted in an aluminum block, and sealed with a Teflon faced silicon rubber gasket backed with a stainless steel lid. Agitation was achieved by placing a 5 mm diameter glass ball in each vial and mounting the aluminum block on a rocking platform oscillating at one to two Hz. Heating was achieved using resistive heaters mounted to the aluminum block. The total polymerization reaction volume for the parallel polymerizations was generally about 0.7 mL. The starting components for polymerizations were delivered in aqueous or monomer solutions, and typical concentrations were 0.02 to 0.1 mol/L. In general the initiator was the last component added to the polymerization systems. After the reactions had been heated for a predetermined time at a predetermined temperature, the complete contents of each reaction was dissolved in 10 mL of THF and analyzed by SEC (size exclusion chromatography) using rapid SEC/adsorption chromatography as described in commonly assigned U.S. Provisional Patent Application No. 60/080,652, filed Apr. 3, 1998, as further described in U.S. patent application Nos. 09/285,363; 09/285,333; 09/285,335; or 09/285,392; each of which was filed on Apr. 2, 1999 and each of which is incorporated herein by reference. Specifically, a Waters 486 UV detector at 220 nm was used with two 5 cm×8 mm columns in series custom packed with Suprema Gel (PSS, Mainz Germany).

Monomers were degassing by applying three freeze-pump-thaw cycles. Initiators were purchased from the suppliers listed in Table 1, above and used as is. Surfactants and any other reagents were used as received (when they were dry solids), or degassed by applying three freeze-pump-thaw cycles (when they were liquids or solutions). The water used in all experiments was distilled and degassed prior to use. Degassing was accomplished by stirring the water while under dynamic vacuum and stripping off approximately 20% of the water.

Nuclear magnetic resonance spectra were recorded on a Bruker Spectrospin 300 instrument at room temperature. Thin layer chromatography was performed using 2.5×7.5 cm glass plates precoated with silica gel 60 F254 (EM Science, Merck KgaA, Darmstadt, Germany), with detection by UV-quenching at λ=254 nm and/or staining with 10% phosphomolydic acid hydrate in EtOH with heating. Gas chromatography/mass spectrometry (GC/MS) was performed using an HP 6890 gas chromatograph equipped with an automatic injector, a siloxane-coated capillary column, and an HP 5973 mass spectrometer. Second cumulant analysis PDI was determined as discussed above. Mp refers to peak molecular weight as determined by SEC.

Example 1: Preparation of Nitroxide Radicals, Starting Materials and Initiator-Control Agent Adducts This example provides methods of synthesizing nitroxide radicals, starting materials and intiator control agent adducts that are useful in this invention. Part A shows the source or preparation of starting nitrones. Part B shows conversion of nitrones into nitroxide radicals. Parts C, D and E show preparation of molecules that are used in the preparation of initiator control agent adducts, which is shown in detail in Part F. Parts G, H, I and J show conversion of initiator control agent adducts (some of which are from Part F) into different initiator control agent adducts. Part K shows preparation of the hydroxyl functionalized initiator control agent adducts.

PART A

Synthesis of N-tBu,α-Arylnitrones

The following Scheme 1 was followed, in connection with Table 3:

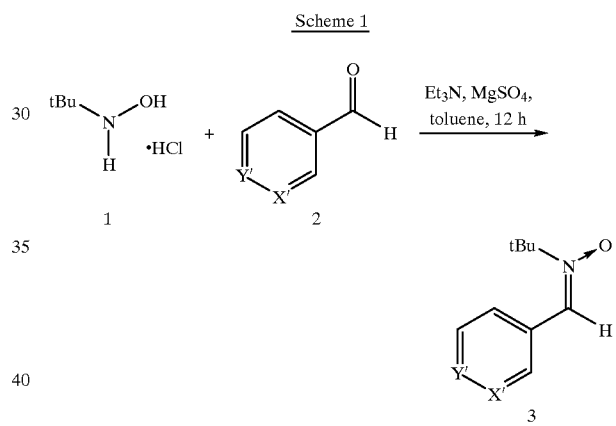

TABLE 3

| Entry | Aldehyde 2 | Nitrone 3 | X' | Y' | yield [%] |
|---|---|---|---|---|---|
| 1 | 2a | 3a | CH | CH | commercially available |
| 2 | 2b | 3b | N | CH | 84% |
| 3 | 2c | 3c | CH | CBr | quant. |

Commercial Source of N-tert-Butyl-α-phenylnitrone (3a)

3a: N-tert-Butyl-α-phenylnitrone, [3376-24-7], Aldrich chemical company, Milwaukee, USA. Used as received.

Synthesis of N-tert-Butyl-α-(3-pyridyl)nitrone (3b)

According to a protocol of A. Dondoni, et al., (*Synth. Commun.* 1994, 24, 2537–2550), an ovendried 250 mL round-bottomed flask equipped with a magnetic stir bar, reflux condenser and adapter to an argon line was charged with 2.512 g (20.0 mmol) of N-tert-butylhydroxylamine hydrochloride (1), 2.144 g (20.0 mmol) of pyridine-3-carboxaldehyde (2b), and 2.889 g (22.0 mmol) of MgSO$_4$.100 mL of anhydrous toluene were added followed by 2.024 g (20.0 mmol, 2.79 mL) of anhydrous Et$_3$N. The reaction mixture was heated to 100–110° C. under atmosphere of argon, and the reaction course was followed by t.l.c. and GC/MS. After 3–5 h, the reaction was cooled to room temperature, MgSO$_4$ was filtered off, and the solvent was evaporated under reduced pressure to yield a dark yellow-green mixture of product and Et$_3$N HCl. The solids were dissolved in EtOAc and the solution was subsequently washed with a saturated aq. NaHCO$_3$-solution (50 mL) to remove Et$_3$N HCl, water (50 mL), and brine (50 mL), dried over MgSO$_4$, filtered, and evaporated under reduced pressure. The crude product was purified by passing through a short plug of silica gel (EtOAc/hexanes (1: 1) to yield after evaporation 3.000 g (84%) of a pale yellow solid. R$_f$: 0.61 (EtOAc/hexanes=1:9, UV$_{254}$-quenching). GC: R$_t$: 3.92 min. $^1$H NMR (300 MHz, CDCl$_3$, room temp.): δ9.06 (dt, J=8.4, 1.8 Hz, 1H, Ar-H), 8.93 (d, J=1.8 Hz, 1H, Ar-H), 8.53 (dd, J=8.8, 1.8 Hz, 1H, Ar-H), 7.56 (s, 1H, HC(=N)), 7.31 (dd, J=8.1, 4.8 Hz, 1H, Ar- H), 1.54 (s, 9H, C(CH$_3$)$_3$) ppm. $^{13}$C NMR (75 MHz, CDCl$_3$, room temp.): δ150.20, 150.09, 134.57, 127.49, 126.91, 123.40, 71.43, 28.24 ppm. MS: m/z=178 (M$^+$), 147, 122 (b.p., M$^+$—H$_2$C=C(CH$_3$)$_2$), 106, 79, 57.

Synthesis of N-tert-Butyl-α-(4-bromophenyl)nitrone (3c)

By anaolgy to the procedure for the synthesis described above, 5.024 g (40.0 mmol) of N-tert-butylhydroxylamine hydrochloride (1) were reacted with 6.476 g (35.0 mmol) of 4-bromobenzaldehyde (2c) in 100 mL of anhydrous toluene, and in the presence of 4.554 g (45 mmol, 6.27 mL) of Et$_3$N and 8.425 g (70.0 mmol) of MgSO$_4$. Purification of the crude yellow oil by column chromatography (silica gel, EtOAc/hexanes=1:6 to 1:3) yielded 8.95 g (quant.) of colorless crystals. R$_f$: 0.25 (EtOAc/hexanes=1:4, UV$_{254}$-quenching). $^1$H NMR (300 MHz, CDCl$_3$, room temp.): δ8.14 (dt, J=8.7,2.4 Hz, 2H, Ar-H), 7.49 (dt, superimposed, J=8.7,2.4 Hz, 2H, Ar-H), 7.48 (s, superimposed, 1H, HC(=N)), 1.56 (s, 9H, C(CH$_3$)$_3$) ppm. $^{13}$C NMR (75 MHz, CDCl$_3$, room temp.): δ131.53, 130.06, 129.81, 128.92, 123.73, 71.09, 28.20 ppm.

PART B

Synthesis of 4-aryl, 3-oxyl, 2,2,5-trimethyl-3-azahexanes

The following Scheme 2 was followed in connection with Table 4:

Scheme 2

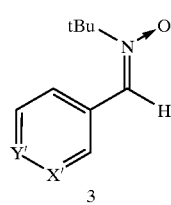

1. iPrMgCl (4), Et$_2$O,
   0° C. to r.t., 12 h
2. cat. Cu(OAc)$_2$, NH$_4$OH,
   MeOH, air, r.t., 2 h -continued

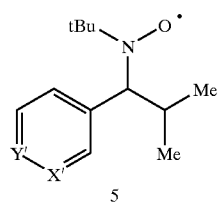

TABLE 4

| Entry | nitrone 3 | Nitroxide 5 | X' | Y' | yield [%] |
| --- | --- | --- | --- | --- | --- |
| 1 | 3a | 5a | CH | CH | ca. 90 |
| 2 | 3b | 5b | N | CH | ca. 90 |
| 3 | 3c | 5c | CH | Br | 56 |

Synthesis of Nitroxide 5a

An ovendried 500 mL Schlenk-flask equipped with a magnetic stirring bar and a rubber septum was charged under argon atmosphere with 8.86 g (50.0 mmol) of N-tert-Butyl-α-phenylnitrone (3a). The compound was dissolved in 250 mL of anhydrous THF at room temperature. The yellowish solution was cooled to 0° C. (ice bath) and isopropylmagnesium chloride (4) (2 M in THF, 40 mL, 80.0 mmol) were added dropwise at this temperature with a syringe. The reaction mixture was stirred overnight with warming to room temperature to yield a bright yellow to brownish clear solution. Both, thin layer chromatography (t.l.c.) and GC/MS (M$^+$=221) showed formation of the intermediate hydroxylamine together with variable amounts of the appropriate nitroxide GC/MS (M$^+$=220). The solvent was evaporated under reduced pressure and the residues were redissolved in 600 mL of MeOH. 100.0 mL of 28% aqueous NH$_4$OH were added (some precipitation of Mg(OH)$_2$ occurs) and 453 mg (2.5 mmol) of Cu(OAc)$_2$ (5.0 mol-%) were added. Through the well stirred yellowish reaction mixture was bubbled air via a syringe needle for 2–3 h at room temperature till the reaction mixture turned significantly green-blue. Most of the MeOH was removed under reduced pressure and the remaining crude product was diluted with diethyl ether (250 mL) and water (150 mL). The aqueous phase was extracted twice with diethyl ether and the combined organic extracts were washed successively with water and saturated aqueous NaCl-solution. Drying over MgSO$_4$, 30 min, filtration, and evaporation yielded 9.95 g (ca. 90%) of the crude nitroxide as a dark orange viscous oil which solidified in a refrigerator. Analytical data for the intermediate hydroxylamine: GC: R$_t$: 3.46 min. $^1$H NMR (300 MHz, CDCl$_3$, room temp.): δ7.52-7.42 (br. m, 2H, Ar-H), 7.39-7.26 (br. m, 3H, Ar-H), 4.05 (br.s, 1H, OH), 3.46 (d, J=9.6 Hz, 1H, NCH), 2.35 (br. m, 1H, CH(CH$_3$)$_2$), 1.21 (d, J=6.0 Hz, 3H, CH(CH$_3$)$_2$), 1.00 (s, 9H, C(CH$_3$)$_3$), 0.65 (d, J=6.0 Hz, 3H, CH(CH$_3$)) ppm. $^{13}$C NMR (75 MHz, CDCl$_3$, room temp.): δ140.02, 128.14, 125.85, 124.76, 69.39, 57.18, 29.58, 25.00, 19.78, 18.70 ppm MS: m/z: 220 (M+.), 178, 162, 133 (b.p.), 122, 117, 91, 57, 41. Analytical data for the nitroxide 5a (in accordance with R. Braslau, C. J. Hawker, et al., (J. Am. Chem. Soc., 1999, 121, 3904–3920). R$_f$: 0.49 (EtOAc/hexanes=1:16, visible yellow spot or UV$_{254}$-quenching). GC: R$_t$: 3.50 min. $^1$H NMR (300 MHz, CDCl$_3$, room temp., 10.0 mg nitroxide/9.9 mg pentafluorophenyl hydrazine): δ7.38-7.22 (br. m, 2H, Ar-H), 7.31-7.15 (br. m, 3H, Ar-H), 5.15 (br. m, 1H, F$_5$C$_6$NHNH$_2$), ), 4.1-3.6 (br. m, 2H, F$_5$C$_6$NHNH$_2$), 3.40 (d, J=9.6 Hz, 1H, NCH), 2.29 (br. m, 1H, CH(CH$_3$)$_2$), 1.12 (d, J=6.0 Hz, 3H, CH(CH$_3$)$_2$), 0.97 (s, 9H, C(CH$_3$)$_3$), 0.58 (d, J=6.0 Hz, 3H, CH(CH$_3$)$_2$) ppm. MS: m/z: 221 (M+.), 178, 162, 146, 133 (b.p.), 122, 91, 57.

Synthesis of Nitroxide 5b

By analogy for the procedure for the synthesis described above, nitroxide 5b was prepared from N-tert-butyl-α-(3-pyridyl)nitrone (3b) (891 mg, 5.0 mmol) and isopropylmagnesium chloride (4) (2 M in THF, 5.0 mL, 10.0 mmol) in 50 mL of anhydrous tetrahydrofurane (THF). Both, t.l.c. and GC/MS (M$^+$=222) showed formation of the intermediate hydroxylamine. After work-up, oxidation of the crude intermediate hydroxylamine in 50 mL of MeOH and 5.0 mL of 28% aq. NH$_4$OH (some precipitation of Mg(OH)$_2$ occured) and in the presence 46 mg of Cu(OAc)$_2$ yielded 995 mg (ca. 90%) of the crude nitroxide as a dark orange oil. Both, t.l.c. and GC/MS (M$^+$=221) showed that the crude product contained some impurity of the nitrone (M$^+$=220) due to over-oxidation of nitroxide in a ratio of ca. 10:1 in favor for the nitroxide. The crude product was directly used in the next step without further purification.

Synthesis of Nitroxide 5c

By analogy for the procedure for the synthesis described above, nitroxide 5c was prepared from N-tert-butyl-α-(3-pyridyl)nitrone (3c) (8.96 g, 35.0 mmol) and isopropylmagnesium chloride (4) (2 M in THF, 35.0 mL, 70.0 mmol) in 250 mL of anhydrous tetrahydrofurane (THF). T.l.c. showed clean formation of the intermediate hydroxylamine. After work-up, oxidation of the crude intermediate hydroxylamine in 250 mL of MeOH and 25.0 mL of 28% aq. NH$_4$OH and in the presence of 317 mg (1.75 mmol) of Cu(OAc)$_2$ yielded the crude nitroxide as a dark orange oil which solidified upon standing at room temp. Purification by medium pressure liquid chromatography (MPLC) (silica gel, EtOAc/hexanes=1:24) yielded 5.85 g (56%) of a bright orange crystaline solid. The purified product was then used in the next step. R$_f$: 0.48 (EtOAc/hexanes=1:9).

PART C

Synthesis of Dimethyl (5-ethylenyl)isophthalate

The following Scheme 3 was following in this part:

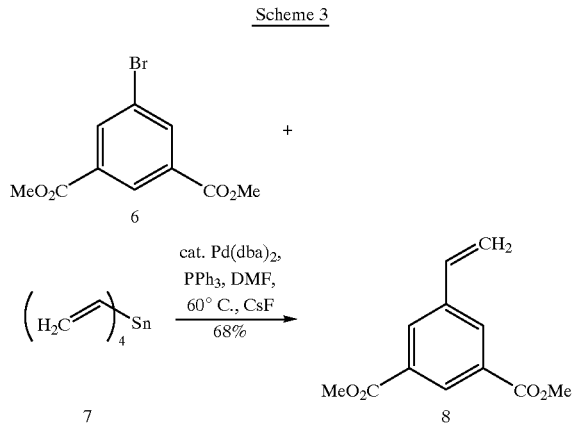

Scheme 3

Synthesis of dimethyl (5-ethylenyl)isophthalate (8)

A 100 mL ovendried Schlenk-flask equipped with a magnetic stirring bar and a rubber septum was charged under argon atmosphere with dimethyl 5-bromoisophthalate (6) (2.739 g, 10.0 mmol), tetravinyltin (7) (1.135 g, 5.0 mmol, 0.91 mL), bis(benzylidene)acetone palladium (0.287 g, 0.5 mmol), triphenylphosphine (0.262 g, 1.0 mmol), and cesium fluoride (3.646 g, 24 mmol). The solids were dissolved in 40 mL of anhydrous dimethylformamide (DMF) and heated under an atmosphere of argon to 60° C. The reaction course was monitored by t.l.c. After complete consumption of the starting material, the reaction mixture was quenched with 100 mL of water. The aqueous phase was extracted with diethyl ether (3×50 mL), the combined organic extracts were washed with brine and dried over MgSO$_4$. After filtration and evaporation of the solvent under reduced pressure, the crude material was purified by recrystalization from methanol to yield 1.50 g (68%) of a colorless crystaline solid. R$_f$: 0.38 (EtOAc/hexanes=1:9). GC: R$_t$=5.76 min. $^1$H-NMR (300 MHz, CDCl$_3$, room temp.): δ8.57 (t, J=1.5 Hz, 1H, Ar-H), 8.26 (d, J=1.5 Hz, 2H, Ar-H), 6.79 (dd, J=17.4, 10.8 Hz, 1H, CH=CHH), 5.93 (d, J=17.4 Hz, 1H, CH=CHH), 5.42 (d, J=11.1 Hz, 1H, CH=CHH), 4.02 (s, 6H, OCH$_3$) ppm. $^{13}$C-NMR: (75 MHz, CDCl$_3$, room temp.): δ166.13, 138.33, 135.00, 131.26, 130.86, 129.64, 116.42, 52.36 ppm. MS: m/z=220 (M$^+$), 189 (b.p., M$^+$-OMe), 175, 161, 146, 129, 118, 102, 89, 76, 63, 51.

PART D

Synthesis of the Neon-B Protecting Group

The following Scheme 4 was followed in the first section of Part D:

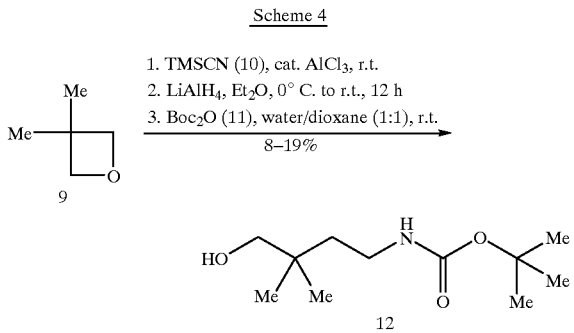

Scheme 4

Synthesis of the Neon-B Protecting Group

According to the protocol of J. C. Roberts, et al. (*Tetrahedron Lett.*, 1997, 38, 355–358; WO 96/18609), an ovendried 100 mL Schlenk flask equippped with a magnetic stir bar and a rubber septum was loaded under an atmosphere of argon and t room temp. with 9.86 g (100 mmol, 13.5 mL) trimethylsilylcyanide (10) followed by 269 mg (2.0 mmol) of aluminum trichloride to yield a colorless jelly. 8.35 g (97 mmol) 3,3-dimethyloxetane (9) were added at room temp. and the reaction mixture was stirred for 12 h at room temp. Unhydrous diethyl ether (100 mL) was added to the nitrile, the solution was cooled to ca. 0° C. (icebath) and 240 mL of a 1.0 M LiAlH$_4$-solution in diethyl ether (240 mmol) were added dropwise. Upon warming to room temp., the reaction mixture was stirred for 12 h, and excess reduction reagent was quenched by successive careful addition of 10 mL water, 10 mL of 5% aq. NaOH-solution, and 10 ml water. The colorless Al-containing precipitate was filtered off through a sintered glass-funnel, washed with diethyl ether (2×50 mL) and the solvent was evaporated under reduced pressure to yield a pale yellow oil which was used directly without further purification in the next step. The crude product was dissolved in dioxane (50 mL) and ca. 16.2 mL of 6.0 N hydrochloric acid were added (formation of amine hydrochloride). After 30 min. at room temp., the pH of the reaction mixture was adjusted to about 8.0 (pH-paper) by slow addition of a saturated aq. $NaHCO_3$-solution., and the reaction mixture was diluted with water (100 mL). Di-tert-butyl dicarbonate ($Boc_2O$, 11) (24.0 g, 110 mmol) was added portionwise and stirring was continued for 16 h at room temp. After partial concentration under reduced pressure, the concentrate was diluted in EtOAc (150 mL) and the aqueous phase was extracted with EtOAc (3×50 mL). The combined organics were washed with sat. aq. $NH_4Cl$-solution, water, brine, dried over MgSO4, filtered and evaported under reduced pressure to yield a pale yellow oil. Purification by MPLC (EtOAc/hexanes=3:1 to 1:1) yielded 3.98 g (19%) of Neon-B alcohol 12 as a colorless crystaline solid. $R_f$: 0.65 (EtOAc/hexanes=3:1+2 vol.-% $Et_3N$, ninhydrine stain). GC: $R_t$=3.72 min. $^1$H-NMR (300 MHz, CDCl3, room temp.) δ4.67 (br. s, 1H, NH), 3.31 (s, 2H, $CH_2OH$), 3.12-3.05 (m, 2H, $CH_2NH$), 2.32 (br. s, 1H, OH), 1.45-1.43 (m, 2H, CH2), 1.40 (s, 9H, $C(CH_3)_3$), 0.86 (s, 6H, $C(CH_3)_2$) ppm. $^{13}$C-NMR (75 MHz, $CDCl_3$, room temp.): δ156.19, 79.25, 71.01, 38.36, 36.58, 34.57, 28.40, 24.22 ppm. MS: m/z: 160 ($M^+$-tBu), 131, 99, 74, 57 (b.p., $tBu^+$).

Synthesis of the Neon-B Protected 4-sulfonyl Styrene

The following Scheme 5 was followed in this second section of Part D.

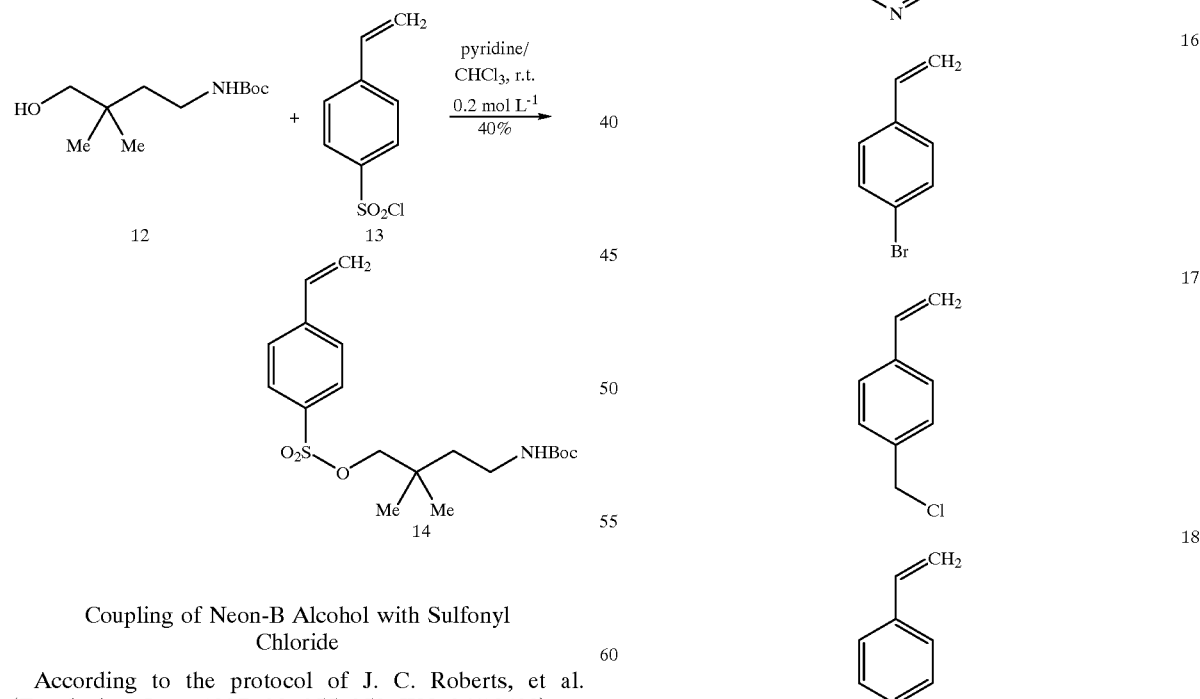

Scheme 5

Coupling of Neon-B Alcohol with Sulfonyl Chloride

According to the protocol of J. C. Roberts, et al. (*Tetrahedron Lett.*, 1997, 38, 355–358; WO 96/18609), an ovendried 100 mL Schlenk flask equippped with a magnetic stir bar and a rubber septum was loaded under an atmosphere of argon and room temp. with 1.087 g (5.0 mmol) of alcohol 12. The alcohol was dissolved in 25 mL of anhydrous chloroform ($CHCl_3$) and 791 mg (10.0 mmol, 809 μL) of anhydrous pyridine. The solution was cooled to ca. 0° C. (icebath) and 1.013 g (5.0 mmol, 825 μL) of the sulfonyl chloride 13 were added under argon atmosphere. Stirring was continued with warming to room temp. for 12 h. The reaction was quenched with 20 mL of a saturated aq. $NaHCO_3$-solution, and diluted with EtOAc (25 mL). After extraction of the aqueous phase with EtOAc (2×25 mL), the combined organic extracts were succesively washed with water (20 mL), saturated aq. $CuSO_4$-solution (2×20 mL) and brine (20 mL), dried over $MgSO_4$, filtered, and the filtrate was evaporated under reduced pressure to yield a pale yellow viscous oil. Purification by MPLC (silica gel, EtOAc/hexanes=8:1 to 2:1) yielded 768 mg (40%) of a colorless viscous oil. $R_f$: 0.45 (EtOAc/hexanes=1:2, 0.3% aqueous $KMnO_4$ staining). $^1$H-NMR (300 MHz, $CDCl_3$, room temp.): δ7.81 (d, J=8.4 Hz, 2H, Ar-H), 7.52 81 (d, J=8.4 Hz, 2H, Ar-H), 6.73 (dd, J=17.7, 11.1 Hz, 1H, CH=CHH), 5.88 (d, J=17.7 Hz, 1H, CH=CHH), 5.44 (d, J=17.7 Hz, 1H, CH=CHH), 4.44 (br. s, 1H, NH), 3.66 (s, 2H, $CH_2O$), 3.10-2.2.95 (br. m, 2H, $CH_2CH_2N$), 1.44-1.36 (br. m, s, superimposed, 11H, $CH_2CH_2N$, $C(CH_3)_3$), 0.87 (s, 6H, $C(CH_3)_2$) ppm. $^{13}$C-NMR (75 MHz, $CDCl_3$, room temp.): δ155.74, 142.87, 135.10, 134.51, 128.18, 126.78, 118.04, 79.16, 77.91, 38.22, 36.18, 33.58, 28.34, 23.72 ppm.

PART E

The sources of the following compounds are shown below:

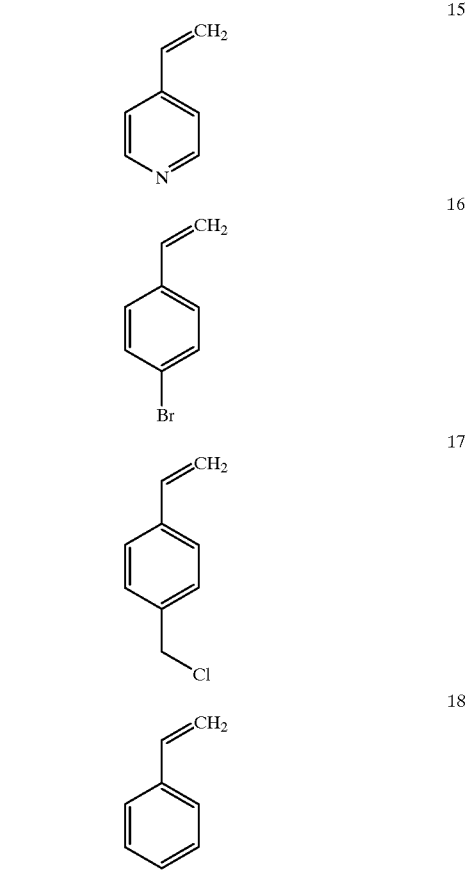

Commercial Sources of Compounds 15–18

15: 4-Vinylpyridine, [100-43-6], Aldrich chemical company, Milwaukee, USA; 100 mL.

16: 4-Bromostyrene, [2039-82-9], Aldrich chemical company, Milwaukee, USA; 25 g.

17: Vinylbenzyl chloride ([4-chloromethyl]styrene], [1592-20-7], Aldrich chemical company, Milwaukee, USA; 100 mL.

18: Styrene, [100-42-5], Aldrich chemical company, Milwaukee, USA; 100 mL.

PART F

Synthesis of Alkoxyamines

The following Scheme 6, in connection with Table 5, was followed in this Part F.

Scheme 6

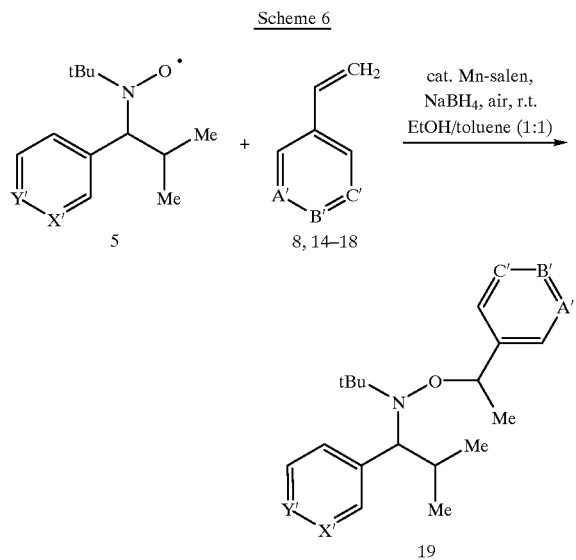

(III) chloride, which is commercially available), and styrene derivative 8 (1.299 g, 5.9 mmol) were added followed by 446 mg (11.8 mmol) of $NaBH_4$. Through the dark brown, cloudy reaction mixture was bubbled air for ca. 12 h at room temperature and the reaction mixture was stirred thoroughly. After this time most of the EtOH and toluene were evaporated, residual solvent was removed under reduced pressure. The dark brown residue was diluted with a mixture of EtOAc/hexanes (1:50) (20 mL) and sonicated for several minutes to yield a dark brown suspension which was filtered over silica gel. The filter residue was washed with hexanes and the filtrates were combined. The organics were washed with water and saturated aqueous NaCl-solution, dried over $MgSO_4$, filtrated, and evaporated under reduced pressure to yield dark brown viscous oil. The alkoxyamine was eluted from the residue by means of MPLC with EtOAc/hexanes (0:100 to 1:14) to yield 1.385 g (50%) of a colorless crystaline solid. $R_f$: 0.29 (EtOAc/hexanes=1:14, $UV_{254}$-quenching). Under the reaction conditions a transesterification from the methyl ester to the ethyl ester functionality occurred. $^1H$ NMR (300 MHz, $CDCl_3$, room temp., both diastereoisomers): δ8.64 (t, J=1.5 Hz, 1H, Ar-H), 8.58 (t, J=1.5 Hz, 1H, Ar-H), 8.33 (d, J=1.5, Hz, 2H, Ar-H), 8.22 (d, J=1.5, Hz, 2H, Ar-H), 7.47-7.40 (br. m, 4H, Ar-H, both diastereoisomers), 7.35-7.12 (br. m, 6H, Ar-H, both diastereoisomers), 5.20 (q, superimposed, J=6.6 Hz, 1H, $CHCH_3$), 5.10 (q, superimposed, J=6.6 Hz, 1H, $CHCH_3$), 4.53-4.36 (2q, superimposed, J=7.0 Hz, 8H, $OCH_2CH_3$), 3.42 (d, J=10.8 Hz, 1H, NCH), 3.28 (d, J=10.5 Hz, 1H, NCH), 2.50-2.20 (br. m, 1H, $CH(CH_3)_2$), 1.93-1.77 (br. m, 1H, $CH(CH_3)_2$), 1.68 (d, J=6.6 Hz, 3H, $CHCH_3$), 1.59 (d, J=6.6 Hz, 3H, $CHCH_3$), 1.42 (t, J=7.0 Hz, 6H, $OCH_2CH_3$), 1.40 (t, J=7.0 Hz, 6H, $OCH_2CH_3$), 1.24 (d, J=7.2 Hz, 3H, $CH(CH_3)_2$), 1.05 (s, 9H, $C(CH_3)_3$), 0.94 (d, J=6.6 Hz, 3H, $CH(CH_3)_2$), 0.87 (s, 9H, $C(CH_3)_3$), 0.53 (d, J=6.6 Hz, 3H, $CH(CH_3)_2$), 0.18 (d, J=6.3 Hz, 3H, $CH(CH_3)_2$) ppm. $^{13}C$ NMR (75 MHz, $CDCl_3$, room temp., one diastereoisomer): δ165.86, 146.49, 142.01, 131.50, 130.84, 130.77, 129.10,

TABLE 5

| entry | Nitroxide 5 | X' | Y' | "styrene" | A' | B' | C' | Alkoxy-anilne 19 | yield [%] |
|---|---|---|---|---|---|---|---|---|---|
| 1 | 5a | CH | CH | 8 | $CCO_2Et$ | CH | $CCO_2Et$ | 19a | 50 |
| 2 | 5a | CH | CH | 14 | CH | $CSO_3$-Neon-B | CH | 19b | 34 |
| 3 | 5a | CH | CH | 15 | CH | N | CH | 19c | 76 |
| 4 | 5a | CH | CH | 16 | CH | CBr | CH | 19d | 97 |
| 5 | 5a | CH | CH | 17 | CH | $CCH_2Cl$ | CH | 19e | 58 |
| 6 | 5c | N | CH | 18 | CH | CH | CH | 19f | 72 |
| 7 | 5c | CH | CBr | 18 | CH | CH | CH | 19g | 89 |
| 8 | 5c | CH | CBr | 16 | CH | CBr | CH | 19h | 98 |

"Styrene" in Table 5 refers to the styrene-like compounds that are used in this example and "styrene" is used simply for convenience. Also, "alkoxyamine" refers generally to the initiator control agent adducts, as used throughout this example.

Synthesis of Alkoxyamine 19a

A 100 mL round-bottomed flask equipped with a magnetic stirring bar and a PE stopper penetrated by a long stainless steel needle (air inlet) and two short needles (air outlet) was charged with the nitroxide 5a (1.542 g, 7.0 mmol). A mixture of EtOH/toluene (1:1) (40 mL), Jacobsen's Mn-salen complex (375 mg, 0.59 mmol; (N,N'-bis(3,5-di-tert-butylsalicylidene)-1,2-cyclohexanediaminato) managanese 127.39, 126.41, 82.70, 72.32, 61.21, 60.48, 31.95, 28.25, 24.30, 21.89, 21.15, 14.26 ppm.

Synthesis of Alkoxyamine 19b

By analogy to the procedure described above, 128 mg (0.58 mmol) of nitroxide 5a was reacted in 5 mL EtOH/toluene (1:1) with 222 mg (0.58 mmol) of styrene derivative (14) in the presence of Jacobsen's Mn-salen complex (55 mg, 0.087 mmol) and $NaBH_4$ (44 mg, 1.16 mmol) to yield 120 mg (34%) of a colorless viscous oil after purification by MPLC (silica gel, EtOAc/hexanes=1:4). $R_f$: 0.26 (EtOAc/hexanes=1:4, $Uv_{254}$-quenching). $^1H$ NMR (300 MHz, $CDCl_3$, room temp., both diastereoisomers): δ7.88 (d, J=8.1 Hz, 2H, Ar-H), 7.81 (d, J=8.4 Hz, 2H, Ar-H), 7.60 (d, J=8.4

Hz, 2H, Ar-H), 7.46 (d, J=8.1 Hz, 2H, Ar-H), 7.43-7.10 (br. m, 10H, Ar-H, both diastereoisomers), 4.99 (q, superimposed, J=6.6 Hz, 1H, CHCH$_3$), 4.97 (q, superimposed, J=6.6 Hz, 1H, CHCH$_3$), 4.45 (br. s, 2H, NH), 3.67 (s, superimposed, 2H, OCH$_2$(CH$_3$)$_2$), 3.66 (s, superimposed, 2H, OCH$_2$(CH$_3$)$_2$), 3.41 (d. J=10.8 Hz, 1H, NCH), 3.31 (d, J=10.8 Hz, 1H, NCH), 3.1-2.8 (br. m, 4H, CH$_2$CH$_2$N, both diastereoisomers), 2.4-2.2 (br. m, 1H, CH(CH$_3$)$_2$), 1.50-1.38 (br. m, superimposed, 5H, CH(CH$_3$)$_2$, CH$_2$CH$_2$N, both distereoisomers), 1.40 (s, superimposed 18H, OC(CH$_3$)$_3$), 1.27 (d, J=6.6 Hz, 3H, CH(CH$_3$)$_2$), 1.02 (s, 9H, C(CH$_3$)$_3$), 0.89 (d, superimposed, J=6.3 Hz, 3H, CH(CH$_3$)$_2$), 0.87 (s, superimposed, 6H, CH$_2$(CH$_3$)$_2$), 0.86 (s, superimposed, 6H, CH$_2$(CH$_3$)$_2$), 0.73 (s, 9H, C(CH$_3$)$_3$), 0.52 (d, J=6.6 Hz, 3H, CH(CH$_3$)$_2$), 0.21 (d, J=6.6 Hz, 3H, CH(CH$_3$)$_2$) ppm. $^{13}$C NMR (75 MHz, CDCl$_3$, room temp., both diastereoisomers): δ155.75, 152.09, 151.35, 141.97, 141.74, 134.48, 133.95, 130.78, 130.58, 128.09, 127.86, 127.81, 127.58, 127.44, 127.33, 126.84, 126.50, 126.35, 82.97, 81.96, 79.18, 77.93, 72.14, 72.08, 60.65, 60.50, 38.23, 36.17, 35.29, 33.58, 32.00, 31.85, 31.55, 28.50, 28.35, 28.14, 24.48, 23.71, 23.20, 21.91, 21.79, 21.04, 19.00, 18.20 ppm.

Synthesis of Alkoxyamine 19c

By analogy to the procedure described above, 661 mg (3.0 mmol) of nitroxide 5a were reacted in 30 mL EtOH/toluene (1:1) with 473 mg (4.5 mmol, 485 μL) of 4-vinylpyridine (15) in the presence of Jacobsen's Mn-salen complex (286 mg, 0.45 mmol) and NaBH$_4$ (227 mg, 6.0 mmol) to yield 747 mg (76%) of a dark yellow viscous oil after purification by MPLC (silica gel, EtOAc/hexanes=1:4). R$_f$: 0.26 (EtOAc/hexanes=1:4, UV$_{254}$-quenching). $^1$H NMR (300 MHz, CDCl$_3$, room temp., both diastereoisomers): δ8.65-8.44 (br. m, 4H, Ar- H), 7.48-7.30 (br. m, 4H, Ar-H), 7.29-7.10 (br. m, 10H, Ar-H), 4.96-4.81 (2q, superimpose J=6.6 Hz, CHCH$_3$), 3.41 (d, J=10.8 Hz, 1H, CHN), 3.33 (d, J=10.8 Hz, 1H, CHN), 2.28 (br. m, 1H, CH(CH$_3$)$_2$), 1.59 (d, J=6.6 Hz, 3H, CHCH$_3$), 1.52 (d, J=6.6 Hz, 3H, CHCH$_3$), 1.50-1.38 (br. m, superimposed, 1H, CH(CH$_3$)$_2$), 1.24 (d, J=7.2 Hz, 3H, CH(CH$_3$)$_2$), 1.02 (s, 9H, C(CH$_3$)$_3$), 0.93 (d, J=6.3 Hz, 3H, CH(CH$_3$)$_2$), 0.78 (s, 9H, C(CH$_3$)$_3$), 0.53 (d, J=6.6 Hz, 3H, CH(CH$_3$)$_2$), 0.25 (d, J=6.6 Hz, 3H, CH(CH$_3$)$_2$) ppm. $^{13}$C NMR (75 MHz, CDCl$_3$, room temp., both diastereoisomers): δ154.24, 153.41, 149.67, 142.00, 141.81, 130.78, 130.60, 127.40, 127.29, 126.44, 126.34, 121.74, 121.05, 82.40, 81.22, 72.16, 72.00, 65.76, 60.59, 60.52, 31.98, 31.88, 31.51, 28.31, 28.11, 24.34, 22.93, 22.57, 21.84, 21.72, 20.99, 15.20 ppm.

Synthesis of Alkoxyamine 19d

By analogy to the procedure described above, 1.54 g (7.0 mmol) of nitroxide 5a were reacted in 80 mL EtOH/toluene (1:1) with 2.56 g (14.0 mmol, 1.83 mL) of 4-bromostyrene (16) in the presence of Jacobsen's Mn-salen complex (670 mg, 1.05 mmol) and NaBH$_4$ (0.70 g, 14.0 mmol) to yield 2.77 g (97%) of a colorless viscous oil after purification by column chromatography (hexanes). R$_f$: 0.34 (hexanes 1:4, UV$_{254}$-quenching). $^1$H NMR (300 MHz, CDCl$_3$, room temp., both diastereoisomers): δ7.51-7.12 (m, superimposed, 18 H, Ar-H, both diastereoisomers), 4.91 (2q, superimposed, J=6.6 Hz, 2H, CHCH$_3$), 3.40 (d, J=10.8 Hz, 1H, NCH), 3.31 (d, J=10.8 Hz, 1H, NCH), 2.39-2.22 (br. m, superimposed, 1H, CH(CH$_3$)$_2$), 1.61 (d, J=6.6 Hz, 3H, CHCH$_3$), 1.51 (d, J=6.6 Hz, 3H, CH(CH$_3$)$_2$), 1.47-1.34 (br. m, superimposed, 1H, CH(CH$_3$)$_2$), 1.27 (d, J=6.6 Hz, 3H, CH(CH$_3$)$_2$), 1.03 (s, 9H, C(CH$_3$)$_3$), 0.93 (d, J=5.4 Hz, 3H, CH(CH$_3$)$_2$), 0.76 (s, 9H, C(CH$_3$)$_3$), 0.52 (d, J=6.6 Hz, 3H, CH(CH$_3$)$_2$), 0.25 (d, J=6.6 Hz, 3H, CH(CH$_3$)$_2$) ppm. $^{13}$C NMR (75 MHz, CDCl$_3$, room temp., both diastereoisomers): δ144.75, 144.69, 144.19, 143.94, 142.17, 141.98, 131.36, 131.18, 131.15, 130.93, 130.84, 130.74, 129.44, 129.26, 128.57, 127.85, 127.39, 127.24, 126.40, 126.26, 120.97, 120.38, 119.82, 119.59, 82.88, 81.92, 72.17, 60.48, 60.39, 46.49, 45.89, 34.65, 31.98, 31.76, 31.55, 28.38, 28.22, 25.27, 24.56, 23.16, 22.63, 22.03, 21.91, 21.13, 21.07, 20.71, 20.50, 18.55, 14.13 ppm.

Synthesis of Alkoxyamine 19e

By analogy to the procedure described above, 11.02 g (50.0 mmol) of nitroxide 5a were reacted in 200 mL EtOH/toluene (1:1) with 11.45 g (75.0 mmol, 10.57 mL) of (4-chloromethyl)styrene (17) in the presence of Jacobsen's Mn-salen complex (4.75 g, 7.5 mmol) and NaBH$_4$ (3.75 g, 100 mmol) to yield 11.00 g (58%) of a colorless viscous oil after purification by column chromatography (silica gel, hexanes). R$_f$: 0.34 (hexanes=1:4, UV$_{254}$-quenching). R$_f$: 0.28 (hexanes). $^1$H NMR (300 MHz, CDCl$_3$, room temp., both diastereoisomers): δ7.50-7.07 (m, superimposed, 18 H, Ar-H, both diastereoisomers), 4.91 (2q, superimposed, J=6.3 Hz, 2H, CHCH$_3$), 4.60 (br. s, 2H, CH$_2$Cl), 4.57 (br. s, 2H, CH$_2$Cl), 3.42 (d, J=10.8 Hz, 1H, NCH), 3.30 (d, J=10.8 Hz, 1H, NCH), 2.40-2.22 (br. m, superimposed, 1H, CH(CH$_3$)$_2$), 1.61 (d, J=6.6 Hz, 3H, CHCH$_3$), 1.53 (d, J=6.6 Hz, 3H, CHCH$_3$), 1.50-1.35 (br. m, 1H, CH(CH$_3$), 1.29 (d, J=6.6 Hz, 3H, CHCH$_3$), 1.04 (s, 9H, C(CH$_3$)$_3$), 0.91 (d, J=6.3 Hz, 3H, CHCH$_3$), 0.78 (s, 9H, C(CH$_3$)$_3$), 0.53 (d, J=6.3 Hz, CH(CH$_3$)$_2$), 0.22 (d, J=6.3 Hz, CH(CH$_3$)$_2$) ppm. $^{13}$C NMR (75 MHz, CDCl$_3$, room temp., both diastereoisomers): δ145.93, 145.05, 142.22, 135.66, 130.83, 129.36, 128.92, 128.53, 128.31, 128.11, 127.32, 127.22, 126.32, 126.15, 126.01, 83.10, 83.09, 72.10, 65.73, 60.35, 46.09, 46.03, 31.94, 28.49, 28.33, 28.15, 24.61, 21.87, 21.08, 15.42, 15.22 ppm.

Synthesis of Alkoxyamine 19f

By analogy to the procedure described above, 661 mg (3.0 mmol) of crude nitroxide 5b were reacted in 50 mL EtOH/toluene (1:1) with 781 mg (7.5 mmol, 860 μL) of styrene (18) in the presence of Jacobsen's Mn-salen complex (476 mg, 0.75 mmol) and NaBH$_4$ (374 mg, 10.0 mmol) to yield 1.169 mg (72%) of a slightly yellow viscous oil after purification by MPLC (silica gel, EtOAc/hexanes=1:4). R$_f$: 0.31 (EtOAc/hexanes=1:4, UV$_{254}$-quenching). $^1$H NMR (300 MHz, CDCl$_3$, room temp., both diastereoisomers): δ8.62-8.34 (br. m, 2H, Ar- H, both diastereoisomers), 7.88-7.82 (br. m, 1H, Ar-H, both diastereoisomers), 7.66-7.55 (br. m, 2H, Ar-H, both diastereoisomers), 7.32-7.15 (m, 10H, Ar-H, both diastereoisomers), 4.95-4.83 (2q, superimposed, 2H, CHCH$_3$, both diastereoisomers), 3.45 (d, J=11.1 Hz, 1H, CHN), 3.31 (d, J=10.8 Hz, 1H, CHN), 2.41-2.21 (br. m, 1H, CH(CH$_3$)$_2$), 1.62 (d, J=6.6 Hz, 3H, CHCH$_3$), 1.53 (d, J=6.6 Hz, 3H, CHCH$_3$), 1.31 (d, J=6.6 Hz, 3H, CH(CH$_3$)$_2$), 1.34-1.19 (br. m, superimposed, 1H, CH(CH$_3$)$_2$), 1.03 (s, 9H, C(CH$_3$)$_3$), 0.91 (d, J=6..3 Hz, 3H, CH(CH$_3$)$_2$), 0.77 (s, 9H, C(CH$_3$)$_3$), 0.53 (d, J=6.6 Hz, 3H, CH(CH$_3$)$_2$), 0.19 (d, J=6.6 Hz, 3H, CH(CH$_3$)$_2$) ppm. $^{13}$C NMR (75 MHz, CDCl$_3$, room temp., both diastereoisomers): δ151.69, 147.70, 147.48, 146.05, 145.17, 144.45, 138.20, 138.15, 137.70, 137.48, 128.99, 128.40, 128.14, 128.11, 127.54, 127.30, 127.03, 126.77, 126.08, 125.36, 122.69, 121.51, 83.59, 83.08, 70.18, 69.71, 69.53, 60.67, 60.50, 31.98, 31.44, 28.43, 28.27, 25.22, 24.52, 22.70, 21.98, 21.74, 20.98, 20.98 ppm.

Synthesis of Alkoxyamine 19g

By analogy to the procedure described above, 3.901 g (13.04 mmol) of nitroxide 5c were reacted in 100 mL EtOH/toluene (1:1) with 2.083 g (20.0 mmol, 2.29 mL) of styrene (18) in the presence of Jacobsen's Mn-salen complex (1.242 g, 1.96 mmol) and $NaBH_4$ (984 mg, 26.1 mmol) to yield 4.670 g (89%) of a pale yellow viscous oil after purification by MPLC (silica gel, EtOAc/hexanes=1:100). $R_f$: 0.26 (EtOAc/hexanes=1:4, $UV_{254}$-quenching). $^1H$ NMR (300 MHz, $CDCl_3$, room temp., both diastereoisomers): δ7.45-7.12 (m, superimposed, 18 H, Ar-H, both diastereoisomers), 4.90 (q, superimposed, J=6.3 Hz, 1H, $CHCH_3$), 4.89 (q, superimposed, J=6.3 Hz, 1H, $CHCH_3$), 3.39 (d, J=10.5 Hz, 1H, NCH), 3.27 (d, J=10.8 Hz, 1H, NCH), 2.38-2.20 (br. m, 1H, $CH(CH_3)_2$), 1.61 (d, J=6.6 Hz, 3H, $CH(CH_3)_2$), 1.54 (d, J=6.6 Hz, 3H, $CH(CH_3)_2$), 1.48-1.40-1.28 (br. m. superimposed, 1H, $CH(CH_3)_2$), 1.29 (d, J=6.6 Hz, 3H, $CHCH_3$), 1.05 (s, 9H, $C(CH_3)_3$), 0.92 (d, J=6.3 Hz, 3H, $CHCH_3$), 0.78 (s, 9H, $C(CH_3)_3$), 0.54 (d, J=6.6 Hz, $CH(CH_3)_2$), 0.21 (d, J=6.6 Hz, $CH(CH_3)_2$) ppm. $^{13}C$ NMR (75 MHz, $CDCl_3$, room temp., both diastereoisomers): δ145.46, 144.68, 141.50, 141.25, 132.57, 130.50, 130.29, 128.10, 127.41, 126.93, 126.71, 126.08, 120.33, 120.16, 83.53, 82.89, 71.48, 71.38, 60.55, 60.44, 31.95, 31.55, 28.43, 28.24, 24.63, 23.00, 22.03, 21.85, 21.05, 20.93 ppm.

Synthesis of Alkoxyamine 19h

By analogy to the procedure described above, 1.676 g (5.6 mmol) of nitroxide 5c were reacted in 600 mL EtOH/toluene (1:1) with 1.537 g (8.4 mmol, 1.1 mL) of 4-bromostyrene (16) in the presence of Jacobsen's Mn-salen complex (534 mg, 0.84 mmol) and $NaBH_4$ (420 mg, 10.2 mmol) to yield 2.652 g (98%) of a pale yellow viscous oil after purification by MPLC (silica gel, hexanes). $R_f$: 0.34 (hexanes, $UV_{254}$-quenching). $^1H$ NMR (300 MHz, $CDCl_3$, room temp., both diastereoisomers): δ7.60-7.11 (m, superimposed, 16 H, Ar-H), 4.92-4.86 (2q, superimposed), 2H, $CHCH_3$), 3.42 (d, J=10.5 Hz, 1H, NCN), 3.22 (d, J=10.5 Hz, 1H, NCH), 2.38-2.20 (br. m, 1H, $CH(CH_3)_2$), 1.61 (d, J=6.6 Hz, 3H, $CH(Ch_3)_2$), 1.55 (d, J=6.6 Hz, 3H, $CH(CH_3)_2$), 1.48-1.30 (br. m, superimposed, 1H, $CH(CH_3)_2$), 1.31 (d, J=6.0Hz, 3H, $CHCH_3$), 1.07 (s, 9H, $C(CH_3)_3$), 0.97 (d, J=6.3 Hz, 3H, $CHCH_3$), 0.81 (s, 9H, $C(CH_3)_3$), 0.57 (d, J=6.6 Hz, $CH(CH_3)_2$), 0.29 (d, J=6.6 Hz, $CH(CH_3)_2$), ppm. $^{13}C$ NMR (75 MHz, $CDCl_3$, room temp., both diastereoisomers): δ144.53, 143.75, 141.35, 141.12, 132.55, 132.47, 131.42, 131.30, 130.99, 130.59, 130.42, 129.52, 129.35, 128.61, 127.86, 121.17, 120.52, 120.45, 120.31, 83.03, 82.10, 71.50, 60.63, 60.54, 46.00, 34.70, 32.00, 31.78, 31.62, 28.46, 28.30, 25.31, 24.58, 23.09, 22.68, 21.96, 21.83, 21.05, 21.00 ppm.

PART G

Synthesis of the Biscarboxylate Substituted Alkoxyamine 20

The following Scheme 7 was followed in this part.

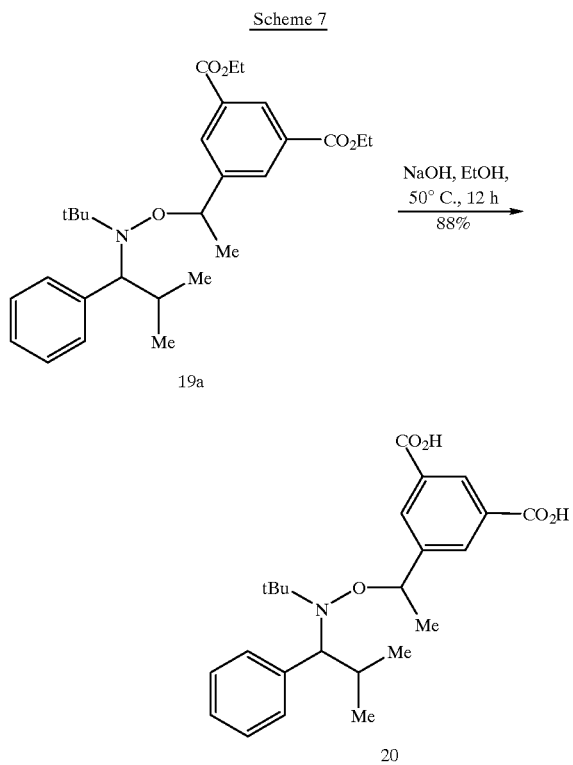

Scheme 7

Synthesis of the Biscarboxylate Substituted Alkoxyamine (20)

A 200 mL round bottomed flask equipped with a magnetic stir bar was loaded with 2.20 g (4.44 mmol) of the biscarboxyethyl functionalized alkoxyamine 19a. The compound was dissolved in 80 mL of a mixture of ethanol/water (1: 1) containing 1.20 g (30.0 mmol) of NaOH. The reaction mixture was stirred at 50° C. (oilbath) for 12 h during which the reaction mixture became homogeneous and clear. After complete consumption of the starting material (t.l.c.) the solvent was evaporated under reduced pressure. The remaining aqueous phase was acidified with a 10% aqueous $KHSO_4$-solution and extracted with diethyl ether (5×25 mL). The combined organic extracts were washed with brine (50 mL), dried over $MgSO_4$, filtered and the filtrate was evaporated under reduced pressure to yield 1.60 g (88%) of a colorless solid. $^1H$ NMR (300 MHz, $d^6$-DMSO, room temp., both diastereoisomers): δ13.25 (br. s, 2H, $CO_2H$), 8.43 (s, 1H, Ar-H), 8.36 (s, 1H, Ar-H), 8.31 (s, 2H, Ar-H), 8.12 (s, 1H, Ar-H), 5.07 (br. 2q, superimposed, J=6.0 Hz, 2H, $CHCH_3$, both diastereoisomers), 3.57 (d, J=10.5 Hz, 1H, NCH), 3.51 (d, J=10.5 Hz, 1H, NCH), 2.4-2.2 (br. m, 1H, $CH(CH_3)_2$), 1.61 (d, J=6.3 Hz, 3H, $CH(CH_3)_2$), 1.52 (d, J=6.3 Hz, $CH(CH_3)_2$), 1.36-1.20 (br. m, superimposed, H, $CH(CH_3)_2$), 1.30 (d, J=6.0 Hz, 3H, $CHCH_3$), 1.03 (s, 9H, $C(CH_3)_3$), 0.82 (d, J=6.3 Hz, 3H, $CHCH_3$), 0.72 (s, 9H, $C(CH_3)_3$), 0.50 (d, J=6.3 Hz, $CH(CH_3)_2$), 0.13 (d, J=6.3 Hz, $CH(CH_3)_2$) ppm. $^{13}C$ NMR (75 MHz, $d^6$-DMSO, room temp., both diastereoisomers): δ166.65, 146.25, 145.56, 144.85, 141.76, 141.50, 135.67, 133.54, 132.78, 131.93, 131.38, 131.30, 131.20, 131.05, 130.64, 129.21, 128.75, 127.42, 127.20, 126.51, 126.34, 121.96, 82.06, 81.26, 71.37, 71.08, 60.31, 60.09, 31.64, 31.28, 28.11, 27.97, 24.05, 22.55, 21.70, 21.64, 20.91, 20.77, 15.33 ppm.

PART H

Synthesis of the Sulfonate Substituted Alkoxyamine

The following Scheme 8 was followed in this part.

Scheme 8

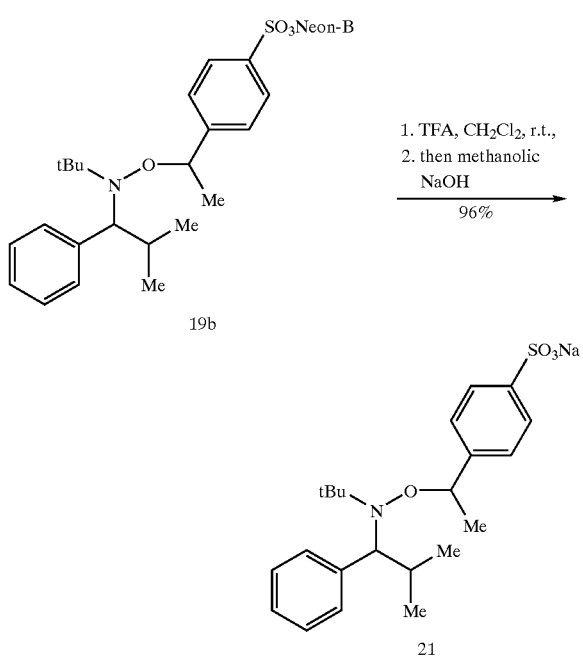

Synthesis of the Sulfonate Substituted Alkoxyamine (21)

According to a protocol of J. C. Roberts, et al. (*Tetrahedron Lett.* 1997, 38, 355–358; WO 96/18609), an ovendried 25 mL Schlenk-flask equipped with a magnetic stirr bar and a rubber septum was loaded under an atmosphere of argon with 125 mg (0.21 mmol) of alkoxyamine 19b. The compound was dissolved in 4.75 mL of anhydrous MeOH. Trifluoroacetic acid (250 µL) was added and the reaction mixture was stirred at room temp. for 2 h (The reaction mixture became clear and homogeneous after five minutes.) The solvent was evaporated under reduced pressure followed by treatment of the colorless residue with 21 mL of a dilute methanolic NaOH-solution (c=0.01 mol L$^{-1}$) to provide 85 mg (96%) of the corresponding sodium salt after evaporation of the solvent and generated 3,3-dimethylpyrrolidine under reduced pressure. The crude reaction product was used without further purification and analysis.

PART I

Synthesis of the Carboxylate or Sulfonate Substituted Alkoxyamines

The following Scheme 9 was following in connection with Table 6:

Scheme 9

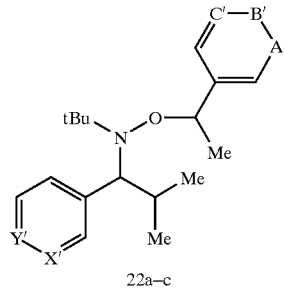

TABLE 6

| Entry | alkoxy-amine 19 | Alkoxy-amine 22 | X' | Y' | A' | B' | C' | yield [%] |
|---|---|---|---|---|---|---|---|---|
| 1 | 19g | 22a | CH | CCO$_2$H | CH | CH | CH | 97 |
| 2 | 19g | 22b | CH | CSO$_3$Li | CH | CH | CH | 82 |
| 3 | 19h | 22c | CH | CCO$_2$H | CH | CCO$_2$H | CH | 95 |

Synthesis of the Carboxylate Substituted Alkoxyamine 22a

An ovendried 100 mL Schlenk-flask equipped with a magnetic stirring bar and a rubber septum was charged under argon atmosphere with 1.19 g (2.96 mmol) the alkoxyamine 19 g. The compound was dissolved in 20 mL of anhydrous diethylether at room temp. The solution was cooled to −78° C. (dry ice/isopropanol bath) and 3.83 mL (6.51 mmol) of a 1.7 M solution of tert-butyllithium in pentane is added dropwise via a syringe. The reaction mixture turned yellow and was kept at this temperature for ca. 1 hour. A stream of pre-dried (by H$_2$SO$_4$) carbondioxide was passed through the solution at this temperature. Stirring and gasfeed was continued for additional 3 h with warming to room temperature to yield an almost colorless reaction mixture. The reaction was quenched with 10 mL of water and he aqueous phase was acidified with a 10% aqueous KHSO$_4$-solution. After dilution with diethyl ether and phase separation, the aqueous phase was extracted with diethyl ether (3×30 mL). The combined organic extracts were washed with brine (50 mL), dried over MgSO$_4$, filtered and the filtrate was evaporated under reduced pressure to yield 1.06 g (97%) of a colorless solid. $^1$H NMR (300 MHz, d$^6$-DMSO, room temp., both diastereoisomers): δ12.65 (br. s, 2H, CO$_2$H), 7.87 (d, J=8.4 Hz, 2H, Ar-H), 7.55 (d, J=8.4 Hz, 2H, Ar-H), 7.65-7.11 (br. m, 14 H, Ar-H, both diastereoisomers), 4.86 (2q, superimposed, 2H, CHCH$_3$, both diastereoisomers), 3.53 (d, J=10.5 Hz, 1H, NCH), 3.40 (d, J=10.5 Hz, 1H, NCH), 2.36-2.22 (br. m, 1H, CH(CH$_3$)$_2$), 1.55 (d, J=6.6 Hz, 3H, CH(CH$_3$)$_2$), 1.46 (d, J=6.6 Hz, CH(CH$_3$)$_2$), 1.37-1.20 (br. m, superimposed, 4H, CH(CH$_3$)$_2$, CHCH$_3$), 0.99 (s, 9H, C(CH$_3$)$_3$), 0.86 (d, J=6.3 Hz, 3H, CHCH$_3$), 0.73 (s, 9H, C(CH$_3$)$_3$), 0.47 (d, J=6.3 Hz, CH(CH$_3$)$_2$), 0.13 (d, J=6.6 Hz, CH(CH$_3$)$_2$) ppm. $^{13}$C NMR (75 MHz, d$^6$-DMSO, room temp., both diastereoisomers): δ179.30, 167.40, 167.35, 147.35, 147.15, 144.91, 144.17, 130.79, 128.92, 128.72, 128.35, 128.07, 128.01, 127.44, 126.89, 126.74, 125.89, 82.86, 82.30, 77.20, 72.01, 70.82, 70.70, 60.22, 60.11, 37.65, 35.81, 31.40, 30.94, 28.04, 27.85, 27.66, 24.19, 22.59, 21.84, 21.52, 20.61 ppm.

Synthesis of the Lithiosulfonate Substituted Alkoxyamine 22b

By analogy to the procedure described above, 809 mg (2.0 mmol) of alkoxyamine 19g were reacted in 20 mL of anhydrous diethyl ether with 2.6 mL of a 1.7 M solution of tert-butyllithium in pentane. The intermediate lithio derivative of 19 g was reacted at −78° C. with 0.33 g (2.4 mmol) of $SO_3.NMe_3$ complex, followed by warming to room temperature to yield a colorless precipitate. The reaction was quenched by addition of 5 mL of aqueous tetrahydrofurane (THF) containing 10 mg (0.4 mmol) of LiOH. After evaporation of the solvent under reduced pressure, the residue was dissolved in 3 mL of dichloromethane and filtered off from insoluble lithium salts. After evaporation of the dichloromethane under reduced pressure, 1.04 g (82%) of the lithiosulfonate substituted alkoxymine 22b were obtained as a colorless solid. IR (film on polyethylene): $v=1208\ cm^{-1}$, br. vs, $—SO_3^-$. $^1H$ NMR (300 MHz, $d^6$-DMSO, room temp., both diastereoisomers): δ7.51-7.17 (br. m, 18 H, Ar-H, both diastereoisomers), 4.87 (2q, superimposed, J=6.6 Hz, 2H, $CHCH_3$, both diastereoisomers), 3.47 (d, J=10.5 Hz, 1H, NCH), 3.40-3.30 (br. HDO-peak, superimposed, 1H, NCH), 2.35-2.20 (br. m, 1H, $CH(CH_3)_2$), 1.56 (d, J=6.3 Hz, 3H, $CH(CH_3)_2$), 1.47 (d, J=6.6 Hz, $CH(CH_3)_2$), 1.35-1.25 (br. m, superimposed, 4H, $CH(CH_3)_2$, $CHCH_3$), 1.01 (s, 9H, $C(CH_3)_3$), 0.88 (d, J=6.3 Hz, 3H, $CHCH_3$), 0.75 (s, 9H, $C(CH_3)_3$), 0.48 (d, J=6.6 Hz, $CH(CH_3)_2$), 0.15 (d, J=6.3 Hz, $CH(CH_3)_2$) ppm. $^{13}C$ NMR (75 MHz, $d^6$-DMSO, room temp., both diastereoisomers): δ146.26, 146.04, 145.07, 144.27, 142.22, 141.99, 130.03, 128.32, 128.13, 128.06, 127.45, 126.93, 126.74, 125.93, 124.61, 124.37, 82.68, 81.97, 70.76, 70.68, 60.13, 56.03, 48.60, 44.20, 31.53, 31.17, 28.160, 27.94, 24.32, 22.70, 21.96, 21.64, 20.76, 18.55 ppm.

Synthesis of the Biscarboxylate Substituted Alkoxyamine 22c

By analogy to the procedure described above, 1.256 g (2.6 mmol) of alkoxyamine 19 h were reacted in 20 mL of anhydrous diethyl ether with 6.50 mL of a 1.7 M solution of tert-butyllithium in pentane. The intermediate lithio derivative of 19 h was reacted with gaseous carbondioxide to yield 1.04 g (95%) of the biscarboxylate substituted alkoxymine 22c as a colorless solid. $^1H$ NMR (300 MHz, $d^6$-DMSO, room temp., both diastereoisomers): δ12.65 (br. s, 2H, $CO_2H$), 7.60-7.1 (br. m, 10 H, Ar-H, both diastereoisomers), 5.08-4.85 (2q, superimposed, 2H, $CHCH_3$, both diastereoisomers), 3.57 (d, J=10.5 Hz, 1H, NCH), 3.44 (d, J=10.5 Hz, 1H, NCH), 2.4-2.3 (br. m, 1H, $CH(CH_3)_2$), 1.58 (d, J=6.6 Hz, 3H, $CH(CH_3)_2$, major diastereoisomer), 1.48 (d, J=6.6 Hz, $CH(CH_3)_2$), 1.36-1.20 (br. m, superimposed, 4H, $CH(CH_3)_2$, $CHCH_3$), 1.01 (s, 9H, $C(CH_3)_3$), 0.87 (d, J=6.3 Hz, 3H, $CHCH_3$), 0.73 (s, 9H, $C(CH_3)_3$), 0.49 (d, J=6.3 Hz, $CH(CH_3)_2$), 0.15 (d, J=6.3 Hz, $CH(CH_3)_2$) ppm. $^{13}C$ NMR (75 MHz, $d^6$-DMSO, room temp., both diastereoisomers): δ179.38, 167.49, 167.43, 167.23, 151.02, 149.94, 149.09, 147.31, 147.09, 130.83, 130.01, 129.42, 129.08, 128.89, 128.52, 128.32, 127.56, 126.98, 126.01, 82.87, 81.92, 70.95, 60.30, 60.22, 37.72, 31.52, 31.29, 31.14, 28.10, 27.90, 27.73, 27.03, 25.48, 24.14, 22.63, 21.78, 21.54, 20.65 ppm.

PART J

Synthesis of the Aminomethyl-functionalized Alkoxyamine

The following Scheme 10 was followed in this part.

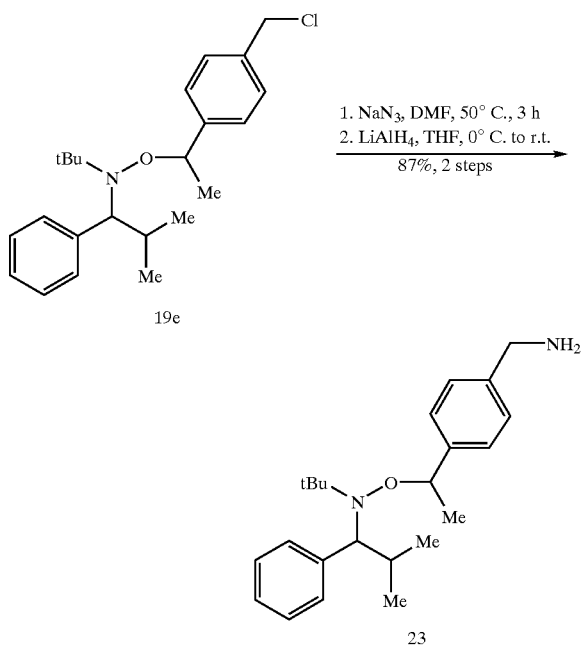

Scheme 10

Synthesis of the Azidomethyl-functionalized Alkoxyamine

According to the protocol from C. J. Haker, et al., (*J. Polym. Sci. Part A: Pol. Chem.* 1998, 36, 2161–2167), a 100 mL ovendried Schlenk-flask equipped with a magnetic stirring bar and a rubber septum was charged under argon atmosphere with the chloromethyl functionlized alkoxyamine (19e) (2.00 g, 5.34 mmol) and sodium azide ($NaN_3$) (694 mg, 10.68 mmol). The reactants were dissolved in 20 mL of anhydrous dimethylformanide (DMF) and heated under an atmosphere of argon to 50° C. for 3 h. The reaction course was monitored by t.l.c. After complete consumption of the starting material, the reaction mixture was quenched with 100 mL of water. The aqueous phase was diluted with diethyl ether (50 mL) and was then extracted with diethyl ether (3×50 mL). The combined organic extracts were successively washed with water (50 mL) and brine (50 mL) and dried over $MgSO_4$. After filtration and evaporation of the solvent under reduced pressure, the 2.3 g (quant.) were obtained which were used without further purification in the next step. $R_f$: 0.19 (hexanes). $^1H$ NMR (300 MHz, $CDCl_3$, room temp., both diastereoisomers): δ7.61-7.15 (br. m, 18H, Ar-H, both diastereoisomers), 5.10-4.95 (br. 2q, superimposed, J=6.6 Hz, 2H, $CHCH_3$, both diastereoisomers), 3.69 (s, superimposed, 2H, $CHHN_3$), 4.38 (s, superimposed, 2H, $CHHN_3$), 3.52 (d, J=10.5 Hz, 1H, NCH), 3.40 (d, J=10.8 Hz, 1H, NCH), 2.60-2.33 (br. m, 1H, $CH(CH_3)_2$), 1.72 (d, J=6.6 Hz, 3H, $CH(CH_3)_2$), 1.63 (d, J=6.6 Hz, $CH(CH_3)_2$), 1.55-1.42 (br. m, superimposed, H, $CH(CH_3)_2$), 1.41 (d, J=6.3 Hz, 3H, $CHCH_3$), 1.15 (s, 9H, $C(CH_3)_3$), 1.01 (d, J=6.3 Hz, 3H, $CHCH_3$), 0.87 (s, 9H, $C(CH_3)_3$), 0.65 (d, J=6.6 Hz, $CH(CH_3)_2$), 0.26 (d, J=6.6 Hz, CH(CH$_3$)$_2$) ppm. $^{13}$C-NMR: (75 MHz, CDCl$_3$, room temp., both diastereoisomers): δ134.65, 134.12, 131.43, 131.35, 129.21, 129.17, 128.59, 128.52, 127.97, 127.87, 127.71, 127.13, 126.86, 126.69, 83.64, 83.00, 72.70, 72.61, 61.05, 60.89, 55.10, 55.06, 32.50, 32.13, 28.86, 28.69, 24.99, 23.55, 22.54, 22.43, 21.64, 21.35 ppm.

Synthesis of the Aminomethyl-functionalized Alkoxyamine 23

A 100 mL ovendried Schlenk-flask equipped with a magnetic stirring bar and a rubber septum was charged under argon atmosphere with the crude azidomethyl functionlized alkoxyamine (ca. 2.3 g, ca. 5.2 mmol) and the compound was dissolved in 20 mL of anhydrous tetrahydrofurane (THF). 5.5 mL of a 1 M solution of LiAlH$_4$ in Et$_2$O was added dropwise with a syringe at 0° C. (icebath) and stirring was continued for 12 h with warming to room temp. The reaction was quenched by successive addition of water (0.1 mL), 5% aqueous NaOH-solution (0.1 mL), and water (0.1 mL). Diethylether (50 mL) was added to the reaction mixture and the resulting colorless Al-containing precipitate was filtered off with a glass-sintered funnel. The filter cake was washed thoroughly with diethyl ether. The combined filtrates were successively washed with water (50 mL), and brine (50 mL) and dried over MgSO$_4$. After filtration and evaporation of the solvent under reduced pressure, the crude product was purified by MPLC (silica gel, EtOAc/hexanes= 3:1) to yield 1.55 g (87% from 19e) of a pale yellow to colorless viscous oil. R$_f$: 0.37 (EtOAc/hexanes=3:1+2 vol-% Et$_3$N, UV$_{254}$-quenching and ninhydrine stain). $^1$H NMR (300 MHz, d$^6$-benzene, room temp., both diastereoisomers): δ7.75-7.10 (br. m, 22H, Ar-H, CH$_2$NH$_2$, both diastereoisomers), 5.18-4.95 (br. 2q, superimposed, J=6.6 Hz, 2H, CHCH$_3$, both diastereoisomers), 3.69 (s, superimposed, 2H, CHHNH$_2$), 3.66 (s, superimposed, 2H, CHHNH$_2$), 3.53 (d, J=10.5 Hz, 1H, NCH), 3.45 (d, J=10.8 Hz, 1H, NCH), 2.63-2.47 (br. m, 1H, CH(CH$_3$)$_2$), 1.72 (d, J=6.6 Hz, 3H, CH(CH$_3$)$_2$), 1.65 (d, J=6.6 Hz, CH(CH$_3$)$_2$), 1.62-1.50 (br. m, superimposed, H, CH(CH$_3$)$_2$), 1.51 (d, J=6.3 Hz, 3H, CHCH$_3$), 1.21 (s, 9H, C(CH$_3$)$_3$), 1.15 (d, J=5.1 Hz, 3H, CHCH$_3$), 0.99 (s, 9H, C(CH$_3$)$_3$), 0.76 (d, J=6.6 Hz, CH(CH$_3$)$_2$), 0.45 (d, J=6.3 Hz, CH(CH$_3$)$_2$) ppm. $^{13}$C NMR (75 MHz, d$^6$-benzene, room temp., both diastereoisomers): δ144.24, 143.51, 142.74, 142.68, 142.62, 131.27, 131.23, 127.85, 127.24, 127.14, 126.85, 126.68, 126.43, 83.93, 83.07, 72.71, 60.68, 60.61, 46.45, 32.38, 32.09, 28.64, 28.50, 24.91, 23.48, 22.56, 22.24, 21.40, 21.39 ppm.

PART K

Synthesis of the Hydroxy-functionalized Alkoxyamine

The following Scheme 11 was followed in this part.

Scheme 11

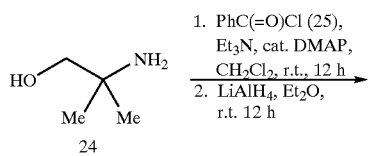

1. PhC(=O)Cl (25), Et$_3$N, cat. DMAP, CH$_2$Cl$_2$, r.t., 12 h
2. LiAlH$_4$, Et$_2$O, r.t. 12 h

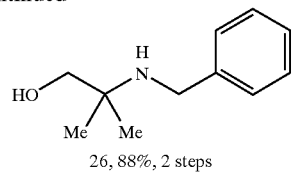

26, 88%, 2 steps 26
1. cat. Na$_2$WO$_4$ × 2 H$_2$O, H$_2$O$_2$, MeOH, 0° C. to r.t., 3 h (66%)
2. TBSCl (27), Et$_3$N, cat. DMAP, CH$_2$Cl$_2$, r.t., 12 H (82%)

54%, 2 steps

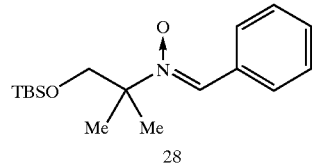

28

28
1. iPrMgCl (4), THF, 0° to r.t., 12 h (82%)
2. cat. Cu(OAc)$_2$, NH$_4$OH, MeOH, air, r.t. (80%)

66%, 2 steps

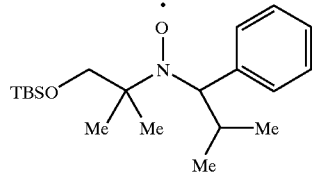

29

29 → TBAF, THF, r.t., 3 h, 78% → 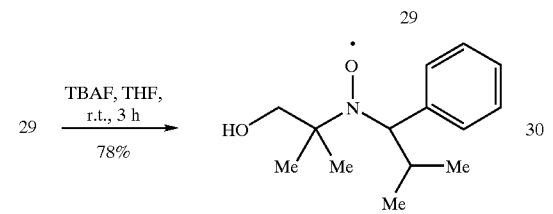

30

K.1: Synthesis of the Benzylamine 26

A 500 mL ovendried Schlenk-flask equipped with a magnetic stir bar and rubber septum was charged under an atmospere of argon with 4.46 g (50.0 mmol) of the aminoalcohol 24. The compound was dissolved in 250 mL of anhydrous dichloromethane and 10. 12 g (100 mmol, 13.94 mL) of triethylamine (Et$_3$N) and 611 mg (5.0 mmol) of dimethylaminopyridine DMAP) were added. After cooling to 0° C. (icebath), benzoylchloride (25) was added dropwise with a syringe. The reaction mixture was stirred at room temp. for two hours and the reaction course was monitored by t.l.c. After complete conversion, dichloromethane was evaporated under reduced pressure, the residue was dissolved in EtOAc (200 mL) and 100 mL of an aqueous 5% KHSO$_4$-solution were added. After phase separation, the aqueous phase was extracted with EtOAc (2×100 mL) and the combined organic extracts were washed successively with aqueous 5% KHSO$_4$-solution (2×100 mL), saturated aqueous NaHCO$_3$-solution (100 mL), water (100 mL) and brine (100 mL). The solution was dried over MgSO$_4$, filtered off and the solvent was evaporated under reduced pressure to yield ca. 9.6 g (>95%) of the benzamide as a colorless solid of sufficient purity for the next step according to NMR, GC/MS and t.l.c. analysis. R$_f$: 0.24 (EtOAc/hexanes=1:1, UV$_{254}$-quenching). $^1$H NMR (300 MHz, CDCl$_3$, room temp.): δ7.71-7.67 (m, 2H, Ar—H), 7.49-7.35 (m, 3H, Ar-H), 6.29 (s, 1H, NH), 4,82 (t, J=6.0, 1H, OH), 3.64 (d, J=6.0, 2H, CH$_2$), 1.38 (s, 6H, CH$_3$) ppm. $^{13}$C NMR (75 MHz, CDCl$_3$, room temp.): δ168.37, 134.80, 131.53, 128.52, 126.85, 70.63, 56.34, 24.56 ppm.

A 1000 mL ovendried Schlenk-flask equipped with a magnetic stir bar and rubber septum was charged under an atmospere of argon with ca. 9.6 g (50.0 mmol) of the benzamide. The compound was dissolved in 250 mL of anhydrous diethylether. After cooling to 0° C. (icebath), a 1.0 M solution of LiAlH$_4$ in diethylether (100 mL) was added dropwise with a syringe. The reaction mixture was stirred with warming to room temp. for 24 hours and then heated to reflux for additional four hours. The reaction course was monitored by t.l.c. After complete conversion, the reaction was quenched by successive addition of 4.2 mL of water, 4.2 mL of an aqueous 5% NaOH-solution, followed by additional 4.2 mL of water. The colorless precipitate is filtered off by a glass-sintered funnel and the filtercake was washed thoroughly with diethylether. The combined organic filtrates were evaporated under reduced pressure to yield 7.90 g (88%, 2 steps) of pure amine 26 as a colorless solid. R$_f$: 0.31 (EtOAc/hexanes=2:1+2% NEt$_3$, UV$_{254}$-quenching). $^1$H NMR (300 MHz, CDCl$_3$, room temp.): δ7.60-7.20 (m, 5H, Ar-H), 4.69 (s, 1H, OH), 3.72 (s, 2H, CH$_2$OH), 3.38 (s, 2H, CH$_2$N), 2.27 (br. s, 1H, NH), 1.20 (s, 6H, C(CH$_3$)$_2$) ppm. $^{13}$C NMR (75 MHz, CDCl$_3$, room temp.): δ140.74, 128.43, 128.31, 128.15, 127.23, 126.97, 68.35, 53.92, 46.40, 24.13 ppm.

K.2: Synthesis of the Nitrone 28

According to a protocol of S. -I. Murashi, et al. (*J. Org. Chem.* 1990, 55, 1736–1744), in a 50 mL flask equipped with a magnetic stir bar were placed 896 mg (5.0 mmol) of the benzylic amine 26, 66 mg (0.2 mmol) of Na$_2$WO$_4$.2H$_2$O and 10 mL of MeOH. The reaction mixture was cooled to 0° C. (icebath) and 1.7 g (15.0 mmol, of a 30% aqueous H$_2$O$_2$-solution was added dropwise with syringe. After complete addition, the reaction mixture was warmed to room temp. and stirred for three hours. The reaction course was followed by t.l.c. Methanol was evaporated under reduced pressure and the residue was diluted in dichloromethane (50 mL). After phase separation, the organic phase was washed with brine (20 mL), dried over MgSO$_4$, filtered and evaporated under reduced pressure. The residue was purified by MPLC (silica gel EtOAc/hexanes=2:1) to yield 638 mg (66%) of the intermediate hydroxyfunctionalized nitrone as a colorless solid. R$_f$: 0.20 (EtOAc/hexanes=2:1, UV$_{254}$-quenching). $^1$H NMR (300 MHz, d$^6$-benzene, room temp.): δ8.40 (d, J=7.8 Hz, 2H, Ar-H), 7.29-7.14 (m, 4H, Ar-H, CH(=N)), 4.82 (t, J=5.7 Hz, 1H, OH), 3.72 (d, J=5.7 Hz, 2H, CH$_2$OH), 1.24 (s, 6H, C(CH$_3$)$_2$) ppm. $^3$C NMR (75 MHz, d$^6$-benzene, room temp.): δ131.58, 131.42, 130.29, 129.42, 128.52, 73.27, 69.21, 23.32 ppm.

A 100 mL ovendried Schlenk-flask equipped with a magnetic stir bar and rubber septum was charged under an atmospere of argon with 2.51 g (13.0 mmol) of the intermediate hydroxyfunctionalized nitrone. The compound was dissolved in 50 mL of anhydrous dichloromethane, 1.97 g (19.5 mmol, 2.72 mL) of triethylamine (Et$_3$N), and 2.55 g (16.9 mmol) of tert-butyldimethylchlorosilane (TBSCl) were added followed by 160 mg (1.3 mmol) of dimethylaminopyridine DMAP). The reaction mixture was stirred at room temp. for four hours and the reaction course was monitored by t.l.c. After complete conversion, dichloromethane was evaporated under reduced pressure, the residue was dissolved in diethylether (100 mL) and 20 mL of an aqueous 5% KHSO$_4$-solution were added. After phase separation, the aqueous phase was extracted with diethylether (2×50 mL) and the combined organic extracts were washed successively with aqueous 5% KHSO$_4$-solution (2×50 mL), saturated aqueous NaHCO$_3$-solution (50 mL), water (50 mL) and brine (50 mL). The etheral solution was dried over MgSO$_4$, filtered and the solvent was evaporated under reduced pressure. Purification by MPLC (silica gel, EtOAc to yield ca. 9.6 g (>95%) of the benzamide as a colorless solid of sufficient purity for the next step. R$_f$: 0.34 (EtOAc/hexanes=1:4, UV$_{254}$-quenching). $^1$H NMR (300 MHz, CDCl$_3$, room temp.): δ8.29-8.20 (m, 2H, Ar- H), 7.50 (s, 1H, CH(=N)), 7.44-7.31 (m, 3H, Ar-H), 3.79 (s, 2H, CH$_2$OH), 1.53 (s, 6H, C(CH$_3$)$_2$), 0.81 (s, 9H, SiC(CH$_3$)$_3$), −0.02 (s, 6H, Si(CH$_3$)$_2$) ppm. $^{13}$C NMR (75 MHz, CDCl$_3$, room temp.): δ132.01, 131.00, 129.94, 128.82, 128.30, 74.12, 68.25, 25.70, 23.03, 18.09, −5.60 ppm.

K.3: Synthesis of the Nitroxide 29

According to a protocol of R. Braslau, C. J. Hawker, et al. (*J. Am. Chem. Soc.* 1999, 121, 3904–3921) and the general synthetic protocol described for the synthesis of alkoxyamines 19, in an ovendried 100 mL Schlenk-flask equipped with a magnetic stir bar and a rubber septum were placed 3.488 g (11.4 mmol) of the protected nitrone 28. The chemical was dissolved in 40 mL of anhydrous tetrahydrofurane (THF) and the solution was cooled to 0° C. (icebath). 11.4 mL of a 2 M solution of isopropylmagnesium chloride (4) were added dropwise at this temperature and stirring was continued with warming to room temp. for 12 hours. The reaction mixture was quenched with a saturated aqueous NH$_4$Cl-solution (20 mL) and the THF was evaporated under reduced pressure. The reaction mix was diluted with diethyl ether (100 mL) and water (30 mL). After phase separation, the aqueous phase was extracted with diethyl ether (2×50 mL) and the combined organic extracts were washed successively with water (50 mL) and brine (50 mL), dried over MgSO$_4$, filtered and evaporated under reduced pressure to yield ca. 3.3 g (82%) of the crude hydroxylamine as an orange oil which was used directly without further purification in the next step. The crude material contained some of the corresponding nitroxide due to air oxidation during the work-up procedure. R$_f$: 0.65 (EtOAc/hexanes=1:9, UV$_{254}$-quenching).

According to a protocol of R. Braslau, C. J. Hawker, et al. (*J. Am. Chem. Soc.* 1999, 121, 3904–3921), and the general synthetic protocol described for the synthesis of alkoxyamines 19, 3.3 g (9.4 mmol) of the crude intermediate hydroxylamine, dissolved in a mixture of MeOH (50 mL) and 28% aqueous NH$_4$OH-solution (10 mL) were air-oxidized in the presence of 85 mg (0.47 mmol) of Cu(OAc)$_2$ to yielded the crude nitroxide as a dark red oil. Purification by medium pressure liquid chromatography (MPLC) (silica gel, EtOAc/hexanes=1:20) yielded 2.62 g (80%) of the nitroxide. R$_f$: 0.53 (EtOAc/hexanes=1:16, visible yellow spot, UV$_{254}$-quenching).

K.4: Synthesis of the Nitroxide 30

In an 50 mL round bottomed flask equipped with a magnetic stir bar and a rubber septum were placed 1.195 g (3.13 mmol) of the protected nitroxide 29. Successively, 15 mL of tetrahydrofurane (THF) and 3.76 mL (3.76 mmol) of tetra butylammonium fluoride (1.0 M solution in tetrahydrofurane (THF)) were added. The solution was then stirred at room temp. for one hour. The reaction mixture was quenched with water (15 mL) and the tetrahydrofurane (THF) was evaporated under reduced pressure. The reaction mixture was diluted with diethyl ether (30 mL) and ethyl acetate (5 mL). After phase separation, the aqueous phase was extracted with diethyl ether (2×30 mL) and the combined organic extracts were washed successively with water (50 mL) and brine (50 mL), dried over MgSO$_4$, filtered and evaporated under reduced pressure to yield the crude nitroxide. Purification by medium pressure liquid chromatography (MPLC) (silica gel, EtOAc/hexanes=1:5) yielded 0.58 g (78%) of the nitroxide 30. R$_f$: 0.30 (EtOAc/hexanes=1:4, visible yellow spot, UV$_{254}$-quenching). IR (film on polyethylene): ν=3417 cm$^{-1}$, br. vs, —OH.

Example 2: Reaction of 5,5-Dimethyl-Δ$^1$-pyrroline N-oxide with AIBN

Scheme 12

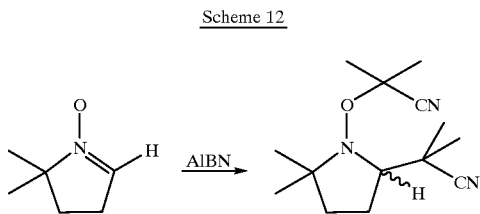

A 25 mL oven dried Schlenk flask equipped with stirring bar and rubber septum was charged under argon with 620 mg (5.9 mmol) of 5,5-dimethyl-Δ$^1$-pyrroline N-oxide (Aldrich, Milwaukee, Wis.) and 1.94 g (11.8 mmol) of azobisisobutyrodinitrile (AIBN). 2 mL of deoxygenated xylene were added and the stirred reaction mixture was heated under argon to 105–110° C. until the evolution of nitrogen ceased. Xylene was evaporated in vacuo and 1 mL of petroleum ether was added to the reaction mixture to yield an orange solution. 5 mL of MeOH were added under vigorous stirring and after phase separation and removal of the supernatant, the methanolic layer was partially concentrated and placed in a refrigerator at approximately −20° C. causing colorless crystals to form. Excess MeOH was removed and the residue was dissolved in approximately 2 mL of MeOH under gentle heating. The solution was again cooled to approximately −20° C. and, after collection, the crystals were dried in vacuo to yield 401 mg (27%) of the desired compound. TLC (1:9 EtOAc/hexanes): R$_f$=0.60; $^1$H NMR (300 MHZ, CDCl$_3$): δ=1.22 (s, 3H, CH$_3$), 1.34 (s, 3H, CH$_3$), 1.37 (s, 3H, CH$_3$), 1.43 (s, 3H, CH$_3$), 1.4–1.7 (m, superimposed, 3H, CH$_2$CHHCH), 1.74 (s, 3H, CH$_3$), 1.76 (s, 3H, CH$_3$), 1.95 (dq, J=12.0, 9.6 Hz, 1H, CH$_2$CHHCH), 3.30 (dd, J=10.1, 5.9 Hz, 1H, CH$_2$CHHCH) ppm; $^{13}$C NMR (75 MHZ, CDCl$_3$): δ=20.85, 21.60, 22.03, 24.96, 26.09, 28.44, 34.90, 37.31, 39.34, 66.37, 72.33, 73.86, 121.39, 126.01 ppm.

Example 3: Comparison: TEMPO in Emulsion Polymerization

Twelve (12) separate emulsion polymerization conditions were conducted with three different initiators, all at 90° C. for 15 h (a total of 36 experiments). Each polymerization was set up with a total volume 0.7 mL, with 20 weight % styrene (monomer). The amount of surfactant (sodium alpha (C$_{14}$–C$_{16}$) olefin sulfonate—sold by Rhodia as Rhodacal A-246/L) added was 1 weight % to monomer, and the amount of initiator added was 0.001 mole equivalence to monomer. The initiators that were used were water soluble and were (1) potassium persulfate, (2) tert-butylhydroperoxide (TBHP) and (3) 2,2-azobis(N,N'-dimethyleneisobutyramidine) dihydrochloride (sold by E.I. du Pont de Nemours and Company under the trademark VAZO® 044). For each initiator the series of 12 polymerizations differed in the amount of control agent added, with the first well getting no control agent and the last well getting 3.3 mole equivalence of control agent, with even steps of 0.3 mole equivalence (the control agent used was 2,2,6,6-tetramethyl-1-piperidinoxyl radical—"TEMPO"). After the predetermined heating and agitation time and temperature the polymerization mixtures were worked up and characterized using the standard procedure outlined for polymerization experiments at the beginning of the Example section.

FIGS. 1A and 1B plot the results of the above experiments for TBHP and demonstrate that with styrene as the monomer and TEMPO as the control agent the polymerization goes from an uncontrolled radical polymerization to complete inhibition over a very small change in TEMPO concentration. Upon adding 0.3 equivalents of TEMPO to the free radical emulsion polymerization the weight average molecular weight (M$_w$) and the conversions remain unchanged from the polymerization containing no TEMPO. However, upon addition of 0.6 equivalents or more monomer consumption is completely stopped.

Example 4: α-Hydrido-Nitroxide Control Agent in Aqueous Polymerization

Thirty six stable free radical polymerization (SFRP) were carried out under aqueous emulsion conditions. Each polymerization was set up with a total volume 0.7 mL, with 20 weight % styrene (monomer). The amount of surfactant (sodium alpha (C$_{14}$–C$_{16}$) olefin sulfonate—sold by Rhodia as Rhodacal A-246/L) added was 1 weight % to monomer, and the amount of initiator added was 0.001 mole equivalence to monomer. The initiators that were used were water soluble and were (1) potassium persulfate, (2) tert-butylhydroperoxide (TBHP) and (3) 2,2-azobis(N,N'-dimethyleneisobutyramidine) dihydrochloride (sold by E. I. du Pont de Nemours and Company under the trademark VAZO® 044). For each initiator the series of 12 polymerizations differed in the amount of control agent added, with the first well getting no control agent and the last well getting 3.3 mole equivalence of control agent, with even steps of 0.3 mole equivalence (the control agent used was 2,2,5-trimethyl-4-phenyl-3-azahexane-3-nitroxide—"α-hydrido-nitroxide"). After the predetermined heating and agitation time and temperature (90° C. for 15 h) the reaction mixtures were worked up and characterized using the standard procedure outlined for polymerization experiments at the beginning of the Example section. Polymer was produced in all of the polymerization mixtures.

FIGS. 2A and 2B graphically display the results for the polymerizations where TBHP is used as the initiator. FIG. 2A shows a graph of conversion versus equivalents of nitroxide and FIG. 2B shows a graph of molecular weight versus equivalents of nitroxide. Upon adding from 0.3 equivalents (eq) to 1.5 eq of 2,2,5-trimethyl-4-phenyl-3-azahexane-3-nitroxide (α-hydrido-nitroxide) to the polymerization the weight average molecular weight (M$_w$) and the conversions are reduced in an almost linear fashion. Table 7, below provides selected molecular weight and conversion data.

TABLE 7

| Initiator | α-hydrido-nitroxide to initiator ratio | $M_w$ | Conversion |
|---|---|---|---|
| $K_2S_2O_8$ | 0:1 | 749,265 | 99 |
| $K_2S_2O_8$ | 0.3:1 | 527,763 | 98 |
| $K_2S_2O_8$ | 0.6:1 | 326,648 | 69 |
| $K_2S_2O_8$ | 0.9:1 | 146,769 | 26 |
| $K_2S_2O_8$ | 1.2:1 | 102,554 | 10 |
| TBHP | 0:1 | 544,236 | 97 |
| TBHP | 0.3:1 | 541,576 | 80 |
| TBHP | 0.6:1 | 155,490 | 44 |
| TBHP | 0.9:1 | 143,790 | 60 |
| TBHP | 1.2:1 | 77,163 | 46 |
| TBHP | 1.5:1 | 19,000 | 13 |
| VAZO® 044 | 0:1 | 570,640 | 95 |
| VAZO® 044 | 0.3:1 | 252,908 | 44 |
| VAZO® 044 | 0.6:1 | 111,664 | 26 |

Example 5

Sixty four stable free radical polymerization (SFRP) were carried out under aqueous emulsion conditions. Each polymerization was set up with a total volume 0.7 mL, with 20 weight % styrene (monomer). The amount of surfactant (sodium alpha ($C_{14}$–$C_{16}$) olefin sulfonate—sold by Rhodia as Rhodacal A-246/L) added was 1 weight % to monomer, and four different amounts of initiator were added: 0.001, 0.002, 0.003 and 0.004 mole equivalence to monomer. The two initiators that were used were water-soluble and were (1) potassium persulfate, (2) tert-butylhydroperoxide (TBHP). For each initiator the series of seven polymerizations differed in the amount of control agent added, with the first well getting 0.6 mole equivalence control agent and the last well getting 1.2 mole equivalence of control agent, with even steps of 0.1 mole equivalence (the control agent used was 2,2,5-trimethyl-4-phenyl-3-azahexane-3-nitroxide—"α-hydrido-nitroxide"). In addition a polymerization reaction without control agent was conducted for each initiator type and amount. Four chemically identical copies were made, agitated and heated at 90° C. for 3, 7, 15 and 30 h respectively (thus a total of 256 different polymerizations were actually carried out). After the predetermined heating and agitation time the reaction mixtures were worked up and characterized using the standard procedure outlined for polymerization experiments at the beginning of the Example section. The polymers obtained from these experiments showed a wide range of molecular weights.

FIGS. 3A–E graphically display selected results from these polymerizations. FIG. 3A graphs weight average molecular weight versus reaction time (for 0.6 equivalents of α-hydrido-nitroxide for the initiator TBHP at an initiator to monomer ratio of 0.001 and at 0.6 equivalence of α-hydrido-nitroxide to initiator). FIG. 3B graphs conversion versus reaction time (for 0.6 equivalents of α-hydrido-nitroxide for the initiator TBHP at an initiator to monomer ratio of 0.001 and at 0.6 equivalence of α-hydrido-nitroxide to initiator). FIG. 3C graphs weight average molecular weight versus equivalents of α-hydrido-nitroxide (for the initiator TBHP at a 30 hour polymerization time and at an initiator to monomer ratio of 0.001). FIG. 3D graphs conversion versus equivalents of α-hydrido-nitroxide (for the initiator TBHP at a 30 hour polymerization time and at an initiator to monomer ratio of 0.001). FIG. 3E graphs weight average molecular weight versus the ratio of initiator to monomer (for the initiator TBHP at 0.6 equivalence of α-hydrido-nitroxide to initaitor at a 30 hour polymerization time). As was previously shown in example 5, by increasing the ratio of α-hydrido-nitroxide to the free radical initiator from 0.6 eq to 1.2 eq the weight average molecular weight ($M_w$) and the conversions are decreased in a monotonic fashion. These graphs also show several trends that are known to be associated with living polymerizations. There is a linear relationship between molecular weight and the reaction time, as well as between the conversion and the reaction time. In addition, upon increasing the amount of initiator (while keeping the nitroxide to initiator ratio constant) there is a monotonic decrease in molecular weight.

Example 6: Block Styrene/n-Butylacrylate Polymers

Sixteen stable free radical polymerization (SFRP) were carried out under aqueous emulsion conditions. Each polymerization was set up with a total volume 0.7 mL, with 10 weight % styrene (monomer). The amount of surfactant (sodium alpha ($C_{14}$–$C_{16}$) olefin sulfonate—sold by Rhodia as Rhodacal A-246/L) added was 1 weight % to monomer, and two different amounts of initiator were added: 0.001 and 0.002 mole equivalence to monomer. The initiator that was used was water soluble and was tert-butylhydroperoxide (TBHP). For each initiator concentration the series of seven polymerizations differed in the amount of control agent added, with the first well getting 0.6 mole equivalence control agent and the last well getting 1.2 mole equivalence of control agent, with even steps of 0.1 mole equivalence (the control agent used was 2,2,5-trimethyl-4-phenyl-3-azahexane-3-nitroxide—"α-hydrido-nitroxide"). In addition a polymerization reaction without control agent was conducted for each amount of initiator. After the predetermined heating and agitation time of 90° C. and 30 h the reactor vessels were opened and a small aliquot was taken from each vessel for analysis. Subsequently, an amount of n-butylacrylate equal to the amount of styrene previously added (10 wt %) was dispensed to each vessel. The vessels were then resealed and heated at 90° C. and mixed for an additional 30 h. Subsequently the reaction mixtures were worked up and characterized using the standard procedure outlined for polymerization experiments at the beginning of the Example section.

FIG. 4 is a bar graph of the molecular weight versus the amounts of control agent for both steps of the block copolymerization. After the second stage of polymerization, there was a clear increase of the molecular weights as compared to the molecular weights obtained after polymerization of just the first monomer, suggesting block copolymer formation. In addition, the overall molecular weights still depended on the ratio of 2,2,5-trimethyl-4-phenyl-3-azahexane-3-nitroxide (α-hydrido-nitroxide control agent) to initiator which suggests that the polymerization had not lost its living character.

Example 7: Block n-Butylmethacrylate/Styrene Polymers

Twenty four stable free radical polymerization (SFRP) were carried out under aqueous emulsion conditions. Each polymerization was set up with a total volume 0.7 mL, with 10 weight % n-butylmethacrylate (monomer). The amount of surfactant (sodium alpha ($C_{14}$–$C_{16}$) olefin sulfonate— sold by Rhodia as Rhodacal A-246/L) added was 1 weight % to monomer, and three different amounts of initiator were added: 0.001, 0.002 and 0.003 mole equivalence to monomer. The initiator that was used was water soluble and was tert-butylhydroperoxide (TBHP). For each initiator concentration the series of seven polymerizations differed in the amount of control agent added, with the first well getting 0.6 mole equivalence control agent and the last well getting 1.2 mole equivalence of control agent, with even steps of 0.1 mole equivalence (the control agent used was 2,2,5-trimethyl-4-phenyl-3-azahexane-3-nitroxide—"α-hydrido-nitroxide"). In addition a polymerization reaction without control agent was conducted for each initiator amount. After the predetermined heating and agitation time of 90° C. and 30 h the reactor vessels were opened and a small aliquot was taken from each vessel for analysis. Subsequently, an amount of styrene equal to the amount of n-butylmethacrylate previously added (10 wt %) was dispensed to each vessel. The vessels were then resealed and heated at 90° C. and mixed for an additional 30 h. Subsequently the reaction mixtures were worked up and characterized using the standard procedure outlined for polymerization experiments at the beginning of the Example section.

FIG. 5 is a bar graph of the molecular weight versus the amounts of control agent for both steps of the block copolymerization. After the second stage of polymerization, there was a clear increase of the molecular weights as compared to the molecular weights obtained after polymerization of just the first monomer, suggesting block copolymer formation. Table 8 below provides selected weight average molecular weights for the n-butylmethacrylate polymer and the block copolymer.

TABLE 8

| Initiator Concentration | α-hydrido-nitroxide to initiator ratio | $M_w$ of n-butyl-methacrylate | $M_w$ of block copolymer |
|---|---|---|---|
| 0.001 | 0.6:1 | 254,350 | 291,750 |
| 0.001 | 0.7:1 | 137,370 | 369,130 |
| 0.001 | 0.8:1 | 108,300 | 410,940 |
| 0.001 | 1:1 | 128,870 | 381,270 |
| 0.001 | 1.1:1 | 56,076 | 326,360 |
| 0.001 | 1.2:1 | 66,222 | 261,820 |
| 0.002 | 0.6:1 | 87,128 | 215,110 |
| 0.002 | 0.7:1 | 66,036 | 218,450 |
| 0.002 | 0.8:1 | 59,736 | 238,230 |
| 0.002 | 0.9:1 | 90,003 | 218,400 |
| 0.002 | 1:1 | 48,078 | 219,390 |
| 0.002 | 1.1:1 | 26,565 | 203,920 |
| 0.002 | 1.2:1 | 33,049 | 308,390 |
| 0.002 | 0:1 | 2,621,800 | — |
| 0.003 | 0.6:1 | 59,554 | 182,110 |
| 0.003 | 0.7:1 | 48,574 | 153,210 |
| 0.003 | 0.8:1 | 69,326 | 241,970 |
| 0.003 | 0.9:1 | 54,997 | 125,490 |
| 0.003 | 1:1 | 49,282 | 192,670 |
| 0.003 | 1.1:1 | 32,574 | Er |
| 0.003 | 1.2:1 | 20,079 | Er |
| 0.003 | 0:1 | 2,768,000 | — |

In Table 8, "Er" indicates an error in the testing and "—" indicates no data was taken.

Example 8: Stepwise Addition of Monomers

Sixteen stable free radical polymerization (SFRP) were carried out under aqueous emulsion conditions. Each polymerization was designed to have the following final conditions for the growth of the first block: total volume of 0.7 mL, with 10 weight % of monomer, one weight % to monomer of surfactant (sodium alpha ($C_{14}$–$C_{16}$) olefin sulfonate—sold by Rhodia as Rhodacal A-246/L), and two different amounts of initiator (0.001, 0.002 mole equivalence to monomer). The initiator used was an adduct of the initiator/control agent (the organic soluble 2,2,5-trimethyl-3-(1-phenylethoxy)-4-phenyl-3-azahexane) (eight identical reactions were run at each initiator to monomer ratio). This compound predetermines the control agent to initiator ratio to equal one. The reaction was split into two stages, with all the components except monomer being added in the first step. In the first step 25% of the total monomer (2.5 wt %) was added as styrene, the plate was then sealed and heated at 90° C. for 6 h. The reactor vessels was then allowed to cool, opened and 75% of the total monomer (7.5 weight %) of styrene was added to each reaction vessel. The vessel was then resealed and heated at 90° C. for an additional 30 h. After the predetermined heating and agitation time the reactor vessels were cooled to room temperature and opened and a small aliquot was taken from each vessel for analysis.

Subsequently, an amount of n-butylacrylate equal to the amount of styrene previously added (10 wt %) was dispensed to each vessel. The vessels were then resealed and heated at 90° C. and mixed for an additional 30 h. Finally, the reaction mixtures were worked up and characterized using the standard procedure outlined for polymerization experiments at the beginning of the Example section.

FIG. 6 is a bar graph of monomer to initiator ratio versus weight average molecular weight for the two different initiator concentrations.

Example 9: Initiator/Control Agent Adduct in Emulsion Polymerization Conditions Fifty six stable free radical polymerization reactions were carried out under aqueous emulsion conditions. Each polymerization was set up to have the following final conditions for the growth of a first block: total volume 0.7 mL, with 10 or 5 weight % styrene (monomer), 1 wt % to monomer of surfactant (sodium alpha ($C_{14}$–$C_{16}$) olefin sulfonate—sold by Rhodia as Rhodacal A-246/L), and four different amounts of initiator—0.0005, 0.001, 0.002, 0.003 mole equivalents to monomer. The initiator used was an adduct of the initiator/control agent, the organic soluble 2,2,5-trimethyl-3-(1-phenylethoxy)-4-phenyl-3-azahexane. This compound predetermines the control agent to initiator ratio to equal one. Seven identical reactions were run at each initiator to monomer ratio.

A first homopolymer block was assembled in two stages, with all the components except monomer being added in the first step. In the first step, 2.5 or 1.25 wt % of styrene (25% of the total first monomer) was added to each reaction vessel, and the plate was sealed and heated at 90° C. for 2 hours. The reactor vessels were allowed to cool, were opened, and the remaining 7.5 or 3.75 wt % of styrene (75% of the first monomer) was added to each reaction vessel. The plate was then resealed and heated at 90° C. for an additional 30 hours. The reactor vessels were then cooled to room temperature and opened, and a small aliquot was taken from each vessel for analysis.

Subsequently, 0, 5, 10, 15, 20, 25 or 30 weight % of a second monomer, n-butylacrylate, was dispensed to each polymerization with the predetermined styrene to initiator ratio (4 different initiator concentrations, 7 different weight % of n-butylacrylate and 2 different weight % of styrene for a total of fifty six different polymerizations). The vessels were resealed and heated at 90° C. with mixing for an additional 30 hours. The reaction mixtures were then worked up and characterized using the standard procedure outlined for polymerization experiments at the beginning of the Example section.

FIG. 7 is a bar graph illustrating the reinitiation of Mw 70,000 styrene blocks with a gradient of n-butylacrylate. The final Mw of the block copolymer depends on the amount of n-butylacrylate added in the reinitiation step. Table 9 below provides selected weight average molecular weights for the styrene polymer and the block copolymer.

TABLE 9

| Wt % styrene | Wt % n-butyl-acrylate | Initiator Concentration | $M_w$ of sytrene block | $M_w$ of block copolymer |
|---|---|---|---|---|
| 10 | 5 | 0.0005 | 75,000 | 165,000 |
| 10 | 10 | 0.0005 | 75,000 | 234,000 |
| 10 | 15 | 0.0005 | 75,000 | 238,000 |
| 10 | 20 | 0.0005 | 75,000 | 248,000 |
| 10 | 25 | 0.0005 | 75,000 | 277,000 |
| 10 | 30 | 0.0005 | 75,000 | 300,000 |
| 10 | 5 | 0.001 | 48,000 | 125,000 |
| 10 | 10 | 0.001 | 48,000 | 127,000 |
| 10 | 15 | 0.001 | 48,000 | 143,000 |
| 10 | 20 | 0.001 | 48,000 | 145,000 |
| 10 | 25 | 0.001 | 48,000 | 150,000 |
| 10 | 30 | 0.001 | 48,000 | 155,000 |
| 10 | 5 | 0.002 | 20,000 | 49,000 |
| 10 | 10 | 0.002 | 20,000 | 52,000 |
| 10 | 15 | 0.002 | 20,000 | 55,000 |
| 10 | 20 | 0.002 | 20,000 | 59,000 |
| 10 | 25 | 0.002 | 20,000 | 62,000 |
| 10 | 30 | 0.002 | 20,000 | 69,000 |
| 10 | 5 | 0.003 | 17,000 | 35,000 |
| 10 | 10 | 0.003 | 17,000 | 37,000 |
| 10 | 15 | 0.003 | 17,000 | 39,000 |
| 10 | 20 | 0.003 | 17,000 | 44,000 |
| 10 | 25 | 0.003 | 17,000 | 51,000 |
| 10 | 30 | 0.003 | 17,000 | 66,000 |
| 5 | 5 | 0.0005 | 70,000 | 156,000 |
| 5 | 10 | 0.0005 | 70,000 | 183,000 |
| 5 | 15 | 0.0005 | 70,000 | 248,000 |
| 5 | 20 | 0.0005 | 70,000 | 412,000 |
| 5 | 25 | 0.0005 | 70,000 | 433,000 |
| 5 | 30 | 0.0005 | 70,000 | — |
| 5 | 5 | 0.001 | 50,000 | 100,000 |
| 5 | 10 | 0.001 | 50,000 | 105,000 |
| 5 | 15 | 0.001 | 50,000 | 110,000 |
| 5 | 20 | 0.001 | 50,000 | — |
| 5 | 25 | 0.001 | 50,000 | — |
| 5 | 30 | 0.001 | 50,000 | 197,000 |
| 5 | 5 | 0.002 | 19,000 | — |
| 5 | 10 | 0.002 | 19,000 | — |
| 5 | 15 | 0.002 | 19,000 | — |
| 5 | 20 | 0.002 | 19,000 | 61,000 |
| 5 | 25 | 0.002 | 19,000 | 98,000 |
| 5 | 30 | 0.002 | 19,000 | 102,000 |
| 5 | 5 | 0.003 | 16,000 | 41,000 |
| 5 | 10 | 0.003 | 16,000 | 45,000 |
| 5 | 15 | 0.003 | 16,000 | 46,000 |
| 5 | 20 | 0.003 | 16,000 | 50,000 |
| 5 | 25 | 0.003 | 16,000 | 52,000 |
| 5 | 30 | 0.003 | 16,000 | 59,000 |

Example 10

Forty eight stable free radical polymerization reactions were carried out under aqueous emulsion conditions. Each polymerization was set up with a total volume 0.7 mL, with 10 or 5 weight % styrene (monomer). The amount of surfactant (sodium alpha ($C_{14}$–$C_{16}$) olefin sulfonate—sold by Rhodia as Rhodacal A-246/L) added was 1 weight % to monomer, and four different amounts of initiator were added: 0.0005, 0.001, 0.002, 0.003 mole equivalents to monomer. The initiator used was an adduct of the initiator/control agent, the organic soluble 2,2,5-trimethyl-3-(1-phenylethoxy)-4-phenyl-3-azahexane. This compound predetermines the control agent to initiator ratio to equal one. Seven identical reactions were run at each initiator to monomer ratio.

A first homopolymer block was assembled in two stages, with all the components except monomer being added in the first step. In the first step, 2.5 or 1.25 wt % of styrene (25% of the total first monomer) was added to each reaction vessel, and the plate was sealed and heated at 90° C. for 2 hours. The reactor vessels were allowed to cool, were opened, and an additional 7.5 or 3.75 wt % of styrene (the remaining 75% of the first monomer) was added to each reaction vessel. The plate was then resealed and heated at 90° C. for an additional 30 hours. The reactor vessels were then cooled to room temperature and opened, and a small aliquot was taken from each vessel for analysis.

Subsequently, 0, 1, 2, 5, 7.5 or 10 weight % of a second monomer, acrylic acid, was dispensed to each polymerization with the predetermined styrene to initiator ratio (4 different initiator concentrations, 6 different weight % of acrylic acid and 2 different weight % of styrene for a total of forty eight different polymerizations). The vessels were resealed and heated at 90° C. with mixing for an additional 30 hours. The reaction mixtures were then worked up and characterized using the standard procedure outlined for polymerization experiments at the beginning of the Example section.

FIG. 8 is a bar graph illustrating the reinitiation of Mw 75,000 styrene blocks in the presence of acrylic acid. The molecular weight increase seen in the presence of larger amounts of acrylic acid is believed to be due to continued styrene polymerization with incorporation of acrylic acid. Table 10 below provides selected weight average molecular weights for the styrene polymer and the block copolymer.

TABLE 10

| Wt % styrene | Wt % acrylic acid | Initiator Concentration | $M_w$ of sytrene block | $M_w$ of block copolymer |
|---|---|---|---|---|
| 10 | 0 | 0.0005 | 71,000 | 71,000 |
| 10 | 1 | 0.0005 | 71,000 | 95,000 |
| 10 | 2 | 0.0005 | 71,000 | 112,000 |
| 10 | 5 | 0.0005 | 71,000 | 125,000 |
| 10 | 7.5 | 0.0005 | 71,000 | 147,000 |
| 10 | 10 | 0.0005 | 71,000 | — |
| 10 | 0 | 0.001 | 51,000 | 51,000 |
| 10 | 1 | 0.001 | 51,000 | 62,000 |
| 10 | 2 | 0.001 | 51,000 | 64,000 |
| 10 | 5 | 0.001 | 51,000 | 83,000 |
| 10 | 7.5 | 0.001 | 51,000 | — |
| 10 | 10 | 0.001 | 51,000 | — |
| 10 | 0 | 0.002 | 25,000 | 25,000 |
| 10 | 1 | 0.002 | 25,000 | 27,000 |
| 10 | 2 | 0.002 | 25,000 | 28,000 |
| 10 | 5 | 0.002 | 25,000 | 29,000 |
| 10 | 7.5 | 0.002 | 25,000 | 30,000 |
| 10 | 10 | 0.002 | 25,000 | 32,000 |
| 10 | 0 | 0.003 | 19,000 | 19,000 |
| 10 | 1 | 0.003 | 19,000 | 20,000 |
| 10 | 2 | 0.003 | 19,000 | 20,000 |
| 10 | 5 | 0.003 | 19,000 | 21,000 |
| 10 | 7.5 | 0.003 | 19,000 | — |
| 10 | 10 | 0.003 | 19,000 | 25,000 |
| 5 | 0 | 0.0005 | 78,000 | 78,000 |
| 5 | 1 | 0.0005 | 78,000 | 86,000 |
| 5 | 2 | 0.0005 | 78,000 | — |
| 5 | 5 | 0.0005 | 78,000 | — |
| 5 | 7.5 | 0.0005 | 78,000 | 138,000 |
| 5 | 10 | 0.0005 | 78,000 | — |
| 5 | 0 | 0.001 | 37,000 | 37,000 |
| 5 | 1 | 0.001 | 37,000 | 42,000 |
| 5 | 2 | 0.001 | 37,000 | — |
| 5 | 5 | 0.001 | 37,000 | — |
| 5 | 7.5 | 0.001 | 37,000 | 49,000 |
| 5 | 10 | 0.001 | 37,000 | — |
| 5 | 0 | 0.002 | 25,000 | 25,000 |
| 5 | 1 | 0.002 | 25,000 | — |
| 5 | 2 | 0.002 | 25,000 | 29,000 |
| 5 | 5 | 0.002 | 25,000 | — |
| 5 | 7.5 | 0.002 | 25,000 | 49,000 |
| 5 | 10 | 0.002 | 25,000 | — |
| 5 | 0 | 0.003 | 15,000 | 15,000 |
| 5 | 1 | 0.003 | 15,000 | — |

TABLE 10-continued

| Wt % styrene | Wt % acrylic acid | Initiator Concentration | $M_w$ of sytrene block | $M_w$ of block copolymer |
|---|---|---|---|---|
| 5 | 2 | 0.003 | 15,000 | 20,000 |
| 5 | 5 | 0.003 | 15,000 | — |
| 5 | 7.5 | 0.003 | 15,000 | 34,000 |
| 5 | 10 | 0.003 | 15,000 | — |

Styrene-random-acrylic Acid-block-n-butylacrylate—Random Acrylic Acid Block

Ten stable free radical polymerization reactions were carried out under aqueous emulsion conditions. Each polymerization was set up to have the following final conditions for the growth of a first polymer block: a total volume 0.7 mL, with 5 weight % styrene and 1 weight % to monomer of surfactant (sodium alpha ($C_{14}$–$C_{16}$) olefin sulfonate—sold by Rhodia as Rhodacal A-246/L) and 0.003 mole equivalents of initiator to monomer. The initiator used was an adduct of the initiator/control agent, the organic soluble 2,2,5-trimethyl-3-(1-phenylethoxy)-4-phenyl-3-azahexane. This compound predetermines the control agent to initiator ratio to equal one.

The first block was assembled in two stages. In the first step, 2.5 wt % of styrene (50 % of the total first monomer) was added to each reaction vessel, and the plate was sealed and heated at 90° C. for 2 hours. The reactor vessels were allowed to cool, opened and an additional 2.5 wt % of styrene (the remaining 50% of the first monomer) was added to each reaction vessel. In addition, 0, 1, 2, 5 or 7.5 weight % of acrylic acid was added to each reaction vessel. The vessels were then resealed and heated at 90° C. for an additional 30 hours. After the predetermined heating and agitation time the reactor vessels were cooled to room temperature and opened and a small aliquot was taken from each vessel for analysis.

Subsequently, 5 weight % of a third monomer, n-butylacrylate, was dispensed into each vessel. The vessels were then resealed and heated to 90° C. and mixed for an additional 30 hours. The reaction mixtures were worked up and characterized using the standard procedure outlined for polymerization experiments at the beginning of the Example section.

FIG. 9 is a bar graph illustrating the relationship between the overall molecular weight of the random copolymer and the amount of acrylic acid added to the emulsion polymerization. Table 11.

TABLE 11

| Initiator Concentration | Wt % acrylic acid | $M_w$ of sytrene/ acrylic acid | $M_w$ of block copolymer |
|---|---|---|---|
| 0.003 | 0 | 4800 | 23,000 |
| 0.003 | 1 | 5000 | 24,000 |
| 0.003 | 2 | 10,000 | 26,000 |
| 0.003 | 5 | 17,000 | 31,000 |
| 0.003 | 7.5 | 22,000 | 35,000 |

Example 12: Cyclic Nitroxide Adducts

Four stable free radical polymerization reactions were carried out under aqueous emulsion conditions. Each polymerization was set up to have the following final conditions for the growth of a first polymer block: total volume 0.7 mL, with 10 weight % of styrene (monomer). The amount of surfactant (sodium alpha ($C_{14}$–$C_{16}$) olefin sulfonate—sold by Rhodia as Rhodacal A-246/L) added was 1 weight % to monomer, and two different amounts of initiator were added: 0.001 or 0.002 mole equivalents to monomer. The initiator used was an adduct of the initiator/control agent (5,5-dimethyl-(1 -pyrroline-N-oxide/AIBN adduct). This compound predetermines the control agent to initiator ratio to equal one. Four identical reactions were run at each initiator to monomer ratio.

A block was assembled in two stages, with all the components except monomer being added in the first step. In the first step 2.5 wt % of styrene (25% of the total first monomer) was added to each reaction vessel, and the plate was sealed and heated at 90° C. for 2 hours. The reactor vessels were allowed to cool, opened and the remaining 7.5 wt % of styrene (75 % of the first monomer) was added to each reaction vessel. The plate was resealed and heated at 90° C. for an additional 30 hours. After the predetermined heating and agitation time the reactor vessels were cooled to room temperature and opened and a small aliquot was taken from each vessel for analysis.

Subsequently, 10 wt % of a second monomer, n-butylacrylate, was dispensed to half of the vessels. The vessels were then resealed and heated at 90° C. and mixed for an additional 30 hours. The reaction mixtures were worked up and characterized using the standard procedure outlined for polymerization experiments at the beginning of the Example section. The results are set out in Table 12.

TABLE 12

| Initiator Concentration | $M_w$ of sytrene | $M_w$ of block copolymer |
|---|---|---|
| 0.001 | 98,000 | 217,000 |
| 0.002 | 24,000 | 112,000 |

Example 13: Nitroxide Adducts Containing Heterocycles

Four stable free radical polymerization reactions were carried out under aqueous emulsion conditions. Each polymerization was set up to have the following final conditions for the growth of a first polymer block: total volume of 0.7 mL, with 10 weight % of styrene (monomer), one weight % to monomer of surfactant (sodium alpha (C14–C16) olefin sulfonate—sold by Rhodia as Rhodacal A-246/L), and two different amounts of initiator were added: 0.001, 0.002 mole equivalents to monomer. The initiator used was an adduct of the initiator/control agent (2,2,5-trimethyl-3-(1-pyridinylethoxy)-4-phenyl-3-azahexane. This compound predetermines the control agent to initiator ratio to equal one. Four identical reactions were run at each initiator to monomer ratio.

A first block was assembled in two stages, with all the components except monomer being added in the first step. In the first step 2.5 wt % of styrene (25% of the total first monomer) was added to each reaction vessel, and the plate was sealed and heated at 90° C. for 2 hours. The reactor vessels were allowed to cool, were opened and the remaining 7.5 wt % of styrene (75% of the total first monomer) was added to each reaction vessel. The vessels were resealed and heated at 90° C. for an additional 30 hours. The reactor vessels were cooled to room temperature and opened and a small aliquot was taken from each vessel for analysis.

Subsequently, 10 wt % of a second monomer, n-butylacrylate, was dispensed to half of the vessels. The vessels were then resealed and heated at 90° C. and mixed for an additional 30 hours. The reaction mixtures were worked up and characterized using the standard procedure outlined for polymerization experiments at the beginning of the Example section. The results are set out in Table 13.

TABLE 13

| Initiator Concentration | $M_w$ of styrene | $M_w$ of block copolymer |
| --- | --- | --- |
| 0.001 | 88,000 | 167,000 |
| 0.002 | 26,000 | 67,000 |

Example 14: Polymer Characterization

A. Particle Size Determination

Particle sizes were determined using dynamic light scattering measurements performed at a temperature of 308K in nanopure $H_2O$ on diluted latex samples, at a scattering angle of 90 degrees and a laser wavelength of 800 nm (Precision Detectors). The intensity-intensity autocorrelation function was analyzed using a second order cumulant analysis. A sample plot is illustrated in FIG. 10. In this example, the average hydrodynamic radius was 29 nm (first order cumulant) and the polydispersity index was smaller than 0.09 (second order cumulant), indicating an essentially monodisperse latex.

B. Small Angle X-Ray Scattering

Small angle X-ray scattering (SAXS) measurements were conducted using a custom laboratory source consisting of a rotating anode X-ray generator with a copper target equipped with a nickel foil filter and dual Franks mirrors for monochromatization and focussing of the beam. Films were mounted in copper blocks inside an evacuated sample chamber and annealed at 120° C. for five minutes prior to measurement at that temperature. Scattering images were recorded over 300 s by a two-dimensional multiwire area detector and reduced to a one-dimensional profile by integrating azimuthally along an arc located ±30° C. from the direction normal to the sections composing the specimen. Data were reported in the form of total counts as a function of q, the scattering momentum transfer, defined as $4/\lambda \sin \theta$, where $\lambda = 1.54$ Å is the wavelength of the radiation and $\theta$ is the angle between the transmitted and the scattered radiation.

Films for scattering measurements were prepared by dissolution of sufficient polymer in toluene to yield an approximate concentration of 5 wt%. The resulting solution was placed on top of a water column and the solvent was permitted to evaporate at room temperature and atmospheric pressure over 48 hours. Use of water as a casting substrate minimizes the mechanical deformation of the film upon removal from the casting vessel. The resulting polymer film was removed from the water column and dried first in air for at least 2 hours, and then in vacuum at room temperature for at least 2 hours. The film was cut into sections approximately 3×5 mm in area, and between 3 and 5 sections were stacked to yield a specimen between 1 and 2 mm in thickness. Stacked specimens were then placed in an evacuated oven and annealed for at least 48 hours at 120° C. to remove any residual solvent.

FIG. 11 illustrates the results of SAXS of a polystyrene-block-poly(butyl acrylate) copolymer prepared according to Example 11, above (10 wt % styrene, 10 wt % butyl acrylate, 0.001 equivalents initiator). One scattering maximum is observed, at a position corresponding to a spatial periodicity of 417 Å. This is consistent with local phase separation of the polystyrene and poly(butyl acrylate) chains into spatially separated domains as would be expected for a block copolymer of these two monomers. A random copolymer of styrene and butyl acrylate would be compositionally homogeneous on this length scale and would not produce such a scattering maximum. A blend of polystyrene and poly(butyl acrylate) homopolymer might produce such a maximum during the early stages of macroscopic phase separation of the two polymer species, but such a peak would shift to lower values of q and approach q=0 as phase separation progressed. The persistence of this peak at a nonzero value of q after at least two days of annealing at elevated temperatures argues against this possibility.

C. Reflection Optical Microscopy

Polymer films were imaged by reflection optical micrography using a Leitz Ergolux optical microscope, operating in reflection mode at a magnification of 100×, and the images were captured with a Pixera PVC100C digital camera which was attached to the microscope. Films were prepared by dissolving the polymer in THF at a concentration of approximately 1% by weight. A small drop of the solution was deposited on a clean silicon wafer and the solvent was allowed to dry. The substrate was then annealed in a vacuum oven at 130° C. for approximately 18 hours. FIG. 12 is a sample reflection optical micrograph from a styrene-butyl acrylate copolymer synthesized in emulsion prepared according to Example 11, above (10 wt % styrene, 10 wt % butyl acrylate, 0.001 equivalents initiator). The sharply defined, discrete interference colors are clearly visible in the image, indicating microphase separation in the copolymer. The colors vary continuously instead of discretely. The discrete colors observed in FIG. 12 constitute compelling evidence for block copolymer formation and microphase separation.

D. Transmission Electron Microscopy

Imaging of polymer films by transmission electron microscopy was performed under bright-field, in a JEOL 1200EX transmission electron microscope (TEM), with an accelerating voltage of 100 kV. Images were recorded on Kodak SO-163 film and developed according to standard procedures. Polymer films were prepared for imaging by dissolving the polymer emulsion in THF to a concentration of approximately 1% by weight. Approximately 10 μl of this solution was placed on the surface of a 200-mesh copper electron microscope grid, which was pre-coated with a thin carbon film by the supplier (SPI Supplies, part # 3520C). The carbon film, approximately 20 nm thick, spanned the holes in the copper grid and created a free-standing support for the polymer samples. The solvent was allowed to evaporate, leaving a film of the polymer on the carbon support. (Several specimens were prepared in identical manner, to allow for different staining procedures). The specimens were then annealed in a vacuum oven for approximately 18 hours at 125° C. In order to provide contrast between the domains in the electron microscope, the samples were stained with $RuO_4$ vapors ($RuO_4$ staining kit from SPI Supplies, part # 02592-AB). An aqueous $RuO_4$ solution was prepared following the supplier's instructions. The specimen grids and an open vial containing the $RuO_4$ solution were placed underneath an inverted crystallizing dish, so that the specimens would be exposed to an atmosphere saturated with $RuO_4$ vapors. Individual specimens were removed at times of 5, 15, 30, and 60 minutes, in order to optimize the exposure time for maximum contrast. It was found that exposure times of 30 and 60 minutes gave the best results.

FIGS. 13A and 13B are reproduced from a negative which was captured at a magnification of 30,000 from a styrene-butyl acrylate polymer film prepared according to Example 11, above (10 wt % styrene, 10 wt % butyl acrylate, 0.001 equivalents initiator). The images show a region at the boundary between two sections of film having different thickness. The film thickness is restricted to a set of discrete values, as discussed above. At the boundary between these sections, a fairly regular microstructure is clearly observed. The period of the microstructure is obtained by dividing the period on the negative by the magnification, which gives approximately 1.1 mm/30,000=36 nm. The type of morphology shown in FIGS. 13A and 13B is essentially identical to that reported in B. L. Carvalho and E. L Thomas, *Phys. Rev. Lett.*, 73, pp 3321–4, for a styrene-block-isoprene copolymer with a lamellar morphology and a molecular weight of 108,000 gm/mol, using a similar sample preparation method. In both cases, the lamellae in most parts of the film lie parallel to the carbon film in most parts of the image, and are thus not visible. However the lamellae are oriented vertically at the boundaries between regions containing different number of layers, as this configuration has a lower free energy than other types of defects which could occur at such a boundary.

Example 15: Preparation of Seed Emulsions

A. Copolymer of Styrene:t-butylacrylamide:2-acrylamido-2-methylpropanesulfonic Acid (AMPS) 1:1:0.02 by Weight In a 250 mL Morton flask (fitted with mechanical stirrer, thermometer, and oil bath heating) under argon atmosphere were combined 2-acrylamido-2-methylpropanesulfonic acid (AMPS)(Aldrich, 0.20g), styrene (Aldrich, 10.0 g), t-butylacrylamide (Aldrich, 10.0 g), α-olefin sulfonate surfactant (Rhodia, Rhodacal A-246/L, 25.0 g of a ca. 40% aqueous solution), and water (145 g). The mixture was stirred and heated in a 100° C. oil bath until an internal temperature of ca. 75° C. was obtained, and then a solution of initiator ($K_2S_2O_8$, Aldrich, 0.20 g, dissolved in 10 mL $H_2H$) was added all at once via a syringe. The appearance of the nearly opaque aqueous monomer slurry changed quickly over a period of 1–4 minutes to form a translucent, bluish scattering emulsion. The mixture was stirred and heated for an additional 3 h (internal temperature of 92° C.) to decompose the excess initiator. The mixture was cooled with stirring, and filtered to remove a small amount of suspended solid. Yield 197.4 g of emulsion, pH ca. 4.0 to pH paper, 15.75% solids, particle size=12.9 nm $R_h$, by DLS, (Second Cumulant Analysis (PDI)=0.10).

B. Copolymer of Butyl Acrylate:t-butylacrylamide:AMPS 1:1:0.02 by Weight

In a 250 mL Morton flask (fitted with mechanical stirrer, thermometer, and oil bath heating) under argon atmosphere were combined AMPS (Aldrich, 0.20 g), butyl acrylate (Aldrich, 10.0 g), t-butylacrylamide (Aldrich, 10.0 g), α-olefin sulfonate surfactant (Rhodia, Rhodacal A-246/L, 25.0 g of a ca. 40% aqueous solution), and water (145 g). The mixture was stirred and heated in a 100° C. oil bath until an internal temperature of ca. 75° C. was obtained, and then a solution of initiator ($K_2S_2O_8$, Aldrich, 0.20 g, dissolved in 10 mL $H_2O$) was added all at once via a syringe. The appearance of the nearly opaque aqueous monomer emulsion changed quickly over a period of 1–4 minutes to form a translucent, bluish scattering emulsion. The mixture was stirred and heated for an additional 3.5 h (internal temperature of 92° C.) to decompose the excess initiator. The mixture was cooled with stirring, and filtered to remove a small amount of suspended solid. Yield 195.7 g of emulsion, pH ca. 3.5 to pH paper, 15.58% solids, particle size=15.7 nm $R_h$, by DLS, (2nd cumulant analysis PDI=0.19).

C. Copolymer of t-butylacrylamide:4-styrenesulfonic Acid Sodium Salt 99:1 by Weight In a 250 mL Morton flask (fitted with mechanical stirrer, thermometer, and oil bath heating) under argon atmosphere were combined 4-styrenesulfonic acid sodium salt hydrate (0.10 g), t-butylacrylamide (Aldrich, 9.9 g), α-olefin sulfonate surfactant (Rhodia, Rhodacal A-246/L, 12.5 g of a ca. 40% aqueous solution), and water (175 g). The mixture was stirred and heated in a 90° C. oil bath until an internal temperature of ca. 75° C. was obtained, and then solid initiator ($K_2S_2O_8$, Aldrich, 0.20 g) was added all at once. The appearance of the aqueous monomer slurry changed quickly over a period of 1–4 minutes, with the solid dissolving to form a nearly transparent, bluish scattering emulsion. The mixture was stirred and heated in a 100° C. oil bath for an additional 2 h (internal temperature of 93° C.) to decompose the excess initiator. The mixture was cooled with stirring, and filtered to remove any suspended solid. Yield 196.2 g of emulsion, pH ca. 3 to pH paper, 8.07% solids, particle size=9.3 nm $R_h$, by DLS, (2nd cumulant analysis PDI=0.10).

D. Copolymer of Butyl Acrylate:4-styrenesulfonic Acid Sodium Salt 1:0.01 by Weight In a 250 mL Morton flask (fitted with mechanical stirrer, thermometer, and oil bath heating) under argon atmosphere were combined 4-styrenesulfonic acid sodium salt hydrate (0.20 g), butyl acrylate (Aldrich, 20.0 g), α-olefin sulfonate surfactant (Rhodia, Rhodacal A-246/L, 25.0 g of a ca. 40% aqueous solution), and water (145 g). The mixture was stirred and heated in a 90° C. oil bath until an internal temperature of ca. 75° C. was obtained, and then a solution of initiator ($K_2S_2O_8$, Aldrich, 0.40 g, dissolved in 10 mL $H_2O$) was added all at once via a syringe. The appearance of the nearly opaque aqueous monomer emulsion changed quickly over less than 5 minutes to form a translucent, bluish scattering emulsion. The mixture was stirred and heated for an additional 6 h in the 90° C. oil bath to decompose the excess initiator. The mixture was cooled with stirring, and filtered to remove a small amount of suspended solid. Yield 197.5 g of emulsion, pH ca. 3.5 to pH paper, 15.75% solids, particle size=14.7 nm $R_h$, by DLS, (2nd cumulant analysis PDI=0.18).

E. Copolymer of Styrene:4-styrenesulfonic Acid Sodium Salt 1:0.01 by Weight

In a 250 mL Morton flask (fitted with mechanical stirrer, thermometer, and oil bath heating) under argon atmosphere were combined 4-styrenesulfonic acid sodium salt hydrate (0.20 g), butyl acrylate (Aldrich, 20.0 g), a-olefin sulfonate surfactant (Rhodia, Rhodacal A-246/L, 25.0 g of a ca. 40% aqueous solution), and water (145 g). The mixture was stirred and heated in a 90° C. oil bath until an internal temperature of ca. 75° C. was obtained, and then a solution of initiator ($K_2S_2O_8$, Aldrich, 0.40 g, dissolved in 10 mL $H_2O$) was added all at once via a syringe. The appearance of the nearly opaque aqueous monomer emulsion changed quickly over less than 5 minutes to form a translucent, bluish scattering emulsion. The mixture was stirred and heated for an additional 6 h in the 95° C. oil bath (internal temperature ca. 92° C.) to decompose the excess initiator. The mixture was cooled with stirring, and filtered to remove a small amount of suspended solid. Yield 198.9 g of emulsion, pH ca. 4 to pH paper, 15.65% solids, particle size=12.3 nm $R_h$, by DLS, (2nd cumulant analysis PDI=0.07).

F. Diafiltered Emulsion Copolymer of Styrene:4-styrenesulfonic Acid Sodium Salt 1:0.01 by Weight 75.0 g of the emulsion from procedure E above was diafiltered using a hollow-fiber polysulfone membrane (nominal cutoff 100,000 MW), in a recirculating pressurized diafiltratation apparatus driven by a peristaltic pump (AG Technologies, MidGee). The volume was reduced to ca 60 mL, and then pure water added to maintain constant volume, as ca. 280 mL filtrate was removed (ca. 4.6 turnovers). The retentate was rediluted to 75 g total mass. The emulsion remained at 14.60% solids, indicating that relatively little of the surfactant was removed. Particle size measurement by DLS was found to depend strongly on the emulsion concentration, with the most dilute sample showing 12.5 nm $R_h$, by DLS, (2nd cumulant analysis PDI=0.28), near the average of the starting sample, while the sample at full concentration showed an apparend size of 28.3 nm $R_h$, by DLS, (2nd cumulant analysis PDI=0.44), indicating perhaps some particle interactions.

Example 16: Preparation of Seeded Living Emulsion Polymer of Styrene

A. Seed Loading Procedure

In a 20 mL glass vial was placed 0.120 g of the bis-carboxy-α-hydrido alkoxyamine, (compound 20, example 1) 100 μL of $CH_2Cl_2$, and 100 μL of triethylamine. The mixture was gently swirled until almost all solid dissolved, and then 10.0 g of the styrene:t-butylacrylamide:AMPS seed emulsion prepared in Example 15A was added, and the mixture was capped and shaken vigorously for several seconds. The mixture appeared to become less turbid over a period of ca. 30 minutes, with shaking repeated ever few minutes. The loaded seed was allowed to stand at ambient temperature for ca. 3 days with no apparent visual change. The mixture was uncapped and heated in a 100° C. oil bath with magnetic stirring for 2 minutes, and then stirred uncapped at ambient temperature in a fume hood for 30 minutes, to allow most of the $CH_2Cl_2$ to evaporate. Then 250 μL of styrene was added, the mixture was capped and stirred for 1 hour, until the styrene appeared to load, resulting in a translucent dispersion visually similar to the starting seed emulsion, with a small amount of suspended solid. The mixture was filtered through a small glass-fiber mat to remove the solid. The pH was measured with pH paper as ca. 8.

B. Living Emulsion Polymerization of Styrene

The loaded seed emulsion from procedure A in this example was added to a stirred 250 mL Morton flask (equipped with magnetic stirrer, thermometer, under argon atmosphere) containing degassed water (150 mL). The pH was ca. 7 to pH paper. Then 1.8 mL of a 10% by weight solution of AMPS monomer (2-acrylamido-2-methylpropane sulfonic acid) in water was added, and the pH was found to be ca. 3.5 to pH paper. The flask was placed into an oil bath heated to 100° C., which maintained an internal temperature of ca. 93° C. After 40 minutes, a 1 mL sample (Sample 16-1) of the emulsion was withdrawn for analysis, and then 2 mL degassed styrene was added. A 1 mL sample (Sample 16-2) was withdrawn for analysis after 5 h total reaction time, and 10 mL additional degassed styrene monomer was added. A 1 mL sample (Sample 16-3) was withdrawn for analysis after 16 h total reaction time, and 10 mL additional degassed styrene monomer was added, completing the addition of 20 g of total styrene planned (aiming for 20 g monomer/180 g total emulsion). A 1 mL sample (Sample 16-4) was withdrawn for analysis after 22.3 h total reaction time. After 40.7 h total reaction, another sample (Sample 16-5) was removed, and the reaction mixture was cooled with stirring, the resulting white-translucent emulsion was filtered to remove suspended solid (ca. 1.5 g of solid styrene coagulum was isolated). Yield 170.3 g emulsion, 10.31% solids, 0.90% total residual styrene (by quantitative GC analysis, 8.1% of total styrene added, corresponding to 91.9% monomer conversion to polymer). Molecular weight by traditional GPC (THF eluent) showed a peak molecular weight of 89,400, $M_n$ of 70,400, and a PDI ($M_w/M_n$) or 1.7, with a small peak at higher molecular weight corresponding to the seed polymer.

A summary of analyses of the reaction aliquots and final emulsion are contained in Table 14. The % solids were measured by weighing samples imbibed into glass fiber pads, with microwave drying. The % conversion from % solids is calculated by subtracting the expected contribution of non-volatile components in the mixture (AMPS, seed, surfactant). The theoretical Rh is calculated from the conversion, assuming the same density of seed polymer and living polymer, linear particle volume growth with conversion, and a constant number of particles throughout the polymerization.

TABLE 14

| sample # | % solids | rxn time, h | % conv. from % solids | Rh (nm) OLS | % mon. by GC | % conv from GC | Rapid GPC Mp | theor. Rh by conv | GPC Mp kdalton | GPC Mw | GPC Mn | GPC PDI |
|---|---|---|---|---|---|---|---|---|---|---|---|---|
| 16-0 (seed) | 1.17% | 0 | 0.000 | 12.9 | 0.00% | 0 | 0 | 12.9 | ** | ** | ** | ** |
| 16-1 | 1.23% | 0 | 1.094 | 15.9 | 0.06% | 0.68 | 0 | 13.8 | ** | ** | ** | ** |
| 16-2 | 1.58% | 5 | 4.042 | ** | 0.52% | 6.01 | 5.1 | 15.7 | ** | ** | ** | ** |
| 16-3 | 4.68% | 16 | 31.286 | 27.2 | 2.28% | 36.17 | 33.7 | 25.0 | 34.3 | 36.5 | 25.0 | 1.46 |
| 16-4 | 7.02% | 22.3 | 54.420 | 31.8 | 3.93% | 64.63 | 52.3 | 29.4 | 51.9 | 67.1 | 45.6 | 1.47 |
| 16-5 | 10.30% | 40.7 | 83.940 | 34.85 | 0.90% | 91.91 | 83.1 | 33.7 | 89.4 | 119.4 | 70.4 | 1.70 |

**indicates that the value was not measured for a particular sample

The charts in FIGS. 14A–D show the expected trends for a living emulsion polymerization —including linear growth of molecular weight with conversion and linear particle volume growth with conversion, indicating a constant number of particles during the formation of polymer. Also, the conversion kinetics with the α-hydrido alkoxyamine at a temperature of less than 100° C. are much faster than those seen for non-α-hydrido structures.

C. Chain Extension of the Living Styrene Emulsion with Additional Styrene Monomer In a 10 mL capacity round-bottom flask, equipped with a magnetic stirbar, in a nitrogen-filled glovebox was placed 9.0 mL of the emulsion prepared in part B in this example above, followed by 0.9 mL additional degassed styrene. The flask was sealed, removed from the glovebox, and heated in a 95° C. oil bath with stirring for 39 h. The mixture was cooled and the emulsion was decanted from a small amount of coagulum. Analysis of the emulsion showed 13.5% solids, Mp by GPC (THF eluent) of 133,000, Mw=158,300, Mn=96,100, Mw/Mn=1.65. Particle size by DLS was found to be $R_h$=41.4 nm, 2nd cumulant analysis PDI=0.04. The molecular weight increase and particle size increase are consistent with chain extension of the living chains in the emulsion with additional styrene. Overlay of the GPC traces before and after the chain extension procedure suggests that essentially the entire molecular weight distribution shifted to higher molecular weight.

D. Chain Extension of the Living Styrene Emulsion with Butyl Methacrylate Monomer In a 50 mL capacity 3-neck round-bottom flask, equipped with a magnetic stirbar, thermometer, and nitrogen inlet was placed 30.0 mL of the emulsion prepared in procedure B in this example, above, followed by 3.5 mL degassed butyl methacrylate. The flask was heated in a 95° C. oil bath with stirring for 6 days, with daily sampling of ca. 0.5 mL aliquots for analysis. Percent solids and molecular weight increased for about 30 hours. After 30 hours, the percent solids decreased as coagulum formed, while molecular weight continued to increase for an additional 24 hours. The mixture was cooled and the emulsion was decanted from a significant amount of coagulum. Analysis of the emulsion showed 9.80% solids, Mp by GPC of 124,900, Mw=161,400, Mn=95,400, Mw/Mn=1.7. Particle size by DLS was measured as $R_h$=40.4 nm. $^1$H NMR analysis of a dried sample of the polymer from the emulsion in CDCl$_3$ showed a broad peak at 3.9 ppm, consistent with the methylene signals of the butyl ester incorporated in the polymer. Comparison of the integrals of the ester peak with the aromatic polystyrene peaks indicated the presence of 21 weight percent of butyl methacrylate. Overlay of the GPC traces before and after the chain extension procedure indicate that essentially the entire molecular weight distribution shifted to higher molecular weight.

E. Chain Extension of the Living Styrene Emulsion with Methyl Methacrylate/2-(2-Oxo-1-imidazolidnyl)ethyl Methacrylate Monomer Mixture In a 10 mL capacity round-bottom flask, equipped with a magnetic stirbar, in a nitrogen-filled glovebox was placed 9.0 mL of the emulsion prepared in procedure B, in this example, above, followed by 0.9 mL a commercially available 25 wt.% solution of 2-(2-oxo-1-imidazolidnyl)ethyl methacrylate (ureidoethyl methacrylate) in methyl methacrylate (Aldrich). The flask was sealed, removed from the glovebox, and heated in a 95° C. oil bath with stirring for 39 h. The mixture was cooled and the emulsion was decanted from a very small amount of coagulum. Analysis of the emulsion showed 17.0% solids, Mp by GPC of 102,200, Mw=128,500, Mn=62,000, Mw/Mn=2.10. Because of concerns that the polar ureido monomer might promote polymer adsorption to the stationary phase with THF eluent, giving artificially small molecular weight results, rapid 16 minute GPC analysis was conducted with dimethylformamide eluent containing 0.1% trifluoroacetic acid. Mp by this method was found to be 170,900, Mw of 232,700, and Mn of 139,700, with Mw/Mn=1.7. Particle size of the emulsion by DLS was 40.8 nm Rh (2nd cumulant analysis PDI=0.02). Overlay of the GPC traces by both GPC methods before and after the chain extension procedure indicate that essentially the entire molecular weight distribution shifted to higher molecular weight. $^1$H NMR analysis of a dried sample of the polymer from the emulsion in THF-d$_8$ showed a large broad signal from 0.5–1.3 ppm consistent with incorporated methacrylate monomer. Also, broad signal was observed at 4.1 corresponding to two methylene protons of the polymerized ureido monomer. Comparison of these two peaks with the aromatic polystyrene signals from 6.4–7.5 ppm indicates a weight ratio of 64.3% polystyrene, 26.0% poly(methyl methacrylate) and 9.8% ureidoethylmethacrylate polymer.

Analysis of the polymer by two different normal phase gradient elution techniques and by one reverse-phase gradient elution technique indicate the presence of very little styrene homopolymer, indicating that most of the polystyrene chains incorporated at least some methacrylate monomer, forming block copolymer.

Example 17: Semi-continuous Preparation of Seeded Living Emulsion Polymer of Styrene

A. Seed Loading Procedure

In a 20 mL glass vial was placed 0.164 g of the p-(aminomethyl)-1-phenethyl-α-hydrido alkoxyamine, (compound 23, example 1) was dissolved in 340 µL of CH$_2$Cl$_2$. Then 9.0 g of the styrene:t-butylacrylamide:AMPS seed emulsion prepared in Example 15A, and the mixture was capped and shaken vigorously for several seconds. The mixture appeared to become less turbid over a period of ca. 15 minutes, with shaking repeated every few minutes for 30 minutes. The mixture was uncapped and heated in a 100° C. oil bath with magnetic stirring for 2 minutes, and then stirred uncapped at ambient temperature in a fume hood for 30 minutes, to allow most of the CH$_2$Cl$_2$ to evaporate. Then 250 µL of styrene was added, the mixture was capped and stirred for 30 minutes, until the styrene appeared to load, resulting in a translucent dispersion visually similar to the starting seed emulsion, with a small amount of suspended solid. The mixture was filtered through a small glass-fiber mat to remove the solid.

B. Living Emulsion Polymerization of Styrene

The loaded seed emulsion from procedure A of this example was added to a stirred 250 mL Morton flask (equipped with magnetic stirrer, thermometer, under argon atmosphere) containing degassed water (160 mL). The bluish scattering, nearly transparent mixture was heated placed in a 100° C. oil bath and heated to an internal temperature of 92° C. for 0.5 hour. An aliquot of ca. 1 mL volume was removed for analysis (Sample 17-1), and a syringe pump was used to begin feed of 2.75 mL degassed styrene monomer over 2 hours, with the beginning of this feed marking the start of the polymerization process. After 2 hours, 2.9 mL of a 10% by weight of AMPS monomer in water was added, which lowered the pH of the polymerizing mixture from ca. 9 to ca. 3, and then the syringe pump was used to begin an 8 hour feed of 30 mL degassed styrene monomer. An additional nine sample aliquots (17-2 through 17-10) were withdrawn during the 8 hour feed and the remaining time of the 47 hour period during which the reaction was heated and stirred. A visible crust of coagulated or dried polymer had formed on the surface of the reaction mixture. The mixture was cooled with stirring, the coagulum was removed, and the emulsion was analysed. Yield of about 172 g of bluish scattering emulsion, 9.41% solids, particle size by DLS= 39.1 nm Rh, GPC (THF eluent) Mp=66,800, Mw=67,900, Mn=26,700, with a noticeable peak at higher molecular weight corresponding to the seed polymer.

A summary of analyses of the reaction aliquots and final emulsion are contained in Table 15. The % solids were measured by weighing samples imbibed into glass fiber pads, with microwave drying. The % conversion from % solids is calculated by subtracting the expected contribution of non-volatile components in the mixture (AMPS, seed, surfactant). The theoretical $R_h$ is calculated from the conversion, assuming the same density of seed polymer and living polymer, linear particle volume growth with conversion, and a constant number of particles throughout the polymerization.

TABLE 15

| sample # | % solids | rxn time, h | % conv. from % solids | Rh (nm) OLS | % mon. by GC | % conv from GC | Rapid GPC Mp | theor. Rh by conv | GPC Mp kdalton | GPC Mw | GPC Mn | GPC PDI |
|---|---|---|---|---|---|---|---|---|---|---|---|---|
| 17-0 (seed) | 0.89% | 0.00 | 0.000 | 12.900 | 0.00% | 0 | ** | 12.9 | ** | ** | ** | ** |
| 17-1 | 0.93% | 0.00 | 0.777 | ** | 0.05% | 0.47 | ** | 13.9 | ** | ** | ** | ** |
| 17-2 | 0.92% | 2.00 | 0.797 | ** | 0.74% | 4.82 | ** | 14.0 | ** | ** | ** | ** |
| 17-3 | 1.06% | 2.25 | 0.646 | ** | 0.78% | 4.62 | ** | 13.8 | ** | ** | ** | ** |
| 17-4 | 1.21% | 3.58 | 1.693 | ** | 1.37% | 16.15 | ** | 15.0 | ** | ** | ** | ** |
| 17-5 | 1.42% | 4.92 | 3.149 | ** | 1.50% | 29.76 | ** | 16.4 | ** | ** | ** | ** |
| 17-6 | 2.28% | 7.58 | 9.052 | ** | 4.57% | 40.62 | ** | 20.5 | ** | ** | ** | ** |
| 17-7 | 3.92% | 12.83 | 20.676 | ** | 4.63% | 69.13 | 2297 | 25.7 | ** | ** | ** | ** |
| 17-8 | 5.85% | 22.50 | 33.543 | 31.900 | 5.76% | 61.60 | 15792 | 29.7 | 43.2 | 50.3 | 25.0 | 2.01 |
| 17-9 | 6.86% | 28.83 | 40.276 | 35.200 | 4.89% | 67.40 | 23331 | 31.4 | 50.5 | 49.6 | 28.2 | 1.76 |
| 17-10 | 9.41% | 47.00 | 57.276 | 39.100 | 3.12% | 79.20 | 48364 | 35.1 | 66767 | 67.9 | 26.7 | 2.54 |

**indicates that the value was not measured for a particular sample

The charts in FIGS. 15A–D show the expected trends for a living emulsion polymerization—including growth of molecular weight with conversion and linear particle volume growth with conversion, indicating a constant number of particles during the formation of polymer. The discrepancy between rapid GPC and the slower methods appear to be caused by the amino functionality on the polymer chain promoting adsorption of the polymer to the stationary phase in the rapid method. Chain extension of this living emulsion polymer with additional styrene and other monomers proceeded in a similar fashion to that shown in Example 16.

ninth vial was similarly prepared with 0.300 g of the nitroxide, and 5.00 g of the butyl acrylate:styrenesulfonate seed emulsion described in Example 1 5D. The samples were briefly shaken about every 15 minutes for 3 hours, and then were allowed to stand for three days. Visual observation of turbidity and color was noted during the entire procedure, using room light and a handheld red laser source to visualize scattering from large and small particles, and selected samples were examined by dynamic light scattering after standing for the three day period.

TABLE 16

| sample #/ Seed used * | Type and g of seed added | g of 5% A246/L soln | Control or not | Visual @ 3 h | Visual @ 3 days | 3-day Particle $R_h$ by DLS | DLS 2nd cumulant PDI |
|---|---|---|---|---|---|---|---|
| 18-1 | 15E/20.0 | 0 | | loaded/ orange | loaded/ orange | 14.6 | .25 |
| 18-2 | 15E/10.0 | 0 | | loaded/ orange | loaded/ orange | 15.2 | .28 |
| 18-3 | 15E/5.0 | 0 | | loaded/ orange | loaded/ orange | 18.1 | .30 |
| 18-4 | 15E/2.5 | 0 | | loaded/ orange | loaded/ orange | ** | ** |
| 18-5 | 15E/1.25 | 0 | | some creaming | unstable | ** | ** |
| 18-6 | 0 | 20.0 | Control | clear yellow | clear yellow | 504.1 | .64 |
| 18-7 | 0 | 5.0 | Control | creaming orange | creaming orange | ** | ** |
| 18-8 | 0 | 2.5 | Control | creaming orange | creaming orange | ** | ** |
| 18-9 | 15D/5.0 | 0 | | loaded/ orange | loaded/ orange | 25.4 | .33 |

*0.30 g of nitroxide was added to each sample
**indicates that the value was not measured for a particular sample Example 18: Preparation of Nitroxide-Loaded Seed Emulsions In five 20 mL vials were placed 0.300 g of the α-hydrido nitroxide (compound 5a, example 1), followed by addition of various amounts of the styrene: styrenesulfonate seed emulsion described in Example 1 5E. The vials were capped and shaken vigorously by hand for ca 30 seconds after the emulsion was added. As a control experiment, three additional vials were prepared with 0.300 g of the nitroxide, to which were added various amounts of a 5% aqueous solution of the same surfactant present in the seed emulsion, (Rhodacal A-246/L, Rhodia), followed by similar shaking. A The most dilute control experiment, sample 18-6, appeared to be transparent yellow, perhaps with some of the nitroxide loading into the surfactant micelles. However, DLS showed the presence of very large particles in this system. The loaded seed emulsions of this example generally appeared to form small-particle loaded seed emulsions after 5–30 minutes. Particularly samples 1–4 and 9, are suitable for use in living emulsion polymerization processes with external free-radical initiator.

It is to be understood that the above description is intended to be illustrative and not restrictive. Many embodiments will be apparent to those of skill in the art upon reading the above description. The scope of the invention should therefore be determined not with reference to the above description, but should instead be determined with reference to the appended claims, along with the full scope of equivalents to which such claims are entitled. The disclosures of all articles, patents and references, including patent applications and publications, are incorporated herein by reference for all purposes.

What is claimed is:

1. A heterogeneous free radical polymerization process comprising:

forming a seed having a hydrodynamic radius of less than or equal to about 25 nanometers;

loading said seed with either (1) a composition comprised of initiating radical and control agent or (2) an initiator-control agent adduct; and polymerization one or more heterogeneous mixtures comprising a first polymerizable monomer and a second polymerizable monomer with said loaded seed to form a copolymer derived from the first polymerizable monomer and the second polymerizable monomer.

2. A heterogeneous free radical polymerization process comprising:

forming a first mixture comprised of a first polymerizable monomer, initiator, water and surfactant, wherein said first polymerizable monomer comprises no more than 10% by weight of said first mixture;

subjecting said first mixture to polymerization conditions to give a first heterogeneous polymerization;

ending said first heterogeneous polymerization to provide a seed, and optionally recovering said seed;

forming a second mixture comprised of said seed, water and either (1) a composition comprised of an initiator and control agent or (2) an initiator-control agent adduct;

optionally maintaining said second mixture for a sufficient time for either of said composition or said adduct to migrate into said seed;

forming a third mixture comprised of said second mixture, additional water, surfactant and at least one monomer, which may be the same or different from said first polymerizable monomer; and subjecting said third mixture to polymerization conditions to polymerize said at least one monomer.

3. The process of claim 2, wherein said second mixture further comprises an organic solvent selected from the group consisting of methylenechloride or ethylacetate.

4. The process of claim 2, wherein said second mixture further comprises a base.

* * * * *

UNITED STATES PATENT AND TRADEMARK OFFICE
CERTIFICATE OF CORRECTION

PATENT NO. : 6,559,255 B2
DATED : May 6, 2003
INVENTOR(S) : Klaerner et al.

It is certified that error appears in the above-identified patent and that said Letters Patent is hereby corrected as shown below:

<u>Column 77,</u>
Line 15, "polymerization" should be deleted and -- polymerizing -- inserted Signed and Sealed this Twenty-third Day of September, 2003

JAMES E. ROGAN
*Director of the United States Patent and Trademark Office*